(12) United States Patent
Abkevich et al.

(10) Patent No.: US 9,388,472 B2
(45) Date of Patent: *Jul. 12, 2016

(54) METHODS AND MATERIALS FOR ASSESSING LOSS OF HETEROZYGOSITY

(71) Applicant: Myriad Genetics, Inc., Salt Lake City, UT (US)

(72) Inventors: Victor Abkevich, Salt Lake City, UT (US); Alexander Gutin, Salt Lake City, UT (US); Kirsten Timms, Salt Lake City, UT (US); Jerry Lanchbury, Salt Lake City, UT (US)

(73) Assignee: Myriad Genetics, Inc., Salt Lake City, UT (US)

( * ) Notice: Subject to any disclaimer, the term of this patent is extended or adjusted under 35 U.S.C. 154(b) by 8 days.

This patent is subject to a terminal disclaimer.

(21) Appl. No.: 14/307,708

(22) Filed: Jun. 18, 2014

(65) Prior Publication Data
US 2015/0018527 A1 Jan. 15, 2015

Related U.S. Application Data

(63) Continuation of application No. PCT/US2012/071380, filed on Dec. 21, 2012.

(60) Provisional application No. 61/578,713, filed on Dec. 21, 2011, provisional application No. 61/654,402, filed on Jun. 1, 2012.

(51) Int. Cl.
*C12Q 1/68* (2006.01)

(52) U.S. Cl.
CPC ........ *C12Q 1/6886* (2013.01); *C12Q 2600/106* (2013.01); *C12Q 2600/154* (2013.01); *C12Q 2600/156* (2013.01); *C12Q 2600/158* (2013.01)

(58) Field of Classification Search
None
See application file for complete search history.

(56) References Cited

U.S. PATENT DOCUMENTS

| 3,590,028 A | 6/1971 | Arcamone et al. |
| 3,892,790 A | 7/1975 | Tobe et al. |
| 3,904,663 A | 9/1975 | Tobe et al. |
| 4,138,480 A | 2/1979 | Gosalvez et al. |
| 4,946,954 A | 8/1990 | Talebian et al. |

(Continued)

FOREIGN PATENT DOCUMENTS

| EP | 0430402 | 6/1991 |
| WO | 9520952 | 8/1995 |

(Continued)

OTHER PUBLICATIONS

Tuna, M. et al. PLoS One 5(11):e15094 (Nov. 30, 2010).*

(Continued)

*Primary Examiner* — Diana B Johannsen
(74) *Attorney, Agent, or Firm* — Myriad Genetics, Inc. IP Dept.

(57) ABSTRACT

This document provides methods and materials involved in assessing samples (e.g., cancer cells) for the presence of a loss of heterozygosity (LOH) signature. For example, methods and materials for determining whether or not a cell (e.g., a cancer cell) contains an LOH signature are provided. Materials and methods for identifying cells (e.g., cancer cells) having a deficiency in homology directed repair (HDR) as well as materials and methods for identifying cancer patients likely to respond to a particular cancer treatment regimen also are provided.

36 Claims, 28 Drawing Sheets

(56) References Cited

U.S. PATENT DOCUMENTS

| | | | |
|---|---|---|---|
| 4,950,738 A | 8/1990 | King et al. |
| 4,996,337 A | 2/1991 | Bitha et al. |
| 5,091,521 A | 2/1992 | Kolar et al. |
| 5,177,075 A | 1/1993 | Suto et al. |
| 5,295,944 A | 3/1994 | Teicher et al. |
| 5,434,256 A | 7/1995 | Khokhar et al. |
| 5,445,934 A | 8/1995 | Fodor et al. |
| 5,510,270 A | 4/1996 | Fodor et al. |
| 5,527,905 A | 6/1996 | Sugimura et al. |
| 5,539,083 A | 7/1996 | Cook et al. |
| 5,556,752 A | 9/1996 | Lockhart et al. |
| 5,578,832 A | 11/1996 | Trulson et al. |
| 5,633,016 A | 5/1997 | Johnson et al. |
| 5,633,243 A | 5/1997 | Sugimura et al. |
| 5,744,305 A | 4/1998 | Fodor et al. |
| RE36,397 E | 11/1999 | Zhang et al. |
| 6,040,138 A | 3/2000 | Lockhart et al. |
| 6,087,340 A | 7/2000 | Gatti et al. |
| 6,210,891 B1 | 4/2001 | Nyren et al. |
| 6,214,821 B1 | 4/2001 | Daoud |
| 6,258,568 B1 | 7/2001 | Nyren et al. |
| 6,274,320 B1 | 8/2001 | Rothberg et al. |
| 6,403,563 B1 | 6/2002 | Geroni et al. |
| 6,455,258 B2 | 9/2002 | Bastian et al. |
| 6,465,177 B1 | 10/2002 | Hoon et al. |
| 6,534,293 B1 | 3/2003 | Barany et al. |
| 7,351,701 B2 | 4/2008 | Helleday et al. |
| 7,485,707 B2 | 2/2009 | Matvienko et al. |
| 7,732,491 B2 | 6/2010 | Sherman et al. |
| 7,754,684 B2 | 7/2010 | Stewart et al. |
| 7,759,488 B2 | 7/2010 | Xiao et al. |
| 7,759,510 B2 | 7/2010 | Kay et al. |
| 7,858,331 B2 | 12/2010 | D'Andrea et al. |
| 7,868,040 B2 | 1/2011 | Wilson et al. |
| 7,915,280 B2 | 3/2011 | Ferraris et al. |
| 2003/0049613 A1 | 3/2003 | Perucho et al. |
| 2005/0112604 A1 | 5/2005 | Fujimoto et al. |
| 2006/0088870 A1 | 4/2006 | Finkelstein et al. |
| 2007/0004621 A1 | 1/2007 | Shridhar et al. |
| 2007/0070349 A1 | 3/2007 | Harris et al. |
| 2008/0108057 A1 | 5/2008 | Griffith et al. |
| 2009/0081237 A1 | 3/2009 | D'Andrea et al. |
| 2009/0246789 A1 | 10/2009 | Buckhaults et al. |
| 2010/0145894 A1 | 6/2010 | Semizarov et al. |
| 2010/0159466 A1 | 6/2010 | Eng et al. |
| 2012/0015050 A1 | 1/2012 | Abkevich et al. |
| 2013/0281312 A1* | 10/2013 | Richardson .......... C12Q 1/6886 506/9 |
| 2015/0080260 A1* | 3/2015 | Abkevich ............. C12Q 1/6827 506/9 |

FOREIGN PATENT DOCUMENTS

| | | |
|---|---|---|
| WO | 9841531 | 9/1998 |
| WO | 9954498 | 10/1999 |
| WO | 0024933 | 4/2000 |
| WO | 03074723 | 9/2003 |
| WO | 2004042032 | 5/2004 |
| WO | 2006098978 | 9/2006 |
| WO | 2006110855 | 10/2006 |
| WO | 2006116341 | 11/2006 |
| WO | 2006128195 | 11/2006 |
| WO | 2007035893 | 3/2007 |
| WO | 2009033178 | 3/2009 |
| WO | 2009073869 | 6/2009 |
| WO | 2009148528 | 12/2009 |
| WO | 2010051318 | 5/2010 |
| WO | 2011048495 | 4/2011 |
| WO | 2011106541 | 9/2011 |
| WO | 2011160063 | 12/2011 |
| WO | 2012019000 | 2/2012 |
| WO | 2012027224 | 3/2012 |
| WO | 2013130347 | 9/2013 |
| WO | 2013182645 | 12/2013 |

OTHER PUBLICATIONS

Walsh, C.S. et al. Clin Cancer Res 14(23):7645 (Dec. 1, 2008).*

Santana-Davila, R. et al. Journal of Hematology & Oncology 3:42 (Oct. 27, 2010).*

Al-Mulla et al., "Metastatic recurrence of early-stage colorectal cancer is linked to loss of heterozygosity on chromosomes 4 and 14q" Journal of Clinical Pathology, vol. 59, No. 6, pp. 624-630 (2006).

Gorringe et al. "Are there any more ovarian tumor suppressor genes? A new perspective using ultra high-resoution copy number and loss of heterozygosity analysis", Genes Chromosomes & Cancer, John Wiley & Sons, Inc, US, vol. 48, No. 10, Oct. 1, 2009, pp. 931-942, XP002703162, ISSN: 1045-2257, DOI: 10.1002/GCC.20694 [retrieved on Jul. 14, 2009] *abstract* *p. 932, col. 2, paragraph 2-paragraph3*.

Ko et al., "Frequent loss of heterozygosity on multiple chromosomes in Chinese esophageal squamous cell carcinomas" Cancer Letters, vol. 170, No. 2, pp. 131-138 (2001).

Osborne et al., "A genome-wide map showing common regions of loss of heterozygosity/allelic imbalance in breast cancer", Cancer Research, vol. 60, No. 14, pp. 3706-3712 (2000).

Silva et al., "Loss of heterozygosity in BRCA1 and BRCA2 markers and high-grade malignancy in breast cancer," Breast Cancer Res. & Treatment, Jan. 1999, vol. 53, No. 1, pp. 9-17.

Murayama-Hosokawa, S. et al., "Genome-wide single-nucleotide polymorphism arrays in endometrial carcinomas associate extensive chromosomal instability with poor prognosis and unveil frequent chromosomal imbalances involved in the PI3-kinase pathway," Oncogene, Apr. 1, 2010, vol. 29, No. 13, pp. 1897-1908.

Nannya et al. "A Robust Algorithm for Copy Number Detection Using High-Density Oligonucleotide Single Nucleotide Polymorphism Genotyping Arrays", Cancer Research, American Association for Cancer Research, US, vol. 65, No. 14, Jul. 14, 2005, pp. 6071-6079.

Narayan et al; Frequent promoter of methylation of CDH1,DAPK,RARB, and HIC1 genes in carcinoma of cervix uteri: its relationship to clinical outcome; Mol Cancer; 2003;2:24, 12 pages.

Norquist et al; Secondary somatic mutations restoring BRCA1/2 predict chemotherapy resistance in hereditary ovarian carcinomas; J Clin Oncol;2011; 29(22): 3008-3015.

Novak Urban et al: "A high-resolution allelotype of B-cell chronic lymphocytic leukemia (B-CLL)", Blood, American Society of Hematology, US, vol. 100, No. 5, Sep. 1, 2002, pp. 1787-1794.

Ogston et al., Breast. 2(5):320-7 (2003). "A new histological grading system to assess response of breast cancers to primary chemotherapy, prognostic significance and survival."

O'Shaugnessy et al; Iniparib plus chemotherapy in metastatic triple-negative breast cancer; N Engl J Med; 2011; 364(3):205-214.

Ott et al., Clinical Cancer Research, The American Association for Cancer Research, US, 9(6):2307-2315 (2003). "Chromosomal Instability rather than p53 mutation is associated with response to neoadjuvant cisplatin-based chemotherapy in gastric carcinoma".

Patel et al., "Failure of Iniparib to Inhibit Poly(ADP-Ribose) Polymerase in Vitro," Clin Cancer Res, Mar. 2012, 1655-1662.

Peng et al., "Genome-wide transcriptome profiling of homologous recombination DNA repair," Nature Communications, 2014, 1-11.

Penning et al., "Discovery and SAR of 2-(1-propylpiperidin-4-yl)-1H-benzimidazole-4-carboxaminde: A potent inhibitor of poly(ADP-ribose) polymerase (PARP) for the treatment of cancer", Bioorganic & Medicinal Chemistry, Pergamon, GB, vol. 16, No. 14, Jul. 15, 2008, pp. 6965-6975.

Pfeifer et al. "Genome-wide analysis of DNA copy number changes and LOH in CLL using high-density SNP arrays", Blood, vol. 109, No. 3, Oct. 5, 2006, pp. 1202-1210.

Popova et al. "Genome Alteration Print (GAP): a tool to visualize and mine complex cancer genomic profiles obtained by SNP arrays", Genome Biology, Biomed Central Ltd., London, GB, vol. 10, No. 11, Nov. 11, 2009, p. R128.

Puliti et al., Mutat Res. 686(1-2):74-83 (2010). "Low-copy repeats on chromosome 22q11.2 show replication timing switches, DNA flexibility peaks and stress inducible asynchrony, sharing instability features with fragile sites."

(56) References Cited

OTHER PUBLICATIONS

R. Mei: "Genome-wide detection of Allelic Imbalance Using Human SNPs and High-density DNA arrays", Genome Research, vol. 10, No. 8, Aug. 1, 2000, pp. 1126-1137.
Rakha et al. "Basal-like breast cancer: a critical review", Journal of Clinical Oncology, American Society of Clinical Oncology, US, vol. 26, No. 14, May 20, 2008, pp. 2568-2581.
Ramirez, C. et al., "Loss of 1p, 19q, and 10q heterozygosity prospectively predicts prognosis of oligodendroglial tumors—towards individualized tumor treatment?" Neuro. Oncol., May 2010, vol. 12, No. 5, pp. 490-499.
Richard et al., Micro Biol Rev. 72(4):686-727 (2008). "Comparitive genomics and molecular dynamics of DNA repeats in eukaryotes."
Richardson et al., Cancer Cell 9:121-132 (2006). "X chromosomal abnormalities in basal-like human breast cancer."
Ryan et al, 2009 ASCO Annual Meeting, http://meetinglibrary.asco.org/content/34135-65, (2009). "Neoadjuvant cisplatin and bevacizumab in triple negative breast cancer (TNBC): Safety and efficacy."
Sakai et al; Functional restoration of BRCA2 protein by secondary BRCA2 mutations in BRCA2-mutated ovarian carcinoma; Cancer Res; 2009; 69(16):6381-6386.
Sakai et al; Secondary mutations as a mechanism of cisplatin resistance in BRCA2-mutated cancers; Nature; 2008; 451(7182):1116-1120.
Samouelian et al., Cancer Chemother Pharmacol. 54(6): 497-504 (2004). "Chemosensitivity and radiosensitivity profiles of four new human epithelial ovarian cancer cell lines exhibiting genetic alterations in BRCA2, TGFbetaRII, KRAS2, TP53 and/or CDNK2A."
Schouten et al., "Challengers in the Use of DNA Repair Deficiency as a Biomarker in Breast Cancer," Journal of Clinical Oncology, 2015, 33(17): 1867-1869.
Schwartz et al., Genes Development 19:2715-2726 (2005). "Homologous recombination and nonhomologous end-joining repair pathways regulate fragile site stability."
Sebat et al., Science. 305(5683):525-8 (2004). "Large-scale copy number polymorphism in the human genome."
Silver et al. "Efficacy of Neoadjuvant Cisplatin in Triple-Negative Breast Cancer", J. Clin. Oncol. vol. 28, 2010, pp. 1145-1153.
Smid et al. "Patterns and incidence of chromosomal instability and their prognostic relevance in breast cancer subtypes", Breast Cancer Research and Treatment, Kluwer Academic Publishers, BO, vol. 128, No. 1, Jul. 15, 2010, pp. 23-30.
Sorlie et al., PNAS 100(14):8418-8423 (2003). "Repeated observation of breast tumor subtypes in independent gene expression data set."
Stankiewcz et al., Am J Hum Genet. 72(5):1101-16 (2003). "Genome architecture catalyzes nonrecurrent chromosomal rearrangements."
Stefansson et al; Genomic profiling of breast tumours in relation to BRCA abnormalities and phenotypes; Breast Cancer Res; 2009; 11(4):R47, 14 pages.
Swisher et al. Cancer Res. 68(8):2581-6 (2008). "Secondary BRCA1 mutations in BRCA1-mutated ovarian carcinomas with platinum resistance."
Takahashi, Clinical Cancer Research, 13(1): 111-120 (2007). "Clonal and Parallel Evolution of Primary Lung Cancers and Their Metastases Revealed by Molecular Dissection of Cancer Cells."
Tan et al; 'BRCAness' syndrome in ovarian cancer: a case-control study describing the clinical features and outcome of patients with epithelial ovarian cancer associated with BRCA1 and BRCA2 mutations; J Clin Oncol; 2008;26 (34):5530-5536.
Tassone et al., Br J Cancer. 88(8): 1285-91 (2003). "BRCA1 expression modulates chemosensitivity of BRCA1-defective HCC1937 human breast cancer cells."
Teh M-T et al.: "Genomewide Single Nucleotide Polymorphism Microarray Mapping in Basal Cell Carcinomas Unveils Uniparental Disomy as a Key Somatic Event", Cancer Research, vol. 65, No. 19, Oct. 1, 2005, pp. 8597-8603.
Telli et al., "Phase II Study of Gemcitabine, Carboplatin, and Iniparib as Neoadjuvan Therapy for Triple-Negative and BRCA1/2 Mutation-Associated Breast Cancer With Assessment of a Tumor-Based Measure of Genomic Instability: PrECOG0105," J Clin Oncol, 2015, 1-7.
The Cancer Genome Atlas Research Network; Integrated genomic analyses of ovarian carcinoma; Nature; 2011; 474(7353):609-615.
Tseng, R. C. et al., Genomewide loss of heterozygosity and its clinical associations in non-small cell lung cancer, Int. J. Cancer, Nov. 1, 2005, vol. 117, No. 2, pp. 241-247.
Turner et al., Oncogene 26:2126-2132 (2007). "BRCA1 dysfunction in sporadic basal-like breast cancer."
Valeri A et al.: "High frequency of allelic losses in high-grade prostate cancer is associated with biochemical progression after radical prostatctomy", Urologic Oncology, Elsevier, New York, NY, US, vol. 23, No. 2, Mar. 1, 2005, pp. 87-92.
Van Loo et al., PNAS 107(39):16910-16915 (2010). "Allele-specific copy number analysis of tumors."
Volchenboum et al. "Comparison of Primary Neuroblastoma Tumors and Derivative Early-Passage Cell Lines Using Genome-Wide Single Nucleotide Polymorphism Array Analysis", Cancer Research, vol. 69, No. 10, May 12, 2009.
Vollenbergh et al. "Genomic instability in breast and ovarian cancers: translation into clinical predictive biomarkers", CMLS Cellular and Molecular Life Science, Birkhauser-Verlag, BA, vol. 69, No. 2, Sep. 16, 2011, pp. 223-245.
Vrieling et al., Nature Genetics 28:101-102 (2001). "Mitotic maneuvers in the light."
Wang et al., Cancer Research 64:64-71 (2004). "Loss of heterozygosity and it's correlation with expression in profiles in subclasses of invasive breast cancers."
Wang et al., Genome Biology 8R246 (2007). "Analysis of molecular inversion probe performance for allele copy number determination."
Wilcox et al; High-resolution methylation analysis of the BRCA1 promoter in ovarian tumors; Cancer Genet Cytogenet; 2005; 159(2): 114-122.
Wilcoxen et al., "Homologous recombination deficiency (HRD) score enriches for niraparib sensitive high grade ovarian tumors," Supplemental Abstract, 2015, 1 page.
Wilcoxen et al., "Use of homologous recombination deficiency (HRD) score to enrich for niraparib sensitive high grade ovarian tumors," J Clin Oncol, 2015, Supplemental Abstract: 5532, 2 pages.
Xiao et al., "The XIST Noncoding RNA Functions Independently of BRCA1 in X Inactivation," Cell, Mar. 2007, 128:977-989.
Xu et al., Molecular Cell 3:389-395 (1999). "Centrosome amplification and a defective G2-M cell cycle checkpoint induce genetic instability in BRCA1 Exon 11 Isoform-deficient cells."
Yang et al., Cancer Research 61:348-354 (2001). "Reconstitution of caspase 3 sensitizes MCF-7 Breast Cancer to Doxoubicin- and Etoposide-induced apoptsis."
Abkevich et al. "Patterns of genomic loss of heterozygosity predict homologous recombination repair defects in epithelial ovarian cancer", British Journal of Cancer, vol. 107, No. 10, Oct. 9, 2012, pp. 1776-1782.
Abkevich et al. "Supplemental Material: Table S1: Validation of copy number determinations by Real Time PCR SNP ID Adjacent Gene Sample Copy Number by Real-Time PCR Copy Number by CCNT SNP A",—1712744 CDKN2A HF505 0.010 0.47 HF1382 0.14 0, Oct. 1, 2006, pp. 5-1713144, XP055085899, Retrieved from the Internet: URL: http://cancerres.aacrjournals.org/content/suppl/2006/10/04/66.19.9428.DC2/Supplementary_Tables_1-5.pdf [retrieved on Oct. 29, 2013].
Argos et al. "Genomewide scan for loss of heterozygosity and chromosomal amplification in breast carcinoma using single-nucleotide polymorphism arrays", Cancer Genetics and Cytogenetics, Vo. 182, No. 2, Apr. 15, 2008.
Arlt et al., Molecular and Cellular Biology, 24(15):6701-6709 (2004). "BRCA1 is required for common-fragile-site stability via its G2M checkpoint function."
Ashworth et al. "A Synthetic Lethal Therapeutic Approach: Poly(ADP) Ribose Polymerase Inhibitors for the Treatment of Cancers Deficient in DNA Double-Strand Break Repair", Journal of Clinical Oncology, vol. 26, No. 22, Aug. 1, 2008, pp. 3785-3790.
Bamford et al., British Journal of Cancer 91:355-358 (2004). "The COSMIC (Catalogue of Somatic Mutations in Cancer) database and website."

(56) References Cited

OTHER PUBLICATIONS

Beder L B et al.: "Genome-wide analyses on loss of heterozygosity in head and neck squamous cell carcinomas", Laboratory Investigation, vol. 83, No. 1, 2003, pp. 99-105.
Bell et al., Nature 474:609-615 (2011). "Integrated genomic analyses of ovarian carcinoma."
Bengtsson et al., Bioinformatics 25(17):2149-2156 (2009). "A single-array preprocessing methods for estimating full-resolution raw copy numbers from all affymetrix genotyping arrays including genomeWideSNP 5 &6."
Bentsson et al., BMC Bioinformatics 11:245-262 (2010). "TumorBoost: Normalization of allele-specific tumor copy numbers from a single pair of tumor-normal genotyping microarrays."
Beroukhim et al. "Inferring Loss-of-Heterozygosity from Unpaired Tumors Using High-Density Oligonucleotide SNP Arrays", Bioinformatics, vol. 19, No. 5, Jan. 1, 2006, p. 2397.
Birbak et al., Cancer Research, 72(8):1, (2012). Abstract 4823: copy number gain and increased expression of BLM and FANCI is associated with sensitivity to genotoxic chemotherapy in triple negative breast and serious ovarian cancer.
Birkbak et al. "Telomeric allelic imbalance indicates defective DNA repair and sensitivity to DNA-damaging agents"; Cancer Discov; 2012; 2(4): 366-375.
Bouwman et al., Nature Structural and Molecular Biology 17(6):688-696 (2010). "53BP1 loss rescues BRCA1 deficiency and is associated with triple-negative and BRCA-mutated breast cancers."
Bryant et al. "Specific killing of BRCA2-deficient tumours with inhibitors of poly(ADP-ribose) polmerase"; Nature; 2005; 434(7035):913-917.
Buch H N et al.: "Prediction of recurrence of nonfunctioning pituitary tumours by loss of heterozygosity analysis", Clinical Endocrinology, vol. 61, 2004, p. 19-22.
Bunting et al., Cell 141(2)243-54 (2010). "53BP1 inhibits homologous recombination in Brca1-deficient cells by blocking resection of DNA breaks."
Burger et al. Drug Resistance Updates 14:22-34 (2011). "Drug transporters of platinum-based anticancer agents and their clinical significance."
Byrski et al., Breast Cancer Res Treat. 115(2):359-63. (2009). "Response to neoadjuvant therapy with cisplatin in BRCA1-positive breast cancer patients."
Calvert et al. "245 Invited PARP inhibitors in cancer treatment", European Journal of Cancer. Supplement, Pergamon, Oxford, GB, vol. 6, No. 12, Oct. 1, 2008, p. 80.
Cass et al., Cancer 97(9):2187-95 (2002). "Improved survival in women with BRCA-associated ovarian carcinoma."
Cerbinskaite et al; Defective homologous recombination in human cancers; Cancer Treat Rev; 2012; Epub 2011; 38(2): 89-100.
Cha et al., Science; 297(5581):602-6 (2002). "ATR homolog Mec1 promotes fork progression, thus averting breaks in replication slow zones."
Chang et al., "Assessment of plasma DNA levels, allelic imbalance, and CA 125 as diagnostic tests for cancer", Journal of the National Cancer Institute, vol. 94, No. 22, pp. 1697-1703 (2002).
Cheung T H et al.: "Clinicopathologic significance of loss of heterozygosity on chromosome 1 in cervical cancer" Gynecologic Oncology, Academic Press, London, GB, vol. 96, No. 2, Feb. 1, 2005, pp. 510-515.
Choi et al., "Genetic Classification of Colorectal Cancer Based on Chromosomal Loss and Microsatellite Instability Predicts Survival," Clinical Cancer Research, Jul. 2002, 8: 2311-2322.
Dann et al; BRCA1/2 mutations and expression: response to platinum chemotherapy in patients with advanced stage epithelial ovarian cancer; Gynecol Oncol; 2012;125(3):677-682.
De Soto et al. "The inhibition and treatment of breast cancer with poly (ADP-ribose) polymerase (PARP-1) inhibitors", International Journal of Biological Sciences, Ivyspring International Publisher, AU, vol. 2, No. 4, Jun. 10, 2006, pp. 179-185.
Edwards et al; Resistance to therapy caused by intragenic deletion in BRCA2; Nature; 2008; 451(7182):1111-1115.
Etemadmoghadam et al: "Integrated genome-wide DNA copy number and expression analysis identifies distinct mechanisms of primary chemoresistance in ovarian carcinomas", Clinical Cancer Research, The American Association for Cancer Research, US, vol. 15, No. 4, Feb. 15, 2009, pp. 1417-1427.
European Communication Response for application 11757992.0, dated Mar. 21, 2014.
European Communication Response for application 11757992.0, dated Dec. 9, 2014.
European Communication Response for application 11796544.2, dated Sep. 28, 2015.
European Communication Response, for application 11796544.2, dated Aug. 3, 2015.
European Communication, for application 11757992.0, dated Aug. 5, 2014.
European Communication, for application 11757992.0, dated Dec. 10, 2013.
European Communication, for application 11796554.2, dated May 11, 2015.
European Communication, for application 11796554.2, dated Sep. 11, 2015.
European Intention to Grant, for application 11757992.0, dated Jul. 28, 2015.
Extended European Search Report, app. No. 12801070.9, dated Dec. 3, 2014.
Extended European Search Report, for application EP11796544.2, dated Nov. 18, 2013.
Extended European Search Report, from Application EP11748075.6, dated Jul. 29, 2013.
Extended European Search Report, from Application EP12860530.0, dated Jul. 24, 2015.
Fang et al. "Genomic Differences Between Estrogen Receptor (ER)-Positive and ER-Negative Human Breast Carcinoma Identified by Single Nucleotide Polymorphism Array Comparative Genome Hybridization Analysis", Cancer, vol. 117, No. 10, May 2011.
Farmer et al; Targeting DNA repair defect in BRCA mutant cells as a therapeutic strategy; Nature; 2005; 434(7035):917-921.
Feltmate C M et al.: "Whole-genome allelotyping identified distinct loss-of-heterozygosity patterns in mucinous ovarian and appendiceal carcinomas", Clinical Cancer Research, vol. 11, No. 21, Nov. 1, 2005, pp. 7651-7657.
Ferreira et al: "Array CGH and gene-expression profiling reveals distinct genomic instability patterns associated with DNA repair and cell-cycle checkpoint pathways in Ewing's sarcoma", Oncogene, vol. 27, No. 14, Mar. 27, 2008, pp. 2084-2090.
Filopanti et al., "Loss of heterozygosity at the SS receptor type 5 locus in human GH- and TSH-secreting pituitary adenomas," J. Endocrinol. Invest., Nov. 2004, vol. 27, No. 10, pp. 937-942.
Franko, J. et al., "Loss of heterozygosity predicts poor survival after resection of pancreatic adenocarcinoma," J. Gastrointest. Surg., Oct. 2008, vol. 12, No. 10, pp. 1664-1723.
Friedenson; BRCA1 and BRCA2 pathways and the risk of cancers other than breast or ovarian; MedGenMed; 2005; 7(2):60, 25 pages.
Gelmon et al; Olaparib in patients with recurrent high-grade serous or poorly differentiated ovarian carcinoma or triple-negative breast cancer: a phase 2, multicentre, open-label, non-randomised study; Lancet Oncol; 2011;12(9):852-861.
Goransson et al. "Quantification of Normal Cell Fraction and Copy Number Neutral LOH in Clinical Lung Cancer Samples Using SNP Array Data", PLOS ONE, vol. 4, No. 6, Jun. 26, 2009, p. e6057.
Graziani et al. "PARP-1 inhibition to treat cancer, ischemia, inflammation", Pharmacological Research, Academic Press, London, GB, vol. 52, No. 1, Jul. 1, 2005, pp. 1-4.
Gudmundsdottir et al. "The roles of BRCA1 and BRCA2 and associated proteins in the maintenance of genomic stability", Oncogene, vol. 25, No. 43, Sep. 25, 2006, pp. 5864-5874.
Gunnarsson et al. "Large but not small copy-number alterations correlate to high-risk genomic aberrations and survival in chronic lymphocytic lukemia: a high-resolution genomic screening of newly diagnosed patients", Lukemia, vol. 24, No. 1, Jan. 1, 2010, pp. 211-215.
Hampton et al., "Simultaneous assessment of loss of heterozygosity at multiple microsatellite loci using semi-automated fluorescence-

(56) References Cited

OTHER PUBLICATIONS based detection: Subregional mapping of chromosome 4 in cervical carcinoma," PNAS, Jun. 1996, vol. 93, No. 13, pp. 6704-6709.
Hastings et al., Nat Rev. Genetic 10(8): 551-564 (2009). "Mechanisms of change in gene copy number."
Hastings et al., PLOS Genetics 5(1):e1000327 (2009). "A microhomology-mediated break-induced replication model for the origin of human copy number variation."
Heinsohn, S. et al., "Determination of the prognostic value of loss of heterozygosity at the retinoblastoma gene in osteosarcoma," Int. J. Oncol., May 2007, vol. 30, No. 5, pp. 1205-1214.
Heiser et al., Proc Natl Acad Sci U S A. 109(8):2724-9 (2012). "Subtype and pathway specific responses to anticancer compounds in breast cancer."
Hendricks et al. "'Recombomice': The past, present, and future of recombination-detection in mice" DNA Repair, vol. 3, No. 10, Oct. 5, 2004.
Hennessy et al; Somatic mutations in BRCA 1 and BRCA2 could expand the number of patients that benefit from poly (ADP ribose) polymerase inhibitors in ovarian cancer; J Clin Oncol; 2010; 28(22):3570-3576.
Holstege et al; BRCA1-mutated and basal-like breast cancers have similar aCGH profiles and a high incidence of protein truncating TP53 mutations; BMC Cancer; 2010; 10:654, 15 pages.
Iafrate et al., Nat Genet. 36(9): 949-51. (2004). "Detection of large-scale variation in the human genome."
International Preliminary Report on Patentability, app. No. PCT/US2012/071380, dated Jun. 24, 2014.
International Search Report, for application PCT/EP2013/061707, dated Jul. 29, 2013.
International Search Report, for application PCT/EP2014/076786, dated Feb. 27, 2015.
International Search Report, for application PCT/US2011/026098, dated Nov. 25, 2011.
International Search Report, for application PCT/US2011/040953, dated Feb. 27, 2012.
International Search Report, for application PCT/US2011/048427, dated Nov. 7, 2011.
International Search Report, for application PCT/US2012/042668, dated Feb. 1, 2013.
International Search Report, for application PCT/US2012/071380, dated Apr. 12, 2013.
International Search Report, for application PCT/US2013/027295, dated Jun. 10, 2013.
Isakoff et al., "TBCRC009: A Multicenter Phase II Clinical Trial of Platinum Monotherapy With Biomarker Assessment in Metastatic Triple-Negative Breast Cancer," J Clin Oncol, 2015, 1-8.
Janne et al. "High-resolution single-nucleotide polymorphism array and clustering analysis of loss of heterozygosity in human lung cancer cell lines", Oncogene, vol. 23, No. 15, Mar. 29, 2004, pp. 2716-2726.
Joosse et al. "Prediction of BRCA-1-association in hereditary non-BRCA1/2 breast carcinomas with array-CGH", Breast Cancer Research and Treatment, Kluwer Academic Publishers, BO, vol. 116, No. 3, Aug. 14, 2008, pp. 479-489.
Juul et al., Cancer Research, 69(24): 509S-510S (2009). "A Genomic Profile Derived Summary Measure of Chromosomal Breakpoints Predicts Response to Treatment with the DNA-Damaging Agent Cisplatin."
Kaklamani et al., "Phase II neoadjuvant clinical trial of carboplatin and eribulin in women with triple negative early-stage breast cancer (NCT01372579)," Breast Cancer Res Treat, 2015, 151:629-638.
Kalb et al., Genome Dyn. 1:218-42. (2006). "Fanconi anemia: causes and consequences of genetic instability."
Kerangueven, F. et al. Cancer Research 57, 5469-5475 (1997).
Kolomietz et al., Genes Ghromosomes Cancer. 35(2):97-112 (2002). "The role of Alu repeat clusters as mediators of recurrent chromosomal aberrations in tumors."

Kujawski et al. "Genomic complexity identifies patients with aggressive chronic lymphocytic lukemia", Blood, vol. 112, No. 5, Sep. 1, 2008, pp. 1993-2003.
Lakhani et al., Clin Cancer Res. 11(14)5175-80 (2005). "Prediction of BRCA1 status in patients with breast cancer using estrogen receptor and basal phenotype."
Lemeta et al., "Loss of Heterozygosity at 6q is Frequent and Concurrent with 3p Loss in Sporadic and Familial Capillary Hemangioblastomas," J. Neuropathol. Exp. Neurol., Oct. 2004, vol. 63, No. 10, pp. 1072-1079.
Leunen et al. "Recurrent Copy number alterations in BRCA1-mutated ovarian tumors alter biological pathways", Human Mutation, vol. 30, n. 12, Dec. 1, 2009, pp. 1693-1702.
Li et al., BMC Bioinformatics 12:474 (2011). "Jetset: selecting the optimal microarray probe set to represent a gene."
Li et al., Nature Medicine 15(2):214-219 (2010). "Amplification of LAPTM4B and YWHAZ contributes to chemotherapy resistance and recurrence of breast cancer."
Lin et al. "Integrated analysis of copy number alterations and loss of heterozygosity in human pancreatic cancer using a high-resolution, single nucleotide polymorphism array", Oncology, vol. 75, No. 1-2, Sep. 1, 2008.
Loveday et al; Germline mutations in RAD51D confer susceptibility to ovarian cancer; Nat Genet; 2011; 43(9):879-882.
Luo et al., Nat Genet. 26(4):424-9 (2000). "Cancer predisposition caused by elevated mitotic recombination in Bloom mice."
Maeck et al. "Genetics instability in myelodysplastic syndrome: Detection of microsatellite instability and loss of heterozygosity in bone marrow samples with karyotype alterations" British Journal of Haematology, vol. 109, No. 4, Jun. 2000.
Marsit et al; Inactivation of the Fanconi anemia/BRCA pathway in lung and oral cancers: implications for treatment and survival; Oncogene; 2004; 23(4):1000-1004.
Mateo et al., "Appraising iniparib, the PARP inhibitor that never was—what must we learn?," Nature, Dec. 2013, 10: 688-696.
Matsumoto et al., "Allelic imbalance at 1P36 may predict prognosis of chemoradiation therapy for bladder preservation in patients with invasive bladder cancer", British Journal of Cancer, vol. 91, No. 6, pp. 1025-1031 (2004).
McVean et al., Philos Trans R Soc Lond B Biol Sci. 365(1544):1213-8 (2010). "What drived recombination hotspots to repeat DNA in humans?"
Meadows et al. "Genome-wide analysis of loss of heterozygosity and copy number amplification in uterine leiomyomas using the 100K single nucleotide polymorphism array", Experimental and Molecular Pathology, vol. 91, No. 1, Apr. 8, 2011, pp. 434-439.
Medri, L. et al. Modern Pathology 2003;16(11):1067-1075.
Meindl et al; Germline mutations in breast and ovarian cancer pedigrees establish RAD51C as a human cancer susceptibility gene; Nat Genet; 2010; 42(5):410-414.
Mendes-Pereira et al; Synthetic lethal targeting of PTEN mutant cells with PARP inhibitors; EMBO Mol Med; 2009;1(6-7): 315-322.
Mukhopadhyay et al., "Clinicopathological Features of Homologous Recombination-Deficient Epithelial Ovarian Cancers: Sensitivity to PARP Inhibitors, Platinum, and Survival," Cancer Research, 2012, 5675-5682.
Carr J. et al. Cancer Genetics and Cytogenetics 172 (2007) 127-138.
De Preter et al. Cancer Letters 197 (2003) 53-61.
European Communication Response, for application 11796544.2, dated Feb. 1, 2016.
European Communication Response, for application 12860530.0, dated Feb. 10, 2016.
European Communication, for application 11796544.2, dated Jan. 20, 2016.
European Communication, for application 12801070.9, dated Apr. 1, 2016.
European Intention to Grant, for application 11796544.2, dated Mar. 31, 2016.
Extended European Search Report, for application EP15189527.3, dated Mar. 31, 2016.
Fontanillas et al., "Key considerations for measuring allelic expression on a genomic scale using high-throughput sequencing", Molecular Ecology, vol. 19, No. 1, Mar. 1, 2010, pp. 212-227.

(56) References Cited

OTHER PUBLICATIONS

Heap et al., "Genome-wide analysis of allelic expression imbalance in human primary cells by high-throughput transcriptome resequencing", Human Molecular Genetics, vol. 19, No. 1, Jan. 1, 2010, pp. 122-134.

International Search Report, for application PCT/US2015/045561, dated Nov. 9, 2015.

Li C. et al. BMC Bioinformatics 2008, 9:204, pp. 1-16.

Sang-Wook et al. "Genetic classification of colorectal cancer based on chromosomal loss and microsatellite instability predicts survival", Clinical Cancer Research, The American Association for Cancer Research, US, vol. 8, No. 7, Jul. 1, 2002, pp. 2311-2322.

Silver et al., Cell 128(5):991-1005 (2007). "Further evidence for BRCA1 communication with the inactive X chromosome."

Soule H.D. et al. Cancer Research, 50. 6075-6086. Sep. 15, 1990.

Tai et al., "High-Throughput Loss-of-Heterozygosity Study of Chromosome 3p in Lung Cancer Using Single-Nucleotide Polymorphism Markers", Cancer Research, vol. 66, No. 8, Apr. 15, 2006, pp. 4133-4138.

Yaris N. et al. The Turkish Journal of Pediatrics 2004; 46: 182-185.

Patocs, A. et al., "Breast-cancer stromal cells with TP53 mutations and nodal metastases", N. Engl. J. Med., 2007, vol. 357, pp. 2543-2551.

Japanese Patent Application Kohyo Publication No. (JP-A) 2008-538496 (unexamined Japanese national phase publication corresponding to a non-Japanese international publication), (considered English language portions).

Zhao, Q. et al., "Systematic detection of putative tumor suppressor genes through the combined use of exome and transcriptome sequencing", Genome Biol., 2010, vol. 11: R114, pp. 1-14.

Johansson, P. et al., "Abstract 4833: A genomic portrait of tumor progression using next-generation sequencing", Cancer Res., Apr. 15, 2011, vol. 71, p. 4833.

* cited by examiner

| Status | Number of Samples | Percent |
|---|---|---|
| BRCA Deficient | 44 | 33% |
| HDR Deficient/BRCA Intact | 18 | 13% |
| HDR Intact | 72 | 54% |
| Total | 134 | 100% |

FIGURE 9

METHODS AND MATERIALS FOR ASSESSING LOSS OF HETEROZYGOSITY

CROSS-REFERENCE TO RELATED APPLICATIONS

The present application is a continuation application of International Application Serial No. PCT/US2012/071380, filed 21 Dec. 2012 and published 27 Jun. 2013 as WO2013/096843. The present application and International Serial No. PCT/US2012/071380 are related to and claim the priority benefit of U.S. Provisional Patent Application Ser. No. 61/578,713 filed Dec. 21, 2011 and U.S. Provisional Patent Application Ser. No. 61/654,402 filed Jun. 1, 2012, the entire contents of which are hereby incorporated by reference.

BACKGROUND

1. Technical Field

This document relates to methods and materials involved in assessing samples (e.g., cancer cells) for the presence of a loss of heterozygosity (LOH) signature. For example, this document provides methods and materials for determining whether or not a cell (e.g., a cancer cell) contains an LOH signature. This document also provides materials and methods for identifying cells (e.g., cancer cells) having a deficiency in homology directed repair (HDR) as well as materials and methods for identifying cancer patients likely to respond to a particular cancer treatment regimen. Throughout this document, unless indicated otherwise, HDR deficiency and HRD (homologous repair deficiency) are used synonymously.

2. Background Information

Cancer is a serious public health problem, with 562,340 people in the United States of America dying of cancer in 2009 alone. *American Cancer Society, Cancer Facts & Figures* 2009 (available at American Cancer Society website). One of the primary challenges in cancer treatment is discovering relevant, clinically useful characteristics of a patient's own cancer and then, based on these characteristics, administering a treatment plan best suited to the patient's cancer. While strides have been made in this field of personalized medicine, there is still a significant need for better molecular diagnostic tools to characterize patients' cancers.

SUMMARY

In general, one aspect of this invention features a method for assessing LOH in a cancer cell or genomic DNA thereof. In some embodiments, the method comprises, or consists essentially of, (a) detecting, in a cancer cell or genomic DNA derived therefrom, LOH regions in at least one pair of human chromosomes of the cancer cell (e.g., any pair of human chromosomes other than a human X/Y sex chromosome pair); and (b) determining the number and size (e.g., length) of said LOH regions. In some embodiments, LOH regions are analyzed in a number of chromosome pairs that are representative of the entire genome (e.g., enough chromosomes are analyzed such that the number and size of LOH regions are expected to be representative of the number and size of LOH regions across the genome). In some embodiments, the method further comprises determining the total number of LOH regions that are longer than about 1.5, 5, 12, 13, 14, 15, 16, 17 or more (preferably 14, 15, 16 or more, more preferably 15 or more) megabases but shorter than the entire length of the respective chromosome which the LOH region is located within (Indicator LOH Regions). Alternatively or additionally, the total combined length of such Indicator LOH Regions is determined. In some specific embodiments, if that total number of Indicator LOH Regions or total combined length of Indicator LOH Regions is equal to or greater than a predetermined reference number, then said cancer cell or genomic DNA or a patient having said cancer cell or genomic DNA is identified as having an HDR-deficiency LOH signature.

An alternative method for assessing LOH in a cancer cell or genomic DNA thereof is also provided which comprises, or consists essentially of, (a) detecting, in a cancer cell or genomic DNA derived therefrom, LOH regions in at least one pair of human chromosomes of the cancer cell, wherein the at least one pair of human chromosomes is not a human X/Y sex chromosome pair; and (b) determining the total number and/or combined length of LOH regions, in the at least one pair of human chromosomes, that are longer than a first length but shorter than the length of the whole chromosome containing the LOH region, wherein the first length is about 1.5 or more (or 5, 10, 13, 14, 15, 16 or more, preferably 15 or more) megabases. In some specific embodiments, if that total number or combined length is equal to or greater than a predetermined reference number, then said cancer cell or genomic DNA or a patient having said cancer cell or genomic DNA is identified as having an HDR-deficiency LOH signature.

In another aspect, the present invention provides a method of predicting the status of BRCA1 and BRCA2 genes in a cancer cell. The method comprises, or consists essentially of, determining, in the cancer cell, the total number and/or combined length of LOH regions in at least one pair of human chromosomes of the cancer cell that are longer than a first length but shorter than the length of the whole chromosome containing the LOH region, wherein the at least one pair of human chromosomes is not a human X/Y sex chromosome pair, wherein the first length is about 1.5 or more (or 5, 10 or more, preferably about 15 or more) megabases; and correlating the total number or combined length that is greater than a reference number with an increased likelihood of a deficiency in the BRCA1 or BRCA2 gene.

In another aspect, this invention provides a method of predicting the status of HDR in a cancer cell. The method comprises, or consists essentially of, determining, in the cancer cell, the total number and/or combined length of LOH regions in at least one pair of human chromosomes of the cancer cell that are longer than a first length but shorter than the length of the whole chromosome containing the LOH region, wherein the at least one pair of human chromosomes is not a human X/Y sex chromosome pair, wherein the first length is about 1.5 or more (or 5, 10 or more, preferably about 15 or more) megabases; and correlating the total number or combined length that is greater than a reference number with an increased likelihood of a deficiency in HDR.

In another aspect, this invention provides a method of predicting a cancer patient's response to a cancer treatment regimen comprising a DNA damaging agent, an anthracycline, a topoisomerase I inhibitor, radiation, and/or a PARP inhibitor. The method comprises, or consists essentially of, determining, in a cancer cell from the cancer patient, the number and/or combined length of LOH regions in at least one pair of human chromosomes of a cancer cell of the cancer patient that are longer than a first length but shorter than the length of the whole chromosome containing the LOH region, wherein the at least one pair of human chromosomes is not a human X/Y sex chromosome pair, wherein the first length is about 1.5 or more (or 5, 10 or more, preferably about 15 or more) megabases; and correlating the total number or combined length that is greater than a reference number with an increased likelihood that the cancer patient will respond to the cancer treatment regimen. In some embodiments, the patients are treatment naïve patients.

In another aspect, present invention relates to a method of predicting a cancer patient's response to a treatment regimen. The method comprises, or consists essentially of, determining, in a cancer cell from the cancer patient, the total number and/or combined length of LOH regions in at least one pair of human chromosomes of a cancer cell of the cancer patient that are longer than a first length but shorter than the length of the whole chromosome containing the LOH region, wherein the at least one pair of human chromosomes is not a human X/Y sex chromosome pair, wherein the first length is about 1.5 or more (or 5, 10 or more, preferably about 15 or more) megabases; and correlating the total number or combined length that is greater than a reference number with an increased likelihood that the cancer patient will not respond to a treatment regimen including paclitaxel or docetaxel.

In another aspect, this invention is directed to a method of treating cancer. The method comprises, or consists essentially of, (a) determining, in a cancer cell from a cancer patient or genomic DNA obtained therefrom, the total number and/or combined length of LOH regions in at least one pair of human chromosomes of the cancer cell that are longer than a first length but shorter than the length of the whole chromosome containing the LOH region, wherein the at least one pair of human chromosomes is not a human X/Y sex chromosome pair, wherein the first length is about 1.5 or more (or 5, 10 or more, preferably about 15 or more) megabases; and (b) administering to the cancer patient a cancer treatment regimen comprising one or more drugs chosen from the group consisting of DNA damaging agents, anthracyclines, topoisomerase I inhibitors, and PARP inhibitors, if the total number or combined length of LOH regions is greater than a reference number. In some embodiments, the patients are treatment naïve patients.

In some embodiments of any one or more of the methods described in the preceding six paragraphs, any one or more of the following can be applied as appropriate. The LOH regions can be determined in at least two, five, ten, or 21 pairs of human chromosomes. The cancer cell can be an ovarian, breast, or esophageal cancer cell. The first length can be about 6, 12, or about 15 or more megabases. The reference number can be 6, 7, 8, 9, 10, 11, 12, 13, 14, 15, 16, 17, 18 or 20 or greater. The at least one pair of human chromosomes can exclude human chromosome 17. The DNA damaging agent can be cisplatin, carboplatin, oxalaplatin, or picoplatin, the anthracycline can be epirubincin or doxorubicin, the topoisomerase I inhibitor can be campothecin, topotecan, or irinotecan, or the PARP inhibitor can be iniparib, olaparib or velapirib.

In another aspect, this invention features the use of one or more drugs selected from the group consisting of DNA damaging agents, anthracyclines, topoisomerase I inhibitors, and PARP inhibitors, in the manufacture of a medicament useful for treating a cancer in a patient identified as having a cancer cell determined to have a total of 5, 8, 9, 10, 12, 15, 17, 20 or more Indicator LOH Regions. The Indicator LOH Regions can be determined in at least two, five, ten, or 21 pairs of human chromosomes. The cancer cell can be an ovarian, breast, or esophageal cancer cell. The Indicator LOH Regions can have a length of about 6, 12, or 15 or more megabases. The Indicator LOH Regions can be present on a chromosome other than human chromosome 17. The DNA damaging agent can be a platinum-based chemotherapy drug, the anthracycline can be epirubincin or doxorubicin, the topoisomerase I inhibitor can be campothecin, topotecan, or irinotecan, or the PARP inhibitor can be iniparib, olaparib or velapirib. In some embodiments, the patients are treatment naïve patients.

In another aspect, this invention features the use of a plurality of oligonucleotides capable of hybridizing to a plurality of polymorphic regions of human genomic DNA, in the manufacture of a diagnostic kit useful for determining the total number or combined length of Indicator LOH Regions in at least a chromosome pair of a human cancer cell obtained from a cancer patient, and for detecting (a) an increased likelihood of a deficiency in the BRCA1 or BRCA2 gene in the cancer cell, (b) an increased likelihood of a deficiency in HDR in the cancer cell, or (c) an increased likelihood that the cancer patient will respond to cancer treatment regimen comprising a DNA damaging agent, an anthracycline, a topoisomerase I inhibitor, radiation, or a PARP inhibitor. The Indicator LOH Regions can be determined in at least two, five, ten, or 21 pairs of human chromosomes. The cancer cell can be an ovarian, breast, or esophageal cancer cell. The Indicator LOH Regions can have a length of about 6, 12, or 15 or more megabases. The Indicator LOH Regions can be present on a chromosome other than human chromosome 17.

In another aspect, this invention features a system for determining LOH status of a cancer cell of a cancer patient. The system comprises, or consists essentially of, (a) a sample analyzer configured to produce a plurality of signals about genomic DNA of at least one pair of human chromosomes of the cancer cell, and (b) a computer sub-system programmed to calculate, based on the plurality of signals, the number or combined length of Indicator LOH Regions in the at least one pair of human chromosomes. The computer sub-system can be programmed to compare the number or combined length of Indicator LOH Regions to a reference number to determine (a) a likelihood of a deficiency in BRCA1 and/or BRCA2 genes in the cancer cell, (b) a likelihood of a deficiency in HDR in the cancer cell, or (c) a likelihood that the cancer patient will respond to cancer treatment regimen comprising a DNA damaging agent, an anthracycline, a topoisomerase I inhibitor, radiation, or a PARP inhibitor. The system can comprise an output module configured to display the likelihood of (a), (b), or (c). The system can comprise an output module configured to display a recommendation for the use of the cancer treatment regimen. The Indicator LOH Regions can be determined in at least two, five, ten, or 21 pairs of human chromosomes. The cancer cell can be an ovarian, breast, or esophageal cancer cell. The Indicator LOH Regions can have a length of about 6, 12, or 15 or more megabases. The Indicator LOH Regions can be present on chromosomes other than a human chromosome 17. The DNA damaging agent can be a platinum-based chemotherapy drug, the anthracycline can be epirubincin or doxorubicin, the topoisomerase I inhibitor can be campothecin, topotecan, or irinotecan, or the PARP inhibitor can be iniparib, olaparib or velapirib.

In another aspect, the invention provides a computer program product embodied in a computer readable medium that, when executing on a computer, provides instructions for detecting the presence or absence of any LOH region along one or more of human chromosomes other than the human X and Y sex chromosomes, and the LOH region having a length of about 1.5 or more (or 5, 10 or more, preferably 15 or more) megabases but shorter than the length of the whole chromosome containing the LOH region; and determining the total number or combined length of the LOH regions in the one or more chromosome pairs. The computer program product can include other instructions. The Indicator LOH Regions can be determined in at least two, five, ten or 21 pairs of human chromosomes. The cancer cell can be an ovarian, breast, or esophageal cancer cell. The Indicator LOH Regions can have a length of about 6, 12, or 15 or more megabases. The Indicator LOH Regions can be present on chromosomes other than a human chromosome 17. The DNA damaging agent can be a platinum-based chemotherapy drug, the anthracycline can be epirubincin or doxorubicin, the topoisomerase I inhibitor can be campothecin, topotecan, or irinotecan, or the PARP inhibitor can be iniparib, olaparib or velapirib.

In another aspect, the present invention provides a diagnostic kit. The kit comprises, or consists essentially of, at least 500 oligonucleotides capable of hybridizing to a plurality of polymorphic regions of human genomic DNA; and a computer program product provided herein. The computer program product can be embodied in a computer readable medium that, when executing on a computer, provides instructions for detecting the presence or absence of any LOH region along one or more of human chromosomes other than the human X and Y sex chromosomes, and the LOH region having a length of about 1.5 or more (or 5 or 10 or more, preferably about 15 or more) megabases but shorter than the length of the whole chromosome containing the LOH region; and determining the total number and/or combined length of the LOH region in the one or more chromosome pairs.

In another aspect, this document features a method for assessing cancer cells of a patient for the presence of an LOH signature. The method comprises, or consists essentially of, (a) detecting the presence of more than a reference number of LOH regions in at least one pair of human chromosomes of a cancer cell of the cancer patient that are longer than a first length but shorter than the length of the whole chromosome containing the LOH region, wherein the at least one pair of human chromosomes is not a human X/Y sex chromosome pair, wherein the first length is about 1.5 or more megabases, and (b) identifying the patient as having cancer cells with the LOH signature.

In another aspect, this document features a method for assessing cancer cells of a patient for the presence of an HDR deficient status. The method comprises, or consists essentially of, (a) detecting the presence of more than a reference number of LOH regions in at least one pair of human chromosomes of a cancer cell of the cancer patient that are longer than a first length but shorter than the length of the whole chromosome containing the LOH region, wherein the at least one pair of human chromosomes is not a human X/Y sex chromosome pair, wherein the first length is about 1.5 or more megabases, and (b) identifying the patient as having cancer cells with the HDR deficient status.

In another aspect, this document features a method for assessing cancer cells of a patient for the presence of a genetic mutation within a gene from an HDR pathway. The method comprises, or consists essentially of, (a) detecting the presence of more than a reference number of LOH regions in at least one pair of human chromosomes of a cancer cell of the cancer patient that are longer than a first length but shorter than the length of the whole chromosome containing the LOH region, wherein the at least one pair of human chromosomes is not a human X/Y sex chromosome pair, wherein the first length is about 1.5 or more megabases, and (b) identifying the patient as having cancer cells with the genetic mutation.

In another aspect, this document features a method for determining if a patient is likely to respond to a cancer treatment regimen comprising administering radiation or a drug selected from the group consisting of DNA damaging agents, anthracyclines, topoisomerase I inhibitors, and PARP inhibitors. The method comprises, or consists essentially of, (a) detecting the presence of more than a reference number of LOH regions in at least one pair of human chromosomes of a cancer cell of the cancer patient that are longer than a first length but shorter than the length of the whole chromosome containing the LOH region, wherein the at least one pair of human chromosomes is not a human X/Y sex chromosome pair, wherein the first length is about 1.5 or more megabases, and (b) identifying the patient as being likely to respond to the cancer treatment regimen.

In another aspect, this document features a method for assessing a patient. The method comprises, or consists essentially of, (a) determining that the patient comprises cancer cells having an LOH signature, wherein the presence of more than a reference number of LOH regions in at least one pair of human chromosomes of a cancer cell of the cancer patient that are longer than a first length but shorter than the length of the whole chromosome containing the LOH region indicates that the cancer cells have the LOH signature, wherein the at least one pair of human chromosomes is not a human X/Y sex chromosome pair, wherein the first length is about 1.5 or more megabases, and (b) diagnosing the patient as having cancer cells with the LOH signature.

In another aspect, this document features a method for assessing a patient. The method comprises, or consists essentially of, (a) determining that the patient comprises cancer cells having an HDR deficiency status, wherein the presence of more than a reference number of LOH regions in at least one pair of human chromosomes of a cancer cell of the cancer patient that are longer than a first length but shorter than the length of the whole chromosome containing the LOH region indicates that the cancer cells have the HDR deficiency status, wherein the at least one pair of human chromosomes is not a human X/Y sex chromosome pair, wherein the first length is about 1.5 or more megabases, and (b) diagnosing the patient as having cancer cells with the HDR deficient status.

In another aspect, this document features a method for assessing a patient. The method comprises, or consists essentially of, (a) determining that the patient comprises cancer cells having a genetic mutation within a gene from an HDR pathway, wherein the presence of more than a reference number of LOH regions in at least one pair of human chromosomes of a cancer cell of the cancer patient that are longer than a first length but shorter than the length of the whole chromosome containing the LOH region indicates that the cancer cells have the genetic mutation, wherein the at least one pair of human chromosomes is not a human X/Y sex chromosome pair, wherein the first length is about 1.5 or more megabases, and (b) diagnosing the patient as having cancer cells with the genetic mutation.

In another aspect, this document features a method for assessing a patient for a likelihood to respond to a cancer treatment regimen comprising administering radiation or a drug selected from the group consisting of DNA damaging agents, anthracyclines, topoisomerase I inhibitors, and PARP inhibitors. The method comprises, or consists essentially of, (a) determining that the patient comprises cancer cells having an LOH signature, wherein the presence of more than a reference number of LOH regions in at least one pair of human chromosomes of a cancer cell of the cancer patient that are longer than a first length but shorter than the length of the whole chromosome containing the LOH region indicates that the cancer cells have the LOH signature, wherein the at least one pair of human chromosomes is not a human X/Y sex chromosome pair, wherein the first length is about 1.5 or more megabases, and (b) diagnosing, based at least in part on the presence of the LOH signature, the patient as being likely to respond to the cancer treatment regimen.

In another aspect, this document features a method for performing a diagnostic analysis of a cancer cell of a patient.

The method comprises, or consists essentially of, (a) detecting the presence of more than a reference number of LOH regions in at least one pair of human chromosomes of the cancer cell that are longer than a first length but shorter than the length of the whole chromosome containing the LOH region, wherein the at least one pair of human chromosomes is not a human X/Y sex chromosome pair, wherein the first length is about 1.5 or more megabases, and (b) identifying the patient as having cancer cells with an LOH signature.

In another aspect, this document features a method for performing a diagnostic analysis of a cancer cell of a patient. The method comprises, or consists essentially of, (a) detecting the presence of more than a reference number of LOH regions in at least one pair of human chromosomes of the cancer cell that are longer than a first length but shorter than the length of the whole chromosome containing the LOH region, wherein the at least one pair of human chromosomes is not a human X/Y sex chromosome pair, wherein the first length is about 1.5 or more megabases, and (b) identifying the patient as having cancer cells with a HDR deficient status.

In another aspect, this document features a method for performing a diagnostic analysis of a cancer cell of a patient. The method comprises, or consists essentially of, (a) detecting the presence of more than a reference number of LOH regions in at least one pair of human chromosomes of the cancer cell that are longer than a first length but shorter than the length of the whole chromosome containing the LOH region, wherein the at least one pair of human chromosomes is not a human X/Y sex chromosome pair, wherein the first length is about 1.5 or more megabases, and (b) identifying the patient as having cancer cells with a genetic mutation within a gene from an HDR pathway.

In another aspect, this document features a method for performing a diagnostic analysis of a cancer cell of a patient to determine if the cancer patient is likely to respond to a cancer treatment regimen comprising administering radiation or a drug selected from the group consisting of DNA damaging agents, anthracyclines, topoisomerase I inhibitors, and PARP inhibitors. The method comprises, or consists essentially of, (a) detecting the presence of more than a reference number of LOH regions in at least one pair of human chromosomes of the cancer cell that are longer than a first length but shorter than the length of the whole chromosome containing the LOH region, wherein the at least one pair of human chromosomes is not a human X/Y sex chromosome pair, wherein the first length is about 1.5 or more megabases, and (b) identifying the patient as being likely to respond to the cancer treatment regimen.

In another aspect, this document features a method for diagnosing a patient as having cancer cells having an LOH signature. The method comprises, or consists essentially of, (a) determining that the patient comprises cancer cells having the LOH signature, wherein the presence of more than a reference number of LOH regions in at least one pair of human chromosomes of a cancer cell of the cancer patient that are longer than a first length but shorter than the length of the whole chromosome containing the LOH region indicates that the cancer cells have the LOH signature, wherein the at least one pair of human chromosomes is not a human X/Y sex chromosome pair, wherein the first length is about 1.5 or more megabases, and (b) diagnosing the patient as having cancer cells with the LOH signature.

In another aspect, this document features a method for diagnosing a patient as having cancer cells with an HDR deficient status. The method comprises, or consists essentially of, (a) determining that the patient comprises cancer cells having the HDR deficiency status, wherein the presence of more than a reference number of LOH regions in at least one pair of human chromosomes of a cancer cell of the cancer patient that are longer than a first length but shorter than the length of the whole chromosome containing the LOH region indicates that the cancer cells have the HDR deficiency status, wherein the at least one pair of human chromosomes is not a human X/Y sex chromosome pair, wherein the first length is about 1.5 or more megabases, and (b) diagnosing the patient as having cancer cells with the HDR deficient status.

In another aspect, this document features a method for diagnosing a patient as having cancer cells with a genetic mutation within a gene from an HDR pathway. The method comprises, or consists essentially of, (a) determining that the patient comprises cancer cells having the genetic mutation, wherein the presence of more than a reference number of LOH regions in at least one pair of human chromosomes of a cancer cell of the cancer patient that are longer than a first length but shorter than the length of the whole chromosome containing the LOH region indicates that the cancer cells have the genetic mutation, wherein the at least one pair of human chromosomes is not a human X/Y sex chromosome pair, wherein the first length is about 1.5 or more megabases, and (b) diagnosing the patient as having cancer cells with the genetic mutation.

In another aspect, this document features a method for diagnosing a patient as being a candidate for a cancer treatment regimen comprising administering radiation or a drug selected from the group consisting of DNA damaging agents, anthracyclines, topoisomerase I inhibitors, and PARP inhibitors. The method comprises, or consists essentially of, (a) determining that the patient comprises cancer cells having an LOH signature, wherein the presence of more than a reference number of LOH regions in at least one pair of human chromosomes of a cancer cell of the cancer patient that are longer than a first length but shorter than the length of the whole chromosome containing the LOH region indicates that the cancer cells have the LOH signature, wherein the at least one pair of human chromosomes is not a human X/Y sex chromosome pair, wherein the first length is about 1.5 or more megabases, and (b) diagnosing, based at least in part on the presence of the LOH signature, the patient as being likely to respond to the cancer treatment regimen.

Unless otherwise defined, all technical and scientific terms used herein have the same meaning as commonly understood by one of ordinary skill in the art to which this invention pertains. Although methods and materials similar or equivalent to those described herein can be used to practice the invention, suitable methods and materials are described below. All publications, patent applications, patents, and other references mentioned herein are incorporated by reference in their entirety. In case of conflict, the present specification, including definitions, will control. In addition, the materials, methods, and examples are illustrative only and not intended to be limiting.

The details of one or more embodiments of the invention are set forth in the description and accompanying drawings below. The materials, methods, and examples are illustrative only and not intended to be limiting. Other features, objects, and advantages of the invention will be apparent from the description and drawings, and from the claims.

DESCRIPTION OF THE DRAWINGS

FIG. 9 is a table showing the percent of ovarian cancer samples that are BRCA deficient, HDR deficient/BRCA intact, and HDR intact.

DETAILED DESCRIPTION

Figure 1:
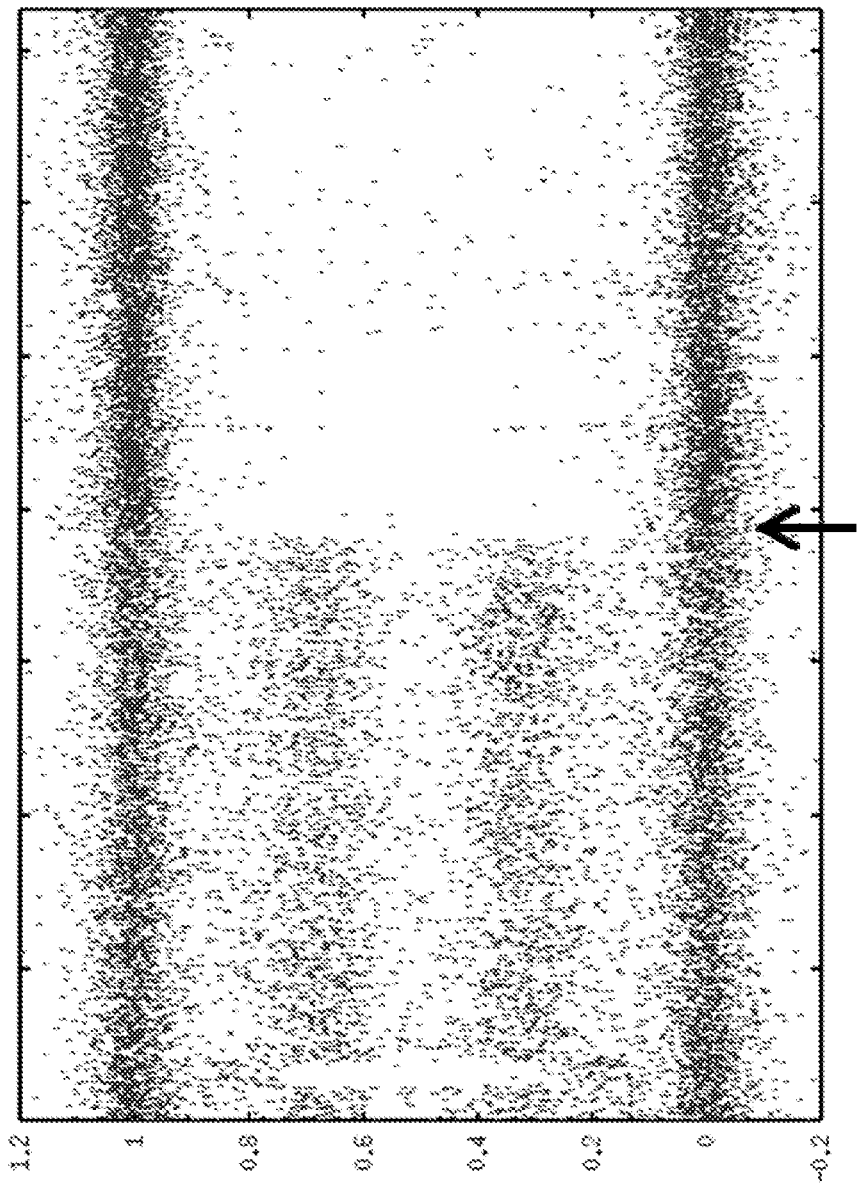
FIG. 1 is a graph plotting allele dosages of breast cancer cells from a breast cancer patient along chromosome 1 as determined using a SNP array. The arrow indicates a transition between a region of heterozygosity and an LOH region.

This document provides methods and materials involved in assessing samples (e.g., cancer cells) for the presence of an LOH signature. For example, this document provides methods and materials for determining whether or not a cell (e.g., a human cancer cell) contains an LOH signature (e.g., a HDR-deficiency LOH signature).

In general, a comparison of sequences present at the same locus on each chromosome (each autosomal chromosome for males) can reveal whether that particular locus is homozygous or heterozygous within the genome of a cell. Polymorphic loci within the human genome are generally heterozygous within an individual since that individual typically receives one copy from the biological father and one copy from the biological mother. In some cases, a polymorphic locus or a string of polymorphic loci within an individual are homozygous as a result of inheriting identical copies from both biological parents.

Loss of heterozygosity (LOH) may result from several mechanisms. For example, in some cases, a region of one chromosome can be deleted in a somatic cell. The region that remains present on the other chromosome (the other non-sex chromosome for males) is an LOH region as there is only one copy (instead of two copies) of that region present within the genome of the affected cells. This LOH region can be any length (e.g., from a length less than about 1.5 Mb up to a length equal to the entire length of the chromosome). This type of LOH event results in a copy number reduction. In other cases, a region of one chromosome (one non-sex chromosome for males) in a somatic cell can be replaced with a copy of that region from the other chromosome, thereby eliminating any heterozygosity that may have been present within the replaced region. In such cases, the region that remains present on each chromosome is an LOH region and can be referred to as a copy neutral LOH region. Copy neutral LOH regions can be any length (e.g., from a length less than about 1.5 Mb up to a length equal to the entire length of the chromosome).

As described herein, a cellular sample (e.g., cancer cell sample) can be identified as having a "positive LOH signature status" (or alternatively called "HDR-deficiency LOH signature") if the genome of the cells being assessed contains five or more (e.g., six or more, seven or more, eight or more, nine or more, ten or more, eleven or more, 12 or more, 13 or more, 14 or more, 15 or more, 16 or more, 17 or more, 18 or more, 19 or more, or 20 or more) LOH regions that are (a) longer than about 1.5 megabases (e.g., longer than about 2, 2.5, 3, 4, 5, 6, 7, 8, 9, 10, 11, 12, 13, 14, 15, 16, 17, 18, 19, 20, 25, 30, 35, 40, 45, 50, 75, or 100 megabases (Mb), preferably longer than about 14 or 15 or 16, more preferably longer than about 15 megabases) and (b) less than the length of the entire chromosome that contains that LOH region. In some cases, a cancer cell sample can be identified as having a positive LOH signature status if the genome of the cells being assessed contains nine or more LOH regions that are (a) longer than about 15 Mb and (b) less than the length of the entire chromosome that contains that LOH region. Unless otherwise defined, the term "Indicator LOH Region" refers to an LOH region that is in a pair of human chromosomes other than the human X/Y sex chromosome pair, and that is characterized by loss of heterozygosity with a length of about 1.5 or more megabases but shorter than the length of the whole chromosome containing the LOH region. The length of the whole chromosome containing an LOH region may be determined by examining the length of the shorter chromosome of the corresponding chromosome pair in a germline cell or a non-tumor somatic cell. In some embodiments, an Indicator LOH Region is any LOH region about 2, 2.5, 3, 4, 5, 6, 7, 8, 9, 10, 11, 12, 13, 14, 15, 16, 17, 18, 19, 20, 25, 30, 35, 40, 45, 50, 75, or 100 megabases (Mb) or more (preferably longer than about 14 or 15 megabases) and less than the length of the whole chromosome that contains that LOH region.

Cells (e.g., cancer cells) identified as having a positive LOH signature (also termed herein "HDR-deficiency LOH signature") can be classified as having an increased likelihood of having an HDR deficiency and/or as having an increased likelihood of having a deficient status in one or more genes in the HDR pathway. For example, cancer cells identified as having a positive LOH signature status can be classified as having an increased likelihood of having an HDR deficient status. In some cases, cancer cells identified as having a positive LOH signature status can be classified as having an increased likelihood of having a deficient status for one or more genes in the HDR pathway. As used herein, deficient status for a gene means the sequence, structure, expression and/or activity of the gene or its product is/are deficient as compared to normal. Examples include, but are not limited to, low or no mRNA or protein expression, deleterious mutations, hypermethylation, attenuated activity (e.g., enzymatic activity, ability to bind to another biomolecule), etc. As used herein, deficient status for a pathway (e.g., HDR pathway) means at least one gene in that pathway (e.g., BRCA1) is deficient. Examples of highly deleterious mutations include frameshift mutations, stop codon mutations, and mutations that lead to altered RNA splicing. Deficient status in a gene in the HDR pathway may result in deficiency or reduced activity in homology directed repair in the cancer cells. Examples of genes in the HDR pathway include, without limitation, the genes listed in Table 1.

TABLE 1

Selected HDR Pathway Genes

| Gene Name | Entrez Gene Symbol (if assigned) | Entrez Gene Id |
|---|---|---|
| BLM | BLM | 641 |
| BRCA1 | BRCA1 | 672 |
| BRCA2 | BRCA2 | 675 |
| CtIP | RBBP8 | 5932 |
| DNA polymerase delta | POLD1 | 5424 |
| | POLD2 | 5424 |
| | POLD3 | 10714 |
| | POLD4 | 57804 |

TABLE 1-continued

Selected HDR Pathway Genes

| Gene Name | Entrez Gene Symbol (if assigned) | Entrez Gene Id |
|---|---|---|
| DNA polymerase eta | POLH | 5429 |
| DNA2 | DNA2 | 1763 |
| EME1 | EME1 | 146956 |
| ERCC1 | ERCC1 | 2067 |
| EXO1 | EXO1 | 9156 |
| FANCM | FANCM | 57697 |
| GEN1 | GEN1 | 348654 |
| MRE11 | MRE11A | 4361 |
| MUS81 | MUS81 | 80198 |
| NBS1 | NBN | 4683 |
| PALB2 | PALB2 | 79728 |
| PCNA | PCNA | 5111 |
| RAD50 | RAD50 | 10111 |
| RAD51 | RAD51 | 5888 |
| RAD51AP1 | RAD51AP1 | 10635 |
| RAD51B | RAD51L1 | 5890 |
| RAD51C | RAD51C | 5889 |
| RAD51D | RAD51L3 | 5892 |
| RAD54 | ATRX | 546 |
| RAD54B | RAD54B | 25788 |
| RMI1 | RMI1 | 80010 |
| RMI2 | C16orf75 | 116028 |
| RPA | RPA1 | 6117 |
| RTEL1 | RTEL1 | 51750 |
| SLX1 | | |
| SLX2 | | |
| SLX4 | SLX4 | 84464 |
| TOP2A | TOP2A | 7153 |
| XPF | ERCC4 | 2072 |
| XRCC2 | XRCC2 | 7516 |
| XRCC3 | XRCC3 | 7517 |

Examples of genetic mutations that can be present within a gene of the HDR pathway include, without limitation, those listed in Table 2.

TABLE 2

Possible genetic mutations within selected genes of the HDR pathway.

| Gene | Mutation | Entrez Gene ID |
|---|---|---|
| BRCA1 | C24F | 672 |
| BRCA1 | E29X | 672 |
| BRCA2 | R3052W | 675 |
| BRCA2 | 2881delG | 675 |
| RAD51C | G125V | 5889 |
| RAD51C | L138F | 5889 |
| RAD51C | Y75XfsX0 | 5889 |

In some cases, a cellular sample (e.g., cancer cell sample) can be identified as having an increased number of LOH regions (e.g., at least 7, 8, 9, 10, or more LOH regions) that cover the whole chromosome. Cells (e.g., cancer cells) identified as having an increased number of LOH regions that cover the whole chromosome can be classified as having an increased likelihood of having HDR proficiency, that is, intact HDR pathway. For example, cancer cells identified as having an increased number of LOH regions that cover the whole chromosome can be classified as being more likely to have intact BRCA1 and BRCA2 genes.

As described herein, identifying LOH loci (as well as the size and number of LOH regions) can include, first, determining the genotype of a sample at various genomic loci (e.g., SNP loci, individual bases in large sequencing) and, second, determining whether homozygous loci are due to LOH events. Any appropriate technique can be used to determine genotypes at loci of interest within the genome of a cell. For example, single nucleotide polymorphisms (SNP) arrays (e.g., human genome-wide SNP arrays), targeted sequencing of loci of interest (e.g., sequencing SNP loci and their surrounding sequences), and even untargeted sequencing (e.g., whole exome, transcriptome, or genome sequencing) can be used to identify loci as being homozygous or heterozygous. In some cases, an analysis of the homozygous or heterozygous nature of loci over a length of a chromosome can be performed to determine the length of regions of homozygosity or heterozygosity. For example, a stretch of SNP locations that are spaced apart (e.g., spaced about 25 kb to about 100 kb apart) along a chromosome can be evaluated using SNP array results to determine not only the presence of a region of homozygosity along a chromosome but also the length of that region. Results from a SNP array can be used to generate a graph that plots allele dosages along a chromosome. Allele dosage $d_i$ for SNP i can be calculated from adjusted signal intensities of two alleles ($A_i$ and $B_i$): $d_i=A_i/(A_i+B_i)$. An example of such a graph is presented in FIG. 1. Numerous variations on nucleic acid arrays useful in the invention are known in the art. These include the arrays used in the various examples below (e.g., Affymetrix 500K GeneChip array in Example 3; Affymetrix OncoScan™ FFPE Express 2.0 Services (Formerly MIP CN Services) in Example 4).

Once a sample's genotype has been determined for a plurality of loci (e.g., SNPs), common techniques can be used to identify loci and regions of LOH. One way to determine whether homozygosity is due to LOH is to compare the somatic genotype to the germline. For example, the genotype for a plurality of loci (e.g., SNPs) can be determined in both a germline (e.g., blood) sample and a somatic (e.g., tumor) sample. The genotypes for each sample can be compared (typically computationally) to determine where the genome of the germline cell was heterozygous and the genome of the somatic cell is homozygous. Such loci are LOH loci and regions of such loci are LOH regions.

Computational techniques can also be used to determine whether homozygosity is due to LOH. Such techniques are particularly useful when a germline sample is not available for analysis and comparison. For example, algorithms such as those described elsewhere can be used to detect LOH regions using information from SNP arrays (Nannya et al., Cancer Res. (2005) 65:6071-6079 (2005)). Typically these algorithms do not explicitly take into account contamination of tumor samples with benign tissue. Cf International Application No. PCT/US2011/026098 to Abkevich et al.; Goransson et al., PLoS One (2009) 4(6):e6057. This contamination is often high enough to make the detection of LOH regions challenging. Improved analytical methods according to the present invention for identifying LOH, even in spite of contamination, include those embodied in computer software products as described below.

The following is one example. If the observed ratio of the signals of two alleles, A and B, is two to one, there are two possibilities. The first possibility is that cancer cells have LOH with deletion of allele B in a sample with 50% contamination with normal cells. The second possibility is that there is no LOH but allele A is duplicated in a sample with no contamination with normal cells. An algorithm can be implemented as a computer program as described herein to reconstruct LOH regions based on genotype (e.g., SNP genotype) data. One point of the algorithm is to first reconstruct allele specific copy numbers (ASCN) at each locus (e.g., SNP). ASCNs are the numbers of copies of both paternal and maternal alleles. An LOH region is then determined as a stretch of SNPs with one of the ASCNs (paternal or maternal) being zero. The algorithm can be based on maximizing a likelihood function and can be conceptually akin to a previously described algorithm designed to reconstruct total copy number (rather than ASCN) at each locus (e.g., SNP). See International Application No. PCT/US2011/026098 to Abkevich et al. The likelihood function can be maximized over ASCN of all loci, level of contamination with benign tissue, total copy number averaged over the whole genome, and sample specific noise level. The input data for the algorithm can include or consist of (1) sample-specific normalized signal intensities for both allele of each locus and (2) assay-specific (specific for different SNP arrays and for sequence based approach) set of parameters defined based on analysis of large number of samples with known ASCN profiles.

In some cases, nucleic acid sequencing techniques can be used to identify loci as being homozygous or heterozygous. For example, genomic DNA from a cell sample (e.g., a cancer cell sample) can be extracted and fragmented. Any appropriate method can be used to extract and fragment genomic nucleic acid including, without limitation, commercial kits such as QIAamp™ DNA Mini Kit (Qiagen™), MagNA™ Pure DNA Isolation Kit (Roche Applied Science™) and GenElute™ Mammalian Genomic DNA Miniprep Kit (Sigma-Aldrich™). Once extracted and fragmented, either targeted or untargeted sequencing can be done to determine the sample's genotypes at loci. For example, whole genome, whole transcriptome, or whole exome sequencing can be done to determine genotypes at millions or even billions of base pairs (i.e., base pairs can be "loci" to be evaluated).

In some cases, targeted sequencing of known polymorphic loci (e.g., SNPs and surrounding sequences) can be done as an alternative to microarray analysis. For example, the genomic DNA can be enriched for those fragments containing a locus (e.g., SNP location) to be analyzed using kits designed for this purpose (e.g., Agilent SureSelect™, Illumina TruSeq Capture™, and Nimblegen SeqCap EZ Choice™). For example, genomic DNA containing the loci to be analyzed can be hybridized to biotinylated capture RNA fragments to form biotinylated RNA/genomic DNA complexes. Alternatively, DNA capture probes may be utilized resulting in the formation of biotinylated DNA/genomic DNA hybrids. Streptavidin coated magnetic beads and a magnetic force can be used to separate the biotinylated RNA/genomic DNA complexes from those genomic DNA fragments not present within a biotinylated RNA/genomic DNA complex. The obtained biotinylated RNA/genomic DNA complexes can be treated to remove the captured RNA from the magnetic beads, thereby leaving intact genomic DNA fragments containing a locus to be analyzed. These intact genomic DNA fragments containing the loci to be analyzed can be amplified using, for example, PCR techniques. The amplified genomic DNA fragments can be sequenced using a high-throughput sequencing technology or a next-generation sequencing technology such as Illumina HiSeq™, Illumina MiSeq™, Life Technologies SoLID™ or Ion Torrent™, or Roche 454™.

Figure 2:
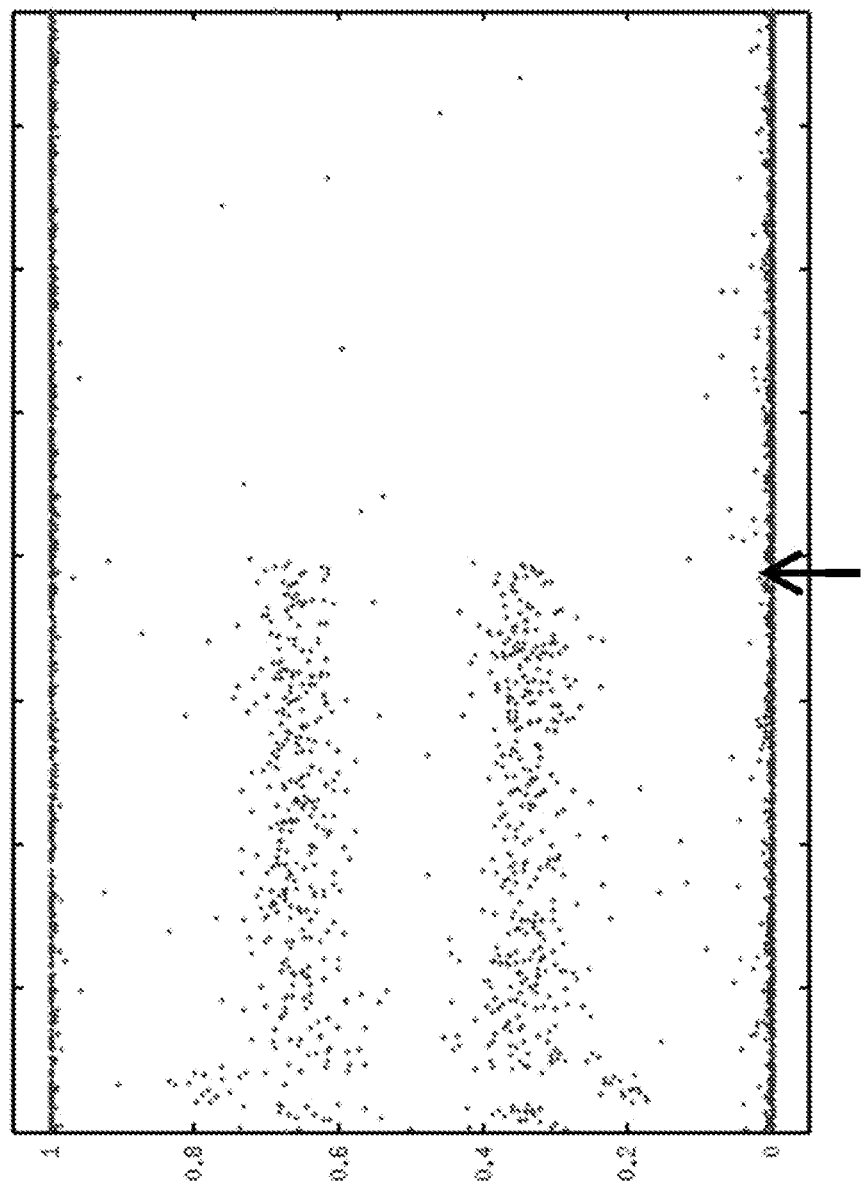
FIG. 2 is a graph plotting allele dosages of breast cancer cells for the same breast cancer patient as on FIG. 1 along chromosome 1 as determined using high-throughput sequencing. The arrow indicates a transition between a region of heterozygosity and an LOH region.

The sequencing results from the genomic DNA fragments can be used to identify loci as being homozygous or heterozygous, analogous to the microarray analysis described herein. In some cases, an analysis of the homozygous or heterozygous nature of loci over a length of a chromosome can be performed to determine the length of regions of homozygosity or heterozygosity. For example, a stretch of SNP locations that are spaced apart (e.g., spaced about 25 kb to about 100 kb apart) along a chromosome can be evaluated by sequencing, and the sequencing results used to determine not only the presence of a region of homozygosity along a chromosome but also the length of that LOH region. Obtained sequencing results can be used to generate a graph that plots allele dosages along a chromosome. Allele dosage $d_i$ for SNP i can be calculated from adjusted number of captured probes for two alleles ($A_i$ and $B_i$): $=A_i/(A_i+B_i)$. An example of such a graph is presented in FIG. 2. Determining whether homozygosity is due to LOH (as opposed to homozygosity in the germline) can be performed as described herein.

In some cases, a selection process can be used to select loci (e.g., SNP loci) to be evaluated using an assay configured to identify loci as being homozygous or heterozygous (e.g., SNP array-based assays and sequencing-based assays). For example, any human SNP location can be selected for inclusion in a SNP array-based assay or a sequencing-based assay configured to identify loci as being homozygous or heterozygous within the genome of cells. In some cases, 0.5, 1.0, 1.5, 2.0, 2.5 million or more SNP locations present within the human genome can be evaluated to identify those SNPs that (a) are not present on the Y chromosome, (b) are not mitochondrial SNPs, (c) have a minor allele frequency of at least about five percent in Caucasians, (d) have a minor allele frequency of at least about one percent in three races other than Caucasians (e.g., Chinese, Japanese, and Yoruba), and/or (e) do not have a significant deviation from Hardy Weinberg equilibrium in any of the four races. In some cases, more than 100,000, 150,000, or 200,000 human SNPs can be selected that meet criteria (a) through (e). Of the human SNPs meeting criteria (a) through (e), a group of SNPs (e.g., top 110,000 SNPs) can be selected such that the SNPs have a high degree of allele frequency in Caucasians, cover the human genome in a somewhat evenly spaced manner (e.g., at least one SNP every about 25 kb to about 500 kb), and are not in linkage disequilibrium with another selected SNP for in any of the four races. In some cases, about 40, 50, 60, 70, 80, 90, 100, 110, 120, 130 thousand or more SNPs can be selected as meeting each of these criteria and included in an assay configured to identify LOH regions across a human genome. For example, between about 70,000 and about 90,000 (e.g., about 80,000) SNPs can be selected for analysis with a SNP array-based assay, and between about 45,000 and about 55,000 (e.g., about 54,000) SNPs can be selected for analysis with a sequencing-based assay.

As described herein, a cell sample can be assessed to determine if the genome of cells of the sample contains an LOH signature, lacks an LOH signature, has an increased number of LOH regions that cover the whole chromosome, or lacks an increased number of LOH regions that cover the whole chromosome. Any appropriate type of sample can be assessed. For example, a sample containing cancer cells can be assessed to determine if the genome of the cancer cells contains an LOH signature, lacks an LOH signature, has an increased number of LOH regions that cover the whole chromosome, or lacks an increased number of LOH regions that cover the whole chromosome. Examples of samples containing cancer cells that can be assessed as described herein include, without limitation, tumor biopsy samples (e.g., breast tumor biopsy samples), formalin-fixed, paraffin-embedded tissue samples containing cancer cells, core needle biopsies, fine needle aspirates, and samples containing cancer cells shed from a tumor (e.g., blood, urine or other bodily fluids). For formalin-fixed, paraffin-embedded tissue samples, the sample can be prepared by DNA extraction using a genomic DNA extraction kit optimized for FFPE tissue, including but not limited to those described above (e.g., QuickExtract™ FFPE DNA Extraction Kit (Epicentre™), and QIAamp™ DNA FFPE Tissue Kit (Qiagen™)).

In some cases, laser dissection techniques can be performed on a tissue sample to minimize the number of non-cancer cells within a cancer cell sample to be assessed. In some cases, antibody based purification methods can be used to enrich for cancer cells and/or deplete non-cancer cells. Examples of antibodies that could be used for cancer cell enrichment include, without limitation, anti-EpCAM, anti-TROP-2, anti-c-Met, anti-Folate binding protein, anti-N-Cadherin, anti-CD318, anti-antimesencymal stem cell antigen, anti-Her2, anti-MUC1, anti-EGFR, anti-cytokeratins (e.g., cytokeratin 7, cytokeratin 20, etc.), anti-Caveolin-1, anti-PSA, anti-CA125, and anti-surfactant protein antibodies.

Any type of cancer cell can be assessed using the methods and materials described herein. For example, breast cancer cells, ovarian cancer cells, liver cancer cells, esophageal cancer cells, lung cancer cells, head and neck cancer cells, prostate cancer cells, colon, rectal, or colorectal cancer cells, and pancreatic cancer cells can be assessed to determine if the genome of the cancer cells contains an LOH signature, lacks an LOH signature, has an increased number of LOH regions that cover the whole chromosome, or lacks an increased number of LOH regions that cover the whole chromosome. In some embodiments, the cancer cells are primary or metastatic cancer cells of ovarian cancer, breast cancer, lung cancer or esophageal cancer.

When assessing the genome of cancer cells for the presence or absence of an LOH signature, one or more (e.g., one, two, three, four, five, six, seven, eight, nine, ten, eleven, twelve, 13, 14, 15, 16, 17, 18, 19, 20, 21, 22, or 23) pairs of chromosomes can be assessed. In some cases, the genome of cancer cells is assessed for the presence or absence of an LOH signature using one or more (e.g., one, two, three, four, five, six, seven, eight, nine, ten, eleven, twelve, 13, 14, 15, 16, 17, 18, 19, 20, 21, 22, 23) pairs of chromosomes.

In some cases, it can be helpful to exclude certain chromosomes from this analysis. For example, in the case of females, a pair to be assessed can include the pair of X sex chromosomes; whereas, in the case of males, a pair of any autosomal chromosomes (i.e., any pair other than the pair of X and Y sex chromosomes) can be assessed. As another example, in some cases the chromosome number 17 pair may be excluded from the analysis. It has been determined that certain chromosomes carry unusually high levels of LOH in certain cancers and, thus, it can be helpful to exclude such chromosomes when analyzing samples as described herein from patients having these cancers. In some cases, the sample is from a patient having ovarian cancer, and the chromosome to be excluded is chromosome 17.

When assessing the genome of cancer cells for the presence or absence of an increased number of LOH regions that cover the whole chromosome, 10 or more (e.g., 13, 16, 19 or 23) pairs of chromosomes can be assessed. In the case of females, a pair to be assessed can include the pair of X sex chromosomes; whereas, in the case of males, a pair of any autosomal chromosomes (i.e., any pair other than the pair of X and Y sex chromosomes) can be assessed. In some cases, the chromosome number 17 pair may be excluded from the analysis. In some cases, the sample is from a patient having ovarian cancer, and the chromosome to be excluded is chromosome 17. In some cases, the genome of cancer cells is assessed for the presence or absence of an increased number of LOH regions that cover the whole chromosome using 10 or more (e.g., 13, 16, 19, or 23) pairs of chromosomes.

Thus, a predefined number of chromosomes may be analyzed to determine the total number of Indicator LOH Regions, preferably the total number of LOH regions of a length of greater than 9 megabases, 10 megabases, 12 megabases, 14 megabases, more preferably greater than 15 megabases. Alternatively or in addition, the sizes of all identified Indicator LOH Regions may be summed up to obtain a total length of Indicator LOH Regions.

For classification of positive LOH signature status, the reference number discussed above for the total number of Indicator LOH Regions may be 5, 6, 7, 8, 9, 10, 11, 12, 13, 14, 15, 16, 18, 19, 20 or greater, preferably 5, preferably 8, more preferably 9 or 10, most preferably 10. The reference number for the total (e.g., combined) length of Indicator LOH Regions may be about 75, 90, 105, 120, 130, 135, 150, 175, 200, 225, 250, 275, 300, 325 350, 375, 400, 425, 450, 475, 500 megabases or greater, preferably about 75 megabases or greater, preferably about 90 or 105 megabases or greater, more preferably about 120 or 130 megabases or greater, and more preferably about 135 megabases or greater, and most preferably about 150 megabases or greater.

In some specific embodiments, the total number of LOH regions of a length of greater than about 14 or 15 megabases is determined and compared to a reference number of about 5, 6, 7, 8, 9, 10, 11, 12, 13, 14, 15, 16, 18, 19, or 20. Alternatively or in addition, the total length of LOH regions of a length of greater than about 14 or 15 megabases is determined and compared to a reference number of about 75, 90, 105, 120, 130, 135, 150, 175, 200, 225, 250, 275, 300, 325 350, 375, 400, 425, 450, 475, or 500 megabases.

In some embodiments, the number of LOH regions (or the combined length, or a test value or score derived from either) in a patient sample is considered "greater" than a reference if it is at least 2-, 3-, 4-, 5-, 6-, 7-, 8-, 9-, or 10-fold greater than the reference while in some embodiments, it is considered "greater" if it is at least 1, 2, 3, 4, 5, 6, 7, 8, 9, or 10 standard deviations greater than the reference. Conversely, in some embodiments the number of LOH regions (or the combined length, or a test value or score derived from either) in a patient sample is considered "not greater" than a reference if it is not more than 2-, 3-, 4-, 5-, 6-, 7-, 8-, 9-, or 10-fold greater than the reference while in some embodiments, it is considered "not greater" if it is not more than 1, 2, 3, 4, 5, 6, 7, 8, 9, or 10 standard deviations greater than the reference.

In some embodiments the reference number (or length, value or score) is derived from a relevant reference population. Such reference populations may include patients (a) with the same cancer as the patient being tested, (b) with the same cancer sub-type, (c) with cancer having similar genetic or other clinical or molecular features, (d) who responded to a particular treatment, (e) who did not respond to a particular treatment, (f) who are apparently healthy (e.g., do not have any cancer or at least do not have the tested patient's cancer), etc. The reference number (or length, value or score) may be (a) representative of the number (or length, value or score) found in the reference population as a whole, (b) an average (mean, median, etc.) of the number (or length, value or score) found in the reference population as a whole or a particular sub-population, (c) representative of the number (or length, value or score) (e.g., an average such as mean or median) found in terciles, quartiles, quintiles, etc. of the reference population as ranked by (i) their respective number (or length, value or score) or (ii) the clinical feature they were found to have (e.g., strength of response, prognosis (including time to cancer-specific death), etc.).

As described herein, patients having cancer cells identified as having a positive LOH signature status can be classified, based at least in part on a positive LOH signature status, as being likely to respond to a particular cancer treatment regimen. For example, patients having cancer cells with a genome containing an LOH signature can be classified, based at least in part on a positive LOH signature status, as being likely to respond to a cancer treatment regimen that includes the use of a DNA damaging agent, a synthetic lethality agent (e.g., a PARP inhibitor), radiation, or a combination thereof. Preferably the patients are treatment naïve patients. Examples of DNA damaging agents include, without limitation, platinum-based chemotherapy drugs (e.g., cisplatin, carboplatin, oxaliplatin, and picoplatin), anthracyclines (e.g., epirubicin and doxorubicin), topoisomerase I inhibitors (e.g., campothecin, topotecan, and irinotecan), DNA crosslinkers such as mitomycin C, and triazene compounds (e.g., dacarbazine and temozolomide). Synthetic lethality therapeutic approaches typically involve administering an agent that inhibits at least one critical component of a biological pathway that is especially important to a particular tumor cell's survival. For example, when a tumor cell has a deficient homologous repair pathway (e.g., as determined according to the present invention), inhibitors of poly ADP ribose polymerase (or platinum drugs, double strand break repair inhibitors, etc.) can be especially potent against such tumors because two pathways critical to survival become obstructed (one biologically, e.g., by BRCA1 mutation, and the other synthetically, e.g., by administration of a pathway drug). Synthetic lethality approaches to cancer therapy are described in, e.g., O'Brien et al., *Converting cancer mutations into therapeutic opportunities*, EMBO MOL. MED. (2009) 1:297-299. Examples of synthetic lethality agents include, without limitation, PARP inhibitors or double strand break repair inhibitors in homologous repair-deficient tumor cells, PARP inhibitors in PTEN-deficient tumor cells, methotrexate in MSH2-deficient tumor cells, etc. Examples of PARP inhibitors include, without limitation, olaparib, iniparib, and veliparib. Examples of double strand break repair inhibitors include, without limitation, KU55933 (ATM inhibitor) and NU7441 (DNA-PKcs inhibitor). Examples of information that can be used in addition to a positive LOH signature status to base a classification of being likely to respond to a particular cancer treatment regimen include, without limitation, previous treatment results, germline or somatic DNA mutations, gene or protein expression profiling (e.g., ER/PR/HER2 status, PSA levels), tumor histology (e.g., adenocarcinoma, squamous cell carcinoma, papillary serous carcinoma, mucinous carcinoma, invasive ductal carcinoma, ductal carcinoma in situ (non-invasive), etc.), disease stage, tumor or cancer grade (e.g., well, moderately, or poorly differentiated (e.g., Gleason, modified Bloom Richardson), etc.), number of previous courses of treatment, etc.

Once classified as being likely to respond to a particular cancer treatment regimen (e.g., a cancer treatment regimen that includes the use of a DNA damaging agent, a PARP inhibitor, radiation, or a combination thereof), the cancer patient can be treated with such a cancer treatment regimen. In some embodiments, the patients are treatment naïve patients. Any appropriate method for treating the cancer at issue can be used to treat a cancer patient identified as having cancer cells having a positive LOH signature status. For example, platinum-based chemotherapy drugs or a combination of platinum-based chemotherapy drugs can be used to treat cancer as described elsewhere (see, e.g., U.S. Pat. Nos. 3,892,790, 3,904,663, 7,759,510, 7,759,488 and 7,754,684. In some cases, anthracyclines or a combination of anthracyclines can be used to treat cancer as described elsewhere (see, e.g., U.S. Pat. Nos. 3,590,028, 4,138,480, 4,950,738, 6,087, 340, 7,868,040, and 7,485,707. In some cases, topoisomerase I inhibitors or a combination of topoisomerase I inhibitors can be used to treat cancer as described elsewhere (see, e.g., U.S. Pat. Nos. 5,633,016 and 6,403,563. In some cases, PARP inhibitors or a combination of PARP inhibitors can be used to treat cancer as described elsewhere (see, e.g., U.S. Pat. Nos. 5,177,075, 7,915,280, and 7,351,701. In some cases, radiation can be used to treat cancer as described elsewhere (see, e.g., U.S. Pat. No. 5,295,944). In some cases, a combination comprising different agents (e.g., a combination comprising any of platinum-based chemotherapy drugs, anthracyclines, topoisomerase I inhibitors, and/or PARP inhibitors) with or without radiation treatments can be used to treat cancer. In some cases, a combination treatment may comprise any of the above agents or treatments (e.g., a DNA damaging agent, a PARP inhibitor, radiation, or a combination thereof) together with another agent or treatment—e.g., a taxane agent (e.g., doxetaxel, paclitaxel, abraxane), a growth factor or growth factor receptor inhibitor (e.g., erlotinib, gefitinib, lapatinib, sunitinib, bevacizumab, cetuximab, trastuzumab, panitumumab), and/or an antimetabolite (e.g., 5-flourouracil, methotrexate).

In some cases, patients identified as having cancer cells with a genome lacking an LOH signature can be classified, based at least in part on a negative LOH signature status, as being less likely to respond to a treatment regimen that includes a DNA damaging agent, a PARP inhibitor, radiation, or a combination thereof. In turn, such a patient can be classified as likely to respond to a cancer treatment regimen that includes the use of one or more cancer treatment agents not associated with HDR, such as a taxane agent (e.g., doxetaxel, paclitaxel, abraxane), a growth factor or growth factor receptor inhibitor (e.g., erlotinib, gefitinib, lapatinib, sunitinib, bevacizumab, cetuximab, trastuzumab, panitumumab), and/or an antimetabolite agent (e.g., 5-flourouracil, methotrexate). In some embodiments, the patients are treatment naïve patients. Once classified as being likely to respond to a particular cancer treatment regimen (e.g., a cancer treatment regimen that includes the use of a cancer treatment agent not associated with HDR), the cancer patient can be treated with such a cancer treatment regimen. Any appropriate method for the cancer being treated can be used to treat a cancer patient identified as having cancer cells having a negative LOH signature status. Examples of information that can be used in addition to a negative LOH signature status to base a classification of being likely to respond to a particular cancer treatment regimen include, without limitation, previous treatment results, germline or somatic DNA mutations, gene or protein expression profiling (e.g., ER/PR/HER2 status, PSA levels), tumor histology (e.g., adenocarcinoma, squamous cell carcinoma, papillary serous carcinoma, mucinous carcinoma, invasive ductal carcinoma, ductal carcinoma in situ (non-invasive), etc.), disease stage, tumor or cancer grade (e.g., well, moderately, or poorly differentiated (e.g., Gleason, modified Bloom Richardson), etc.), number of previous courses of treatment, etc.

Once treated for a particular period of time (e.g., between one to six months), the patient can be assessed to determine whether or not the treatment regimen has an effect. If a beneficial effect is detected, the patient can continue with the same or a similar cancer treatment regimen. If a minimal or no beneficial effect is detected, then adjustments to the cancer treatment regimen can be made. For example, the dose, frequency of administration, or duration of treatment can be increased. In some cases, additional anti-cancer agents can be added to the treatment regimen or a particular anti-cancer agent can be replaced with one or more different anti-cancer agents. The patient being treated can continue to be monitored as appropriate, and changes can be made to the cancer treatment regimen as appropriate.

In addition to predicting likely treatment response or selecting desirable treatment regimens, an LOH signature can be used to determine a patient's prognosis. As shown in Example 3 below (particularly FIG. 18b), patients whose tumors have an LOH signature show significantly better survival than patients whose tumors do not have such an LOH signature. Thus, in one aspect, this document features a method for determining a patient's prognosis based at least in part of detecting the presence or absence of an LOH signature in a sample from the patient. The method comprises, or consists essentially of, (a) determining whether the patient comprises cancer cells having an LOH signature as described herein (e.g., wherein the presence of more than a reference number of LOH regions in at least one pair of human chromosomes of a cancer cell of the cancer patient that are longer than a first length but shorter than the length of the whole chromosome containing the LOH region indicates that the cancer cells have the LOH signature, wherein the at least one pair of human chromosomes is not a human X/Y sex chromosome pair, wherein the first length is about 1.5 or more megabases), and (b)(1) determining, based at least in part on the presence of the LOH signature, that the patient has a relatively good prognosis, or (b)(2) determining, based at least in part on the absence of the LOH signature, that the patient has a relatively poor prognosis. Prognosis may include the patient's likelihood of survival (e.g., progression-free survival, overall survival), wherein a relatively good prognosis would include an increased likelihood of survival as compared to some reference population (e.g., average patient with this patient's cancer type/subtype, average patient not having an LOH signature, etc.). Conversely, a relatively poor prognosis in terms of survival would include a decreased likelihood of survival as compared to some reference population (e.g., average patient with this patient's cancer type/subtype, average patient having an LOH signature, etc.).

As described herein, this document provides methods for assessing patients for cells (e.g., cancer cells) having a genome containing an LOH signature. In some embodiments, the patients are treatment naïve patients. For example, one or more clinicians or medical professionals can determine if a patient contains cancer cells having a genome containing an LOH signature. In some cases, one or more clinicians or medical professionals can determine if a patient contains cancer cells having a genome containing an LOH signature by obtaining a cancer cell sample from the patient and assessing the genome of cancer cells of the cancer cell sample to determine the presence or absence of an LOH signature as described herein.

In some cases, one or more clinicians or medical professionals can obtain a cancer cell sample from a patient and provide that sample to a testing laboratory having the ability to assess the genome of cancer cells of the cancer cell sample to provide an indication about the presence or absence of an LOH signature as described herein. In some embodiments, the patients are treatment naïve patients. In such cases, the one or more clinicians or medical professionals can determine if a patient contains cancer cells having a genome containing an LOH signature by receiving information about the presence or absence of an LOH signature directly or indirectly from the testing laboratory. For example, a testing laboratory, after assessing the genome of cancer cells for presence or absence of an LOH signature as described herein, can provide a clinician or medical professional with, or access to, a written, electronic, or oral report or medical record that provides an indication about the presence or absence of an LOH signature for a particular patient being assessed. Such a written, electronic, or oral report or medical record can allow the one or more clinicians or medical professionals to determine if a particular patient being assessed contains cancer cells having a genome containing an LOH signature.

Once a clinician or medical professional or group of clinicians or medical professionals determines that a particular patient being assessed contains cancer cells having a genome containing an LOH signature, the clinician or medical professional (or group) can classify that patient as having cancer cells whose genome contains the presence of an LOH signature. In some embodiments, the patients are treatment naïve patients. In some cases, a clinician or medical professional or group of clinicians or medical professionals can diagnose a patient determined to have cancer cells whose genome contains the presence of an LOH signature as having cancer cells likely to be deficient in HDR. Such a diagnosis can be based solely on a determination that a particular patient being assessed contains cancer cells having a genome containing an LOH signature or can be based at least in part on a determination that a particular patient being assessed contains cancer cells having a genome containing an LOH signature. For example, a patient determined to have cancer cells whose genome contains the presence of an LOH signature can be diagnosed as likely to be deficient in HDR based on the combination of a positive LOH signature status and deficient status in one or more tumor suppressor genes (e.g., BRCA1/2, RAD51C), a family history of cancer, or the presence of behavioral risk factors (e.g., smoking).

In some cases, a clinician or medical professional or group of clinicians or medical professionals can diagnose a patient determined to have cancer cells whose genome contains the presence of an LOH signature as having cancer cells likely to contain genetic mutations in one or more genes in the HDR pathway. In some embodiments, the patients are treatment naïve patients. Such a diagnosis can be based solely on a determination that a particular patient being assessed contains cancer cells having a genome containing an LOH signature or can be based at least in part on a determination that a particular patient being assessed contains cancer cells having a genome containing an LOH signature. For example, a patient determined to have cancer cells whose genome contains the presence of an LOH signature can be diagnosed as having cancer cells likely to contain genetic mutations in one or more genes in the HDR pathway based on the combination of a positive LOH positive status and a family history of cancer, or the presence of behavioral risk factors (e.g., smoking).

In some cases, a clinician or medical professional or group of clinicians or medical professionals can diagnose a patient determined to have cancer cells whose genome contains the presence of an LOH signature as having cancer cells likely to respond to a particular cancer treatment regimen. In some embodiments, the patients are treatment naïve patients. Such a diagnosis can be based solely on a determination that a particular patient being assessed contains cancer cells having a genome containing an LOH signature or can be based at least in part on a determination that a particular patient being assessed contains cancer cells having a genome containing an LOH signature. For example, a patient determined to have cancer cells whose genome contains the presence of an LOH signature can be diagnosed as being likely to respond to a particular cancer treatment regimen based on the combination of a positive LOH signature status and deficient status in one or more tumor suppressor genes (e.g., BRCA1/2, RAD51), a family history of cancer, or the presence of behavioral risk factors (e.g., smoking) As described herein, a patient determined to have cancer cells whose genome contains the presence of an LOH signature can be diagnosed as likely to respond to a cancer treatment regimen that includes the use of a platinum-based chemotherapy drug such as cisplatin, carboplatin, oxaliplatin, or picoplatin, an anthracycline such as epirubicin or doxorubicin, a topoisomerase I inhibitor such as campothecin, topotecan, or irinotecan, a PARP inhibitor, radiation, a combination thereof, or a combination of any of the preceding with another anti-cancer agent. In some embodiments, the patients are treatment naïve patients.

Once a clinician or medical professional or group of clinicians or medical professionals determines that a particular patient being assessed contains cancer cells having a genome lacking an LOH signature, the clinician or medical professional (or group) can classify that patient as having cancer cells whose genome contains an absence of an LOH signature. In some embodiments, the patients are treatment naïve patients. In some cases, a clinician or medical professional or group of clinicians or medical professionals can diagnose a patient determined to have cancer cells containing a genome that lacks the presence of an LOH signature as having cancer cells likely to have functional HDR. In some cases, a clinician or medical professional or group of clinicians or medical professionals can diagnose a patient determined to have cancer cells containing a genome that lacks the presence of an LOH signature as having cancer cells that do not likely contain genetic mutations in one or more genes in the HDR pathway. In some cases, a clinician or medical professional or group of clinicians or medical professionals can diagnose a patient determined to have cancer cells containing a genome that lacks the presence of an LOH signature or contains an increased number of LOH regions that cover the whole chromosome as having cancer cells that are less likely to respond to a platinum-based chemotherapy drug such as cisplatin, carboplatin, oxalaplatin, or picoplatin, an anthracycline such as epirubincin or doxorubicin, a topoisomerase I inhibitor such as campothecin, topotecan, or irinotecan, a PARP inhibitor, or radiation and/or more likely to respond to a cancer treatment regimen that includes the use of a cancer treatment agent not associated with HDR such as one or more taxane agents, growth factor or growth factor receptor inhibitors, anti-metabolite agents, etc. In some embodiments, the patients are treatment naïve patients.

As described herein, this document also provides methods for performing a diagnostic analysis of a nucleic acid sample (e.g., a genomic nucleic acid sample or amplified genomic nucleic acid sample) of a cancer patient to determine if cancer cells within the patient have a genome containing an LOH signature and/or an increased number of LOH regions that cover the whole chromosome. In some embodiments, the patients are treatment naïve patients. For example, one or more laboratory technicians or laboratory professionals can detect the presence or absence of an LOH signature in the genome of cancer cells of the patient or the presence or absence of an increased number of LOH regions that cover the whole chromosome in the genome of cancer cells of the patient. In some cases, one or more laboratory technicians or laboratory professionals can detect the presence or absence of an LOH signature or the presence or absence of an increased number of LOH regions that cover the whole chromosome in the genome of cancer cells of the patient by (a) receiving a cancer cell sample obtained from the patient, receiving a genomic nucleic acid sample obtained from cancer cells obtained from the patient, or receiving an enriched and/or amplified genomic nucleic acid sample obtained from cancer cells obtained from the patient and (b) performing an analysis (e.g., a SNP array-based assay or a sequencing-based assay) using the received material to detect the presence or absence of an LOH signature or the presence or absence of an increased number of LOH regions that cover the whole chromosome as described herein. In some cases, one or more laboratory technicians or laboratory professionals can receive a sample to be analyzed (e.g., a cancer cell sample obtained from the patient, a genomic nucleic acid sample obtained from cancer cells obtained from the patient, or an enriched and/or amplified genomic nucleic acid sample obtained from cancer cells obtained from the patient) directly or indirectly from a clinician or medical professional. In some embodiments, the patients are treatment naïve patients.

Once a laboratory technician or laboratory professional or group of laboratory technicians or laboratory professionals detects the presence of an LOH signature as described herein, the laboratory technician or laboratory professional (or group) can identify the patient whose cancer cells were detected as having an LOH signature as having cancer cells with a positive LOH signature status. For example, one or more laboratory technicians or laboratory professionals can identify a patient having cancer cells that were detected to have an LOH signature as having cancer cells with a positive LOH signature status by associating that positive LOH signature status or the result (or results or a summary of results) of the performed diagnostic analysis with the corresponding patient's name, medical record, symbolic/numerical identifier, or a combination thereof. In some cases, a laboratory technician or laboratory professional or group of laboratory technicians or laboratory professionals can identify a patient having cancer cells that were detected to have an LOH signature as having cancer cells potentially deficient in HDR by associating the positive LOH signature status, the potentially deficient in HDR status, or the result (or results or a summary of results) of the performed diagnostic analysis with the corresponding patient's name, medical record, symbolic/numerical identifier, or a combination thereof. Such identification can be based solely on detecting the presence of an LOH signature or can be based at least in part on detecting the presence of an LOH signature. For example, a laboratory technician or laboratory professional can identify a patient having cancer cells that were detected to have an LOH signature as having cancer cells potentially deficient in HDR based on a combination of a positive LOH signature status and the results of other genetic and biochemical tests performed at the testing laboratory. In some embodiments, the patients are treatment naïve patients.

In some cases, a laboratory technician or laboratory professional or group of laboratory technicians or laboratory professionals can identify a patient having cancer cells that were detected to have an LOH signature as having cancer cells potentially containing a genetic mutation in one or more genes in the HDR pathway by associating the positive LOH signature status, the potential presence of a genetic mutation in one or more genes in the HDR pathway, or the result (or results or a summary of results) of the performed diagnostic analysis with the corresponding patient's name, medical record, symbolic/numerical identifier, or a combination thereof. Such identification can be based solely on detecting the presence of an LOH signature or can be based at least in part on detecting the presence of an LOH signature. For example, a laboratory technician or laboratory professional can identify a patient having cancer cells that were detected to have an LOH signature as having cancer cells potentially containing a genetic mutation in one or more genes in the HDR pathway based on a combination of a positive LOH signature status and the results of other genetic and biochemical tests performed at the testing laboratory. In some embodiments, the patients are treatment naïve patients.

In some cases, a laboratory technician or laboratory professional or group of laboratory technicians or laboratory professionals can identify a patient having cancer cells that were detected to have an LOH signature as having cancer cells likely to respond to a particular cancer treatment regimen by associating the positive LOH signature status, a potentially deficient HDR status, a potential presence of a deficient status in one or more genes in the HDR pathway, or the result (or results or a summary of results) of the performed diagnostic analysis with the corresponding patient's name, medical record, symbolic/numerical identifier, or a combination thereof. Such identification can be based solely on detecting the presence of an LOH signature or can be based at least in part on detecting the presence of an LOH signature. For example, a laboratory technician or laboratory professional can identify a patient having cancer cells that were detected to have an LOH signature as having cancer cells likely to respond to a particular cancer treatment regimen based on a combination of a positive LOH signature status and the results of other genetic and biochemical tests performed at the testing laboratory. In some embodiments, the patients are treatment naïve patients.

Once a laboratory technician or laboratory professional or group of laboratory technicians or laboratory professionals detects the absence of an LOH signature, the laboratory technician or laboratory professional (or group) can identify the patient whose cancer cells were detected as lacking an LOH signature as having cancer cells with a negative LOH signature status. For example, one or more laboratory technicians or laboratory professionals can identify a patient having cancer cells that were detected to lack an LOH signature as having cancer cells with a negative LOH signature status by associating that negative LOH signature status or the result (or results or a summary of results) of the performed diagnostic analysis with the corresponding patient's name, medical record, symbolic/numerical identifier, or a combination thereof. In some cases, a laboratory technician or laboratory professional or group of laboratory technicians or laboratory professionals can identify a patient having cancer cells that were detected to lack an LOH signature as having cancer cells with potentially intact HDR by associating the negative LOH signature status, the potentially intact HDR status, or the result (or results or a summary of results) of the performed diagnostic analysis with the corresponding patient's name, medical record, symbolic/numerical identifier, or a combination thereof. In some embodiments, the patients are treatment naïve patients.

In some cases, a laboratory technician or laboratory professional or group of laboratory technicians or laboratory professionals can identify a patient having cancer cells that were detected to lack an LOH signature as having cancer cells with potentially intact genes of the HDR pathway by associating the negative LOH signature status, the potential absence of genetic mutations in genes of the HDR pathway, or the result (or results or a summary of results) of the performed diagnostic analysis with the corresponding patient's name, medical record, symbolic/numerical identifier, or a combination thereof. In some embodiments, the patients are treatment naïve patients.

In some cases, a laboratory technician or laboratory professional or group of laboratory technicians or laboratory professionals can identify a patient having cancer cells that were detected to lack an LOH signature as having cancer cells as less likely to respond to one particular treatment (e.g., a platinum-based chemotherapy drug such as cisplatin, carboplatin, oxaliplatin, or picoplatin, an anthracycline such as epirubincin or doxorubicin, a topoisomerase I inhibitor such as campothecin, topotecan, or irinotecan, a PARP inhibitor such as iniparib, olaparib, or velapirib, or radiation) and/or more likely to respond to a particular cancer treatment regimen (e.g., a cancer treatment regimen that includes the use of a cancer treatment agent not associated with HDR) by associating the negative LOH signature status, a potentially intact HDR status, a potential absence of genetic mutations in genes of the HDR pathway, or the result (or results or a summary of results) of the performed diagnostic analysis with the corresponding patient's name, medical record, symbolic/numerical identifier, or a combination thereof. In some embodiments, the patients are treatment naïve patients.

Once a laboratory technician or laboratory professional or group of laboratory technicians or laboratory professionals detects the presence of an increased number of LOH regions that cover the whole chromosome, the laboratory technician or laboratory professional (or group) can identify the patient whose cancer cells were detected as having an increased number of LOH regions that cover the whole chromosome as likely having cancer cells with an intact BRCA1, BRCA2 and/or RAD51C status, or intact HDR pathway. For example, one or more laboratory technicians or laboratory professionals can identify a patient having cancer cells that were detected to have an increased number of LOH regions that cover the whole chromosome as likely having cancer cells with an intact BRCA1 and BRCA2 status by associating the presence of an increased number of LOH regions that cover the whole chromosome or the result (or results or a summary of results) of the performed diagnostic analysis with the corresponding patient's name, medical record, symbolic/numerical identifier, or a combination thereof. In some embodiments, the patients are treatment naïve patients.

The results of any analyses according to the invention will often be communicated to physicians, genetic counselors and/or patients (or other interested parties such as researchers) in a transmittable form that can be communicated or transmitted to any of the above parties. Such a form can vary and can be tangible or intangible. The results can be embodied in descriptive statements, diagrams, photographs, charts, images or any other visual forms. For example, graphs or diagrams showing genotype or LOH (or HRD status) information can be used in explaining the results. The statements and visual forms can be recorded on a tangible medium such as papers, computer readable media such as floppy disks, compact disks, flash memory, etc., or in an intangible medium, e.g., an electronic medium in the form of email or website on internet or intranet. In addition, results can also be recorded in a sound form and transmitted through any suitable medium, e.g., analog or digital cable lines, fiber optic cables, etc., via telephone, facsimile, wireless mobile phone, internet phone and the like.

Thus, the information and data on a test result can be produced anywhere in the world and transmitted to a different location. As an illustrative example, when an assay is conducted outside the United States, the information and data on a test result may be generated, cast in a transmittable form as described above, and then imported into the United States. Accordingly, the present invention also encompasses a method for producing a transmittable form of information on an LOH signature for at least one patient sample. The method comprises the steps of (1) determining an LOH signature according to methods of the present invention; and (2) embodying the result of the determining step in a transmittable form. The transmittable form is a product of such a method.

Several embodiments of the invention described herein involve a step of correlating an LOH signature according to the present invention (e.g., the total number of LOH regions in at least one pair of human chromosomes of said cancer cell that are longer than a first length but shorter than the length of the whole chromosome containing the LOH region, wherein said at least one pair of human chromosomes is not a human X/Y sex chromosome pair, wherein said first length is about 1.5 or more megabases) to a particular clinical feature (e.g., an increased likelihood of a deficiency in the BRCA1 or BRCA2 gene; an increased likelihood of HDR deficiency; an increased likelihood of response to a treatment regimen comprising a DNA damaging agent, an anthracycline, a topoisomerase I inhibitor, radiation, and/or a PARP inhibitor; etc.) if the number is greater than some reference (or optionally to another feature if the number is less than some reference). Throughout this document, wherever such an embodiment is described, another embodiment of the invention may involve, in addition to or instead of a correlating step, one or both of the following steps: (a) concluding that the patient has the clinical feature based at least in part on the presence or absence of the LOH signature; or (b) communicating that the patient has the clinical feature based at least in part on the presence or absence of the LOH signature.

By way of illustration, but not limitation, one embodiment described in this document is a method of predicting a cancer patient's response to a cancer treatment regimen comprising a DNA damaging agent, an anthracycline, a topoisomerase I inhibitor, radiation, and/or a PARP inhibitor, said method comprising: (1) determining, in a cancer cell from said cancer patient, the number of LOH regions in at least one pair of human chromosomes of a cancer cell of said cancer patient that are longer than a first length but shorter than the length of the whole chromosome containing the LOH region, wherein said at least one pair of human chromosomes is not a human X/Y sex chromosome pair, wherein said first length is about 1.5 or more megabases; and (2) correlating said total number that is greater than a reference number with an increased likelihood that said cancer patient will respond to said cancer treatment regimen. According to the preceding paragraph, this description of this embodiment is understood to include a description of two related embodiments, i.e., a method of predicting a cancer patient's response to a cancer treatment regimen comprising a DNA damaging agent, an anthracycline, a topoisomerase I inhibitor, radiation, and/or a PARP inhibitor, said method comprising: (1) determining, in a cancer cell from said cancer patient, the number of LOH regions in at least one pair of human chromosomes of a cancer cell of said cancer patient that are longer than a first length but shorter than the length of the whole chromosome containing the LOH region, wherein said at least one pair of human chromosomes is not a human X/Y sex chromosome pair, wherein said first length is about 1.5 or more megabases; and (2)(a) concluding that said patient has an increased likelihood that said cancer patient will respond to said cancer treatment regimen based at least in part on a total number that is greater than a reference number; or (2)(b) communicating that said patient has an increased likelihood that said cancer patient will respond to said cancer treatment regimen based at least in part on a total number that is greater than a reference number.

In each embodiment described in this document involving correlating a particular assay or analysis output (e.g., total number of LOH regions greater than a reference number, etc.) to some likelihood (e.g., increased, not increased, decreased, etc.) of some clinical feature (e.g., response to a particular treatment, cancer-specific death, etc.), or additionally or alternatively concluding or communicating such clinical feature based at least in part on such particular assay or analysis output, such correlating, concluding or communicating may comprise assigning a risk or likelihood of the clinical feature occurring based at least in part on the particular assay or analysis output. In some embodiments, such risk is a percentage probability of the event or outcome occurring. In some embodiments, the patient is assigned to a risk group (e.g., low risk, intermediate risk, high risk, etc.). In some embodiments "low risk" is any percentage probability below 5%, 10%, 15%, 20%, 25%, 30%, 35%, 40%, 45%, or 50%. In some embodiments "intermediate risk" is any percentage probability above 5%, 10%, 15%, 20%, 25%, 30%, 35%, 40%, 45%, or 50% and below 15%, 20%, 25%, 30%, 35%, 40%, 45%, 50%, 55%, 60%, 65%, 70%, or 75%. In some embodiments "high risk" is any percentage probability above 25%, 30%, 35%, 40%, 45%, 50%, 55%, 60%, 65%, 70%, 75%, 80%, 85%, 90%, 95%, or 99%.

As used herein, "communicating" a particular piece of information means to make such information known to another person or transfer such information to a thing (e.g., a computer). In some methods of the invention, a patient's prognosis or likelihood of response to a particular treatment is communicated. In some embodiments, the information used to arrive at such a prognosis or response prediction (e.g., LOH signature according to the present invention, etc.) is communicated. This communication may be auditory (e.g., verbal), visual (e.g., written), electronic (e.g., data transferred from one computer system to another), etc. In some embodiments, communicating a cancer classification (e.g., prognosis, likelihood of response, appropriate treatment, etc.) comprises generating a report that communicates the cancer classification. In some embodiments the report is a paper report, an auditory report, or an electronic record. In some embodiments the report is displayed and/or stored on a computing device (e.g., handheld device, desktop computer, smart device, website, etc.). In some embodiments the cancer classification is communicated to a physician (e.g., a report communicating the classification is provided to the physician). In some embodiments the cancer classification is communicated to a patient (e.g., a report communicating the classification is provided to the patient). Communicating a cancer classification can also be accomplished by transferring information (e.g., data) embodying the classification to a server computer and allowing an intermediary or end-user to access such information (e.g., by viewing the information as displayed from the server, by downloading the information in the form of one or more files transferred from the server to the intermediary or end-user's device, etc.).

Wherever an embodiment of the invention comprises concluding some fact (e.g., a patient's prognosis or a patient's likelihood of response to a particular treatment regimen), this may include in some embodiments a computer program concluding such fact, typically after performing an algorithm that applies information on LOH regions according to the present invention.

In each embodiment described herein involving a number of LOH regions (e.g., LOH Indicator Regions) or a total combined length of such LOH regions, the present invention encompasses a related embodiment involving a test value or score (e.g., HRD score, LOH score, etc.) derived from, incorporating, and/or, at least to some degree, reflecting such number or length. In other words, the bare LOH region numbers or lengths need not be used in the various methods, systems, etc. of the invention; a test value or score derived from such numbers or lengths may be used. For example, one embodiment of the invention provides a method of treating cancer in a patient, comprising: (1) determining in a sample from said patient the number of LOH regions in at least one pair of human chromosomes of a cancer cell of the cancer patient that are longer than a first length but shorter than the length of the whole chromosome containing the LOH region indicates that the cancer cells have the LOH signature, wherein the at least one pair of human chromosomes is not a human X/Y sex chromosome pair, wherein the first length is about 1.5 or more megabases; (2) providing a test value derived from the number of said LOH regions; (3) comparing said test value to one or more reference values derived from the number of said LOH regions in a reference population (e.g., mean, median, terciles, quartiles, quintiles, etc.); and (4)(a) administering to said patient an anti-cancer drug, or recommending or prescribing or initiating a treatment regimen comprising chemotherapy and/or a synthetic lethality agent based at least in part on said comparing step revealing that the test value is greater (e.g., at least 2-, 3-, 4-, 5-, 6-, 7-, 8-, 9-, or 10-fold greater; at least 1, 2, 3, 4, 5, 6, 7, 8, 9, or 10 standard deviations greater) than at least one said reference value; or (4)(b) recommending or prescribing or initiating a treatment regimen not comprising chemotherapy and/or a synthetic lethality agent based at least in part on said comparing step revealing that the test value is not greater (e.g., not more than 2-, 3-, 4-, 5-, 6-, 7-, 8-, 9-, or 10-fold greater; not more than 1, 2, 3, 4, 5, 6, 7, 8, 9, or 10 standard deviations greater) than at least one said reference value. The invention encompasses, mutatis mutandis, corresponding embodiments where the test value or score is used to determine the patient's prognosis, the patient's likelihood of response to a particular treatment regimen, the patient's or patient's sample's likelihood of having a BRCA1, BRCA2, RAD51C or HDR deficiency, etc.

Figure 15:
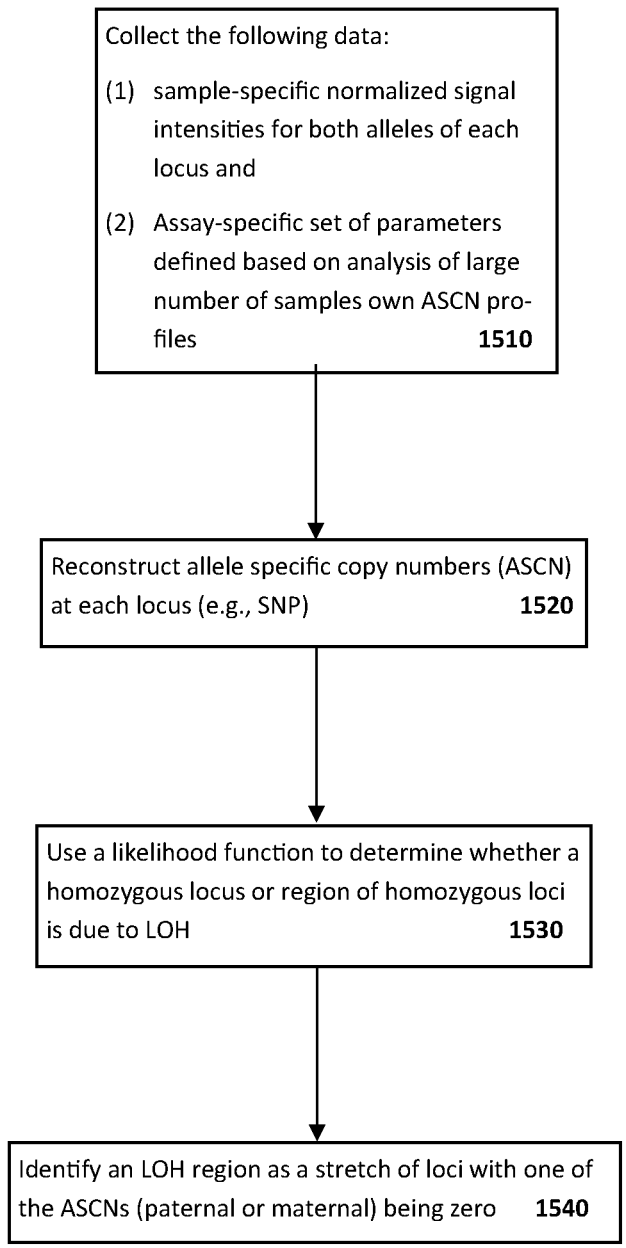
FIG. 15 is a flow chart of an example computational process for identifying LOH loci and regions.

FIG. 15 shows an exemplary process by which a computing system (or a computer program (e.g., software) containing computer-executable instructions) can identify LOH loci or regions from genotype data as described herein. If the observed ratio of the signals of two alleles, A and B, is two to one, there are two possibilities. The first possibility is that cancer cells have LOH with deletion of allele B in a sample with 50% contamination with normal cells. The second possibility is that there is no LOH but allele A is duplicated in a sample with no contamination with normal cells. The process begins at box 1500, where the following data are collected by the computing system; (1) sample-specific normalized signal intensities for both alleles of each locus and (2) assay-specific (specific for different SNP arrays and for sequence based approach) set of parameters defined based on analysis of large number of samples with known ASCN profiles. As described herein, any appropriate assay such as a SNP array-based assay or sequencing-based assay can be used to assess loci along a chromosome for homozygosity or heterozygosity. In some cases, a system including a signal detector and a computer can be used to collect data (e.g., fluorescent signals or sequencing results) regarding the homozygous or heterozygous nature of the plurality of loci (e.g., sample-specific normalized signal intensities for both alleles of each locus). At box 1510, allele specific copy numbers (ASCN) are reconstructed at each locus (e.g., each SNP). ASCNs are the numbers of copies of both paternal and maternal alleles. At box 1530, a likelihood function is used to determine whether a homozygous locus or region of homozygous loci is due to LOH. This can be conceptually analogous to a previously described algorithm designed to reconstruct total copy number (rather than ASCN) at each locus (e.g., SNP). See International Application No. PCT/US2011/026098 to Abkevich et al. The likelihood function can be maximized over ASCN of all loci, level of contamination with benign tissue, total copy number averaged over the whole genome, and sample specific noise level. At box 1540, an LOH region is determined as a stretch of SNPs with one of the ASCNs (paternal or maternal) being zero. In some embodiments, the computer process further comprises a step of inquiring or determining whether a patient is treatment naïve.

Figure 3:
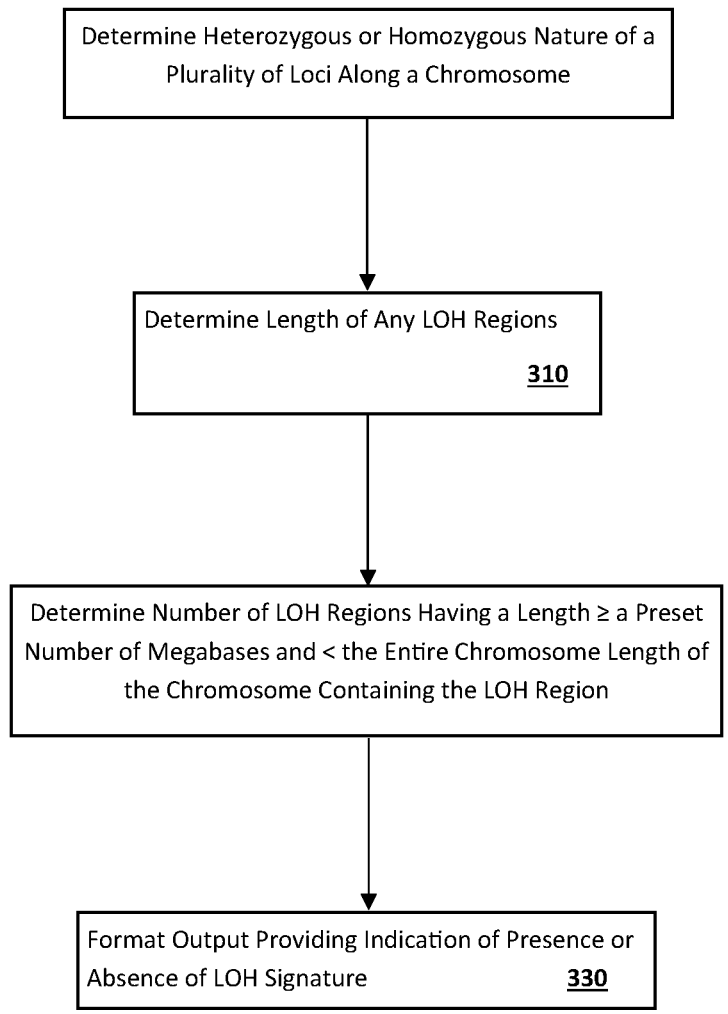
FIG. 3 is a flow chart of an example process for assessing the genome of a cell (e.g., a cancer cell) for an LOH signature.

FIG. 3 shows an exemplary process by which a computing system can determine the presence or absence of an LOH signature. The process begins at box 300, where data regarding the homozygous or heterozygous nature of a plurality of loci along a chromosome is collected by the computing system. As described herein, any appropriate assay such as a SNP array-based assay or sequencing-based assay can be used to assess loci along a chromosome for homozygosity or heterozygosity. In some cases, a system including a signal detector and a computer can be used to collect data (e.g., fluorescent signals or sequencing results) regarding the homozygous or heterozygous nature of the plurality of loci. At box 310, data regarding the homozygous or heterozygous nature of a plurality of loci as well as the location or spatial relationship of each locus is assessed by the computing system to determine the length of any LOH regions present along a chromosome. At box 320, data regarding the number of LOH regions detected and the length of each detected LOH region is assessed by the computing system to determine the number of LOH regions that have a length (a) greater than or equal to a preset number of Mb (e.g., 15 Mb) and (b) less than the entire length of the chromosome containing that LOH region. Alternatively the computing system can determine the total or combined LOH length as described above. At box 330, the computing system formats an output providing an indication of the presence or absence of an LOH signature. Once formatted, the computing system can present the output to a user (e.g., a laboratory technician, clinician, or medical professional). As described herein, the presence or absence of an LOH signature can be used to provide an indication about a patient's likely HDR status, an indication about the likely presence or absence of genetic mutations in genes of the HDR pathway, and/or an indication about possible cancer treatment regimens.

Figure 4:
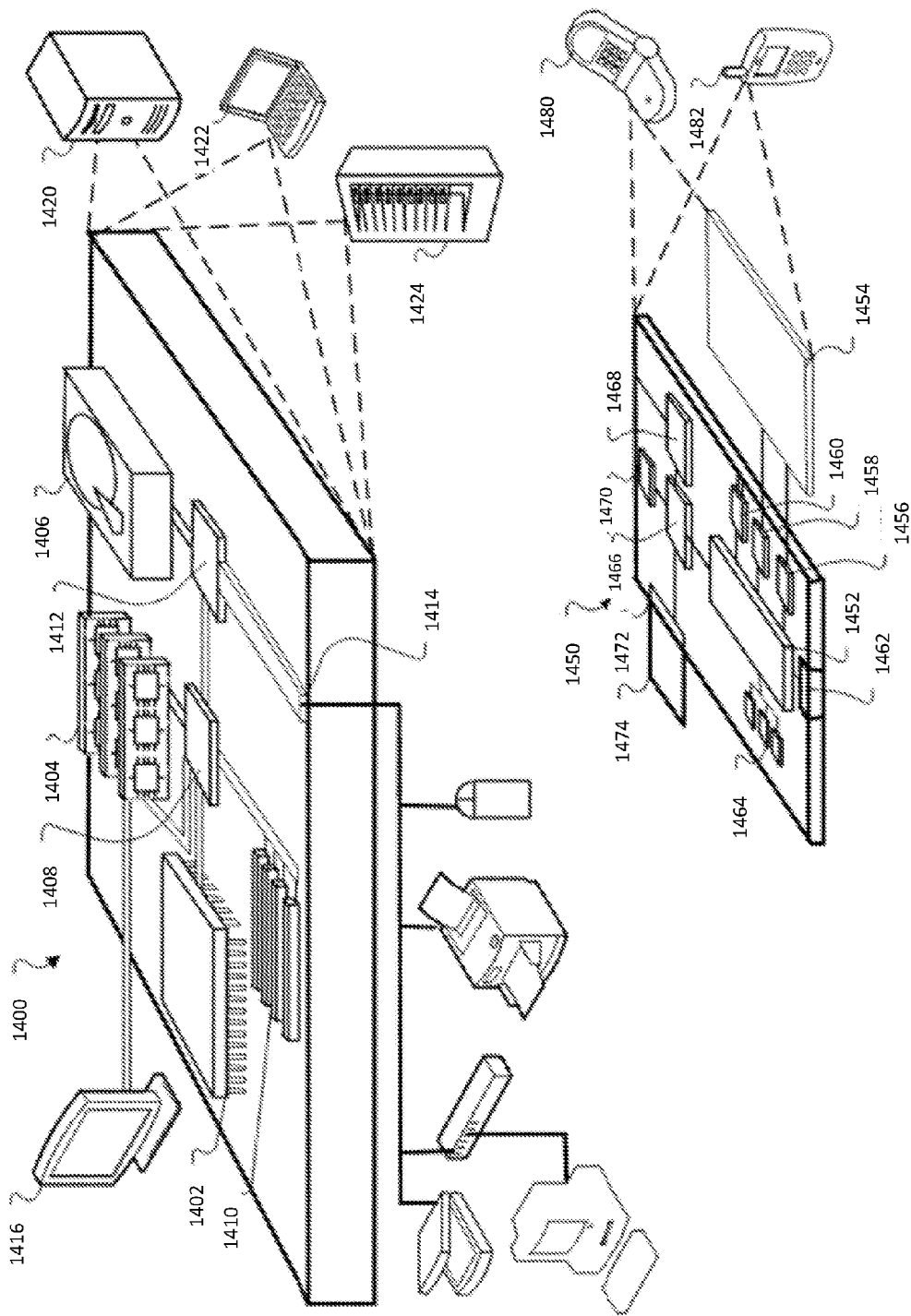
FIG. 4 is a diagram of an example of a computer device and a mobile computer device that can be used to implement the techniques described herein.

FIG. 4 is a diagram of an example of a computer device 1400 and a mobile computer device 1450, which may be used with the techniques described herein. Computing device 1400 is intended to represent various forms of digital computers, such as laptops, desktops, workstations, personal digital assistants, servers, blade servers, mainframes, and other appropriate computers. Computing device 1450 is intended to represent various forms of mobile devices, such as personal digital assistants, cellular telephones, smart phones, and other similar computing devices. The components shown here, their connections and relationships, and their functions, are meant to be exemplary only, and are not meant to limit implementations of the inventions described and/or claimed in this document.

Computing device 1400 includes a processor 1402, memory 1404, a storage device 1406, a high-speed interface 1408 connecting to memory 1404 and high-speed expansion ports 1410, and a low speed interface 1415 connecting to low speed bus 1414 and storage device 1406. Each of the components 1402, 1404, 1406, 1408, 1410, and 1415, are interconnected using various busses, and may be mounted on a common motherboard or in other manners as appropriate. The processor 1402 can process instructions for execution within the computing device 1400, including instructions stored in the memory 1404 or on the storage device 1406 to display graphical information for a GUI on an external input/output device, such as display 1416 coupled to high speed interface 1408. In other implementations, multiple processors and/or multiple buses may be used, as appropriate, along with multiple memories and types of memory. Also, multiple computing devices 1400 may be connected, with each device providing portions of the necessary operations (e.g., as a server bank, a group of blade servers, or a multi-processor system).

The memory 1404 stores information within the computing device 1400. In one implementation, the memory 1404 is a volatile memory unit or units. In another implementation, the memory 1404 is a non-volatile memory unit or units. The memory 1404 may also be another form of computer-readable medium, such as a magnetic or optical disk.

The storage device 1406 is capable of providing mass storage for the computing device 1400. In one implementation, the storage device 1406 may be or contain a computer-readable medium, such as a floppy disk device, a hard disk device, an optical disk device, or a tape device, a flash memory or other similar solid state memory device, or an array of devices, including devices in a storage area network or other configurations. A computer program product can be tangibly embodied in an information carrier. The computer program product may also contain instructions that, when executed, perform one or more methods, such as those described herein. The information carrier is a computer- or machine-readable medium, such as the memory 1404, the storage device 1406, memory on processor 1402, or a propagated signal.

The high speed controller 1408 manages bandwidth-intensive operations for the computing device 1400, while the low speed controller 1415 manages lower bandwidth-intensive operations. Such allocation of functions is exemplary only. In one implementation, the high-speed controller 1408 is coupled to memory 1404, display 1416 (e.g., through a graphics processor or accelerator), and to high-speed expansion ports 1410, which may accept various expansion cards (not shown). In the implementation, low-speed controller 1415 is coupled to storage device 1406 and low-speed expansion port 1414. The low-speed expansion port, which may include various communication ports (e.g., USB, Bluetooth, Ethernet, or wireless Ethernet) may be coupled to one or more input/output devices, such as a keyboard, a pointing device, a scanner, an optical reader, a fluorescent signal detector, or a networking device such as a switch or router, e.g., through a network adapter.

The computing device 1400 may be implemented in a number of different forms, as shown in the figure. For example, it may be implemented as a standard server 1420, or multiple times in a group of such servers. It may also be implemented as part of a rack server system 1424. In addition, it may be implemented in a personal computer such as a laptop computer 1422. Alternatively, components from computing device 1400 may be combined with other components in a mobile device (not shown), such as device 1450. Each of such devices may contain one or more of computing device 1400, 1450, and an entire system may be made up of multiple computing devices 1400, 1450 communicating with each other.

Computing device 1450 includes a processor 1452, memory 1464, an input/output device such as a display 1454, a communication interface 1466, and a transceiver 1468, among other components (e.g., a scanner, an optical reader, a fluorescent signal detector). The device 1450 may also be provided with a storage device, such as a microdrive or other device, to provide additional storage. Each of the components 1450, 1452, 1464, 1454, 1466, and 1468, are interconnected using various buses, and several of the components may be mounted on a common motherboard or in other manners as appropriate.

The processor 1452 can execute instructions within the computing device 1450, including instructions stored in the memory 1464. The processor may be implemented as a chipset of chips that include separate and multiple analog and digital processors. The processor may provide, for example, for coordination of the other components of the device 1450, such as control of user interfaces, applications run by device 1450, and wireless communication by device 1450.

Processor 1452 may communicate with a user through control interface 1458 and display interface 1456 coupled to a display 1454. The display 1454 may be, for example, a TFT LCD (Thin-Film-Transistor Liquid Crystal Display) or an OLED (Organic Light Emitting Diode) display, or other appropriate display technology. The display interface 1456 may comprise appropriate circuitry for driving the display 1454 to present graphical and other information to a user. The control interface 1458 may receive commands from a user and convert them for submission to the processor 1452. In addition, an external interface 1462 may be provide in communication with processor 1452, so as to enable near area communication of device 1450 with other devices. External interface 1462 may provide, for example, for wired communication in some implementations, or for wireless communication in other implementations, and multiple interfaces may also be used.

The memory 1464 stores information within the computing device 1450. The memory 1464 can be implemented as one or more of a computer-readable medium or media, a volatile memory unit or units, or a non-volatile memory unit or units. Expansion memory 1474 may also be provided and connected to device 1450 through expansion interface 1472, which may include, for example, a SIMM (Single In Line Memory Module) card interface. Such expansion memory 1474 may provide extra storage space for device 1450, or may also store applications or other information for device 1450. For example, expansion memory 1474 may include instructions to carry out or supplement the processes described herein, and may include secure information also. Thus, for example, expansion memory 1474 may be provide as a security module for device 1450, and may be programmed with instructions that permit secure use of device 1450. In addition, secure applications may be provided via the SIMM cards, along with additional information, such as placing identifying information on the SIMM card in a non-hackable manner.

The memory may include, for example, flash memory and/or NVRAM memory, as discussed below. In one implementation, a computer program product is tangibly embodied in an information carrier. The computer program product contains instructions that, when executed, perform one or more methods, such as those described herein. The information carrier is a computer- or machine-readable medium, such as the memory 1464, expansion memory 1474, memory on processor 1452, or a propagated signal that may be received, for example, over transceiver 1468 or external interface 1462.

Device 1450 may communicate wirelessly through communication interface 1466, which may include digital signal processing circuitry where necessary. Communication interface 1466 may provide for communications under various modes or protocols, such as GSM voice calls, SMS, EMS, or MMS messaging, CDMA, TDMA, PDC, WCDMA, CDMA2000, or GPRS, among others. Such communication may occur, for example, through radio-frequency transceiver 1468. In addition, short-range communication may occur, such as using a Bluetooth, WiFi, or other such transceiver (not shown). In addition, GPS (Global Positioning System) receiver module 1470 may provide additional navigation- and location-related wireless data to device 1450, which may be used as appropriate by applications running on device 1450.

Device 1450 may also communicate audibly using audio codec 1460, which may receive spoken information from a user and convert it to usable digital information. Audio codec 1460 may likewise generate audible sound for a user, such as through a speaker, e.g., in a handset of device 1450. Such sound may include sound from voice telephone calls, may include recorded sound (e.g., voice messages, music files, etc.) and may also include sound generated by applications operating on device 1450.

The computing device 1450 may be implemented in a number of different forms, as shown in the figure. For example, it may be implemented as a cellular telephone 1480. It may also be implemented as part of a smartphone 1482, personal digital assistant, or other similar mobile device.

Various implementations of the systems and techniques described herein can be realized in digital electronic circuitry, integrated circuitry, specially designed ASICs (application specific integrated circuits), computer hardware, firmware, software, and/or combinations thereof. These various implementations can include implementation in one or more computer programs that are executable and/or interpretable on a programmable system including at least one programmable processor, which may be special or general purpose, coupled to receive data and instructions from, and to transmit data and instructions to, a storage system, at least one input device, and at least one output device.

These computer programs (also known as programs, software, software applications or code) include machine instructions for a programmable processor, and can be implemented in a high-level procedural and/or object-oriented programming language, and/or in assembly/machine language. As used herein, the terms "machine-readable medium" and "computer-readable medium" refer to any computer program product, apparatus and/or device (e.g., magnetic discs, optical disks, memory, and Programmable Logic Devices (PLDs)) used to provide machine instructions and/or data to a programmable processor, including a machine-readable medium that receives machine instructions as a machine-readable signal. The term "machine-readable signal" refers to any signal used to provide machine instructions and/or data to a programmable processor.

To provide for interaction with a user, the systems and techniques described herein can be implemented on a computer having a display device (e.g., a CRT (cathode ray tube) or LCD (liquid crystal display) monitor) for displaying information to the user and a keyboard and a pointing device (e.g., a mouse or a trackball) by which the user can provide input to the computer. Other kinds of devices can be used to provide for interaction with a user as well; for example, feedback provided to the user can be any form of sensory feedback (e.g., visual feedback, auditory feedback, or tactile feedback); and input from the user can be received in any form, including acoustic, speech, or tactile input.

The systems and techniques described herein can be implemented in a computing system that includes a back end component (e.g., as a data server), or that includes a middleware component (e.g., an application server), or that includes a front end component (e.g., a client computer having a graphical user interface or a Web browser through which a user can interact with an implementation of the systems and techniques described herein), or any combination of such back end, middleware, or front end components. The components of the system can be interconnected by any form or medium of digital data communication (e.g., a communication network). Examples of communication networks include a local area network ("LAN"), a wide area network ("WAN"), and the Internet.

The computing system can include clients and servers. A client and server are generally remote from each other and typically interact through a communication network. The relationship of client and server arises by virtue of computer programs running on the respective computers and having a client-server relationship to each other.

In some cases, a computing system provided herein can be configured to include one or more sample analyzers. A sample analyzer can be configured to produce a plurality of signals about genomic DNA of at least one pair of human chromosomes of a cancer cell. For example, a sample analyzer can produce signals that are capable of being interpreted in a manner that identifies the homozygous or heterozygous nature of loci along a chromosome. In some cases, a sample analyzer can be configured to carry out one or more steps of a SNP array-based assay or sequencing-based assay and can be configured to produce and/or capture signals from such assays. In some cases, a computing system provided herein can be configured to include a computing device. In such cases, the computing device can be configured to receive signals from a sample analyzer. The computing device can include computer-executable instructions or a computer program (e.g., software) containing computer-executable instructions for carrying out one or more of the methods or steps described herein. In some cases, such computer-executable instructions can instruct a computing device to analyze signals from a sample analyzer, from another computing device, from a SNP array-based assay, or from a sequencing-based assay. The analysis of such signals can be carried out to determine genotypes, homozygosity at certain loci, regions of homozygosity, the number of LOH regions, to determine the size of LOH regions, to determine the number of LOH regions having a particular size or range of sizes, to determine whether or not a sample is positive for an LOH signature, to determine the number of Indicator LOH Regions in at least one pair of human chromosomes, to determine a likelihood of a deficiency in BRCA1 and/or BRCA2 genes, to determine a likelihood of a deficiency in HDR, to determine a likelihood that a cancer patient will respond to a particular cancer treatment regimen (e.g., a regimen that includes a DNA damaging agent, an anthracycline, a topoisomerase I inhibitor, radiation, a PARP inhibitor, or a combination thereof), or to determine a combination of these items.

In some cases, a computing system provided herein can include computer-executable instructions or a computer program (e.g., software) containing computer-executable instructions for formatting an output providing an indication about the number of LOH regions, the size of LOH regions, the number of LOH regions having a particular size or range of sizes, whether or not a sample is positive for an LOH signature, the number of Indicator LOH Regions in at least one pair of human chromosomes, a likelihood of a deficiency in BRCA1 and/or BRCA2 genes, a likelihood of a deficiency in HDR, a likelihood that a cancer patient will respond to a particular cancer treatment regimen (e.g., a regimen that includes a DNA damaging agent, an anthracycline, a topoisomerase I inhibitor, radiation, a PARP inhibitor, or a combination thereof), or a combination of these items. In some cases, a computing system provided herein can include computer-executable instructions or a computer program (e.g., software) containing computer-executable instructions for determining a desired cancer treatment regimen for a particular patient based at least in part on the presence or absence of an LOH signature or on the number of Indicator LOH Regions.

In some cases, a computing system provided herein can include a pre-processing device configured to process a sample (e.g., cancer cells) such that a SNP array-based assay or sequencing-based assay can be performed. Examples of pre-processing devices include, without limitation, devices configured to enrich cell populations for cancer cells as opposed to non-cancer cells, devices configured to lyse cells and/or extract genomic nucleic acid, and devices configured to enrich a sample for particular genomic DNA fragments.

This document also provides kits for assessing samples (e.g., cancer cells) as described herein. For example, this document provides kits for assessing cancer cells for the presence of an LOH signature or to determine the number of Indicator LOH Regions in at least one pair of human chromosomes. A kit provided herein can include either SNP probes (e.g., an array of SNP probes for carrying out a SNP array-based assay described herein) or primers (e.g., primers designed for sequencing SNP regions via a sequencing-based assay) in combination with a computer program product containing computer-executable instructions for carrying out one or more of the methods or steps described herein (e.g., computer-executable instructions for determining the number of LOH regions having a particular size or range of sizes). In some cases, a kit provided herein can include at least 500, 1000, 10,000, 25,000, or 50,000 SNP probes capable of hybridizing to polymorphic regions of human genomic DNA. In some cases, a kit provided herein can include at least 500, 1000, 10,000, 25,000, or 50,000 primers capable of sequencing polymorphic regions of human genomic DNA. In some cases, a kit provided herein can include one or more other ingredients for performing a SNP array-based assay or a sequencing-based assay. Examples of such other ingredients include, without limitation, buffers, sequencing nucleotides, enzymes (e.g., polymerases), etc. This document also provides the use of any appropriate number of the materials provided herein in the manufacture of a kit for carrying out one or more of the methods or steps described herein. For example, this document provides the use of a collection of SNP probes (e.g., a collection of 10,000 to 100,000 SNP probes) and a computer program product provided herein in the manufacture of a kit for assessing cancer cells for the presence of an LOH signature. As another example, this document provides the use of a collection of primers (e.g., a collection of 10,000 to 100,000 primers for sequencing SNP regions) and a computer program product provided herein in the manufacture of a kit for assessing cancer cells for the presence of an LOH signature.

The invention will be further described in the following examples, which do not limit the scope of the invention described in the claims.

EXAMPLES

Example 1

Assessing LOH Regions and HDR

Two sets of tumors were used from advanced ovarian cancer patients. The first set of 94 tumors (training set) was used to derive a candidate signature, and the second set of 40 tumors (validation set) was used to validate the signature. All coding regions of BRCA1 and BRCA2 genes were sequenced to detect germ line and somatic mutations. Levels of BRCA1 and BRCA2 mRNA expression were measured, and Affymetrix SNP microarrays were performed.

A computer program was used to reconstruct LOH signature status based on allele intensities derived from the microarray data. An algorithm was developed and implemented as a computer program to reconstruct LOH regions based on genotype (e.g., SNP genotype) data.

One point of the algorithm was to first reconstruct allele specific copy numbers (ASCN) at each locus (e.g., SNP). ASCNs are the numbers of copies of both paternal and maternal alleles. An LOH region was then determined as a stretch of SNPs with one of the ASCNs (paternal or maternal) being zero. The algorithm was based on maximizing a likelihood function and was conceptually analogous to a previously described algorithm designed to reconstruct total copy number (rather than ASCN) at each locus (e.g., SNP). See International Application No. PCT/US2011/026098 to Abkevich et al. The likelihood function was maximized over ASCN of all loci, level of contamination with benign tissue, total copy number averaged over the whole genome, and sample specific noise level. The input data for the algorithm included (1) sample-specific normalized signal intensities for both allele of each locus and (2) assay-specific (specific for different SNP arrays and for sequence based approach) set of parameters defined based on analysis of large number of samples with known ASCN profiles.

Tumors were defined as being HDR deficient for the purpose of this analysis if they either had one or more deleterious mutations in BRCA1 and/or BRCA2 genes or if they had low expression of BRCA1 mRNA. The rest of the tumors were defined as likely HDR non-deficient for the purpose of this analysis.

Figure 5:
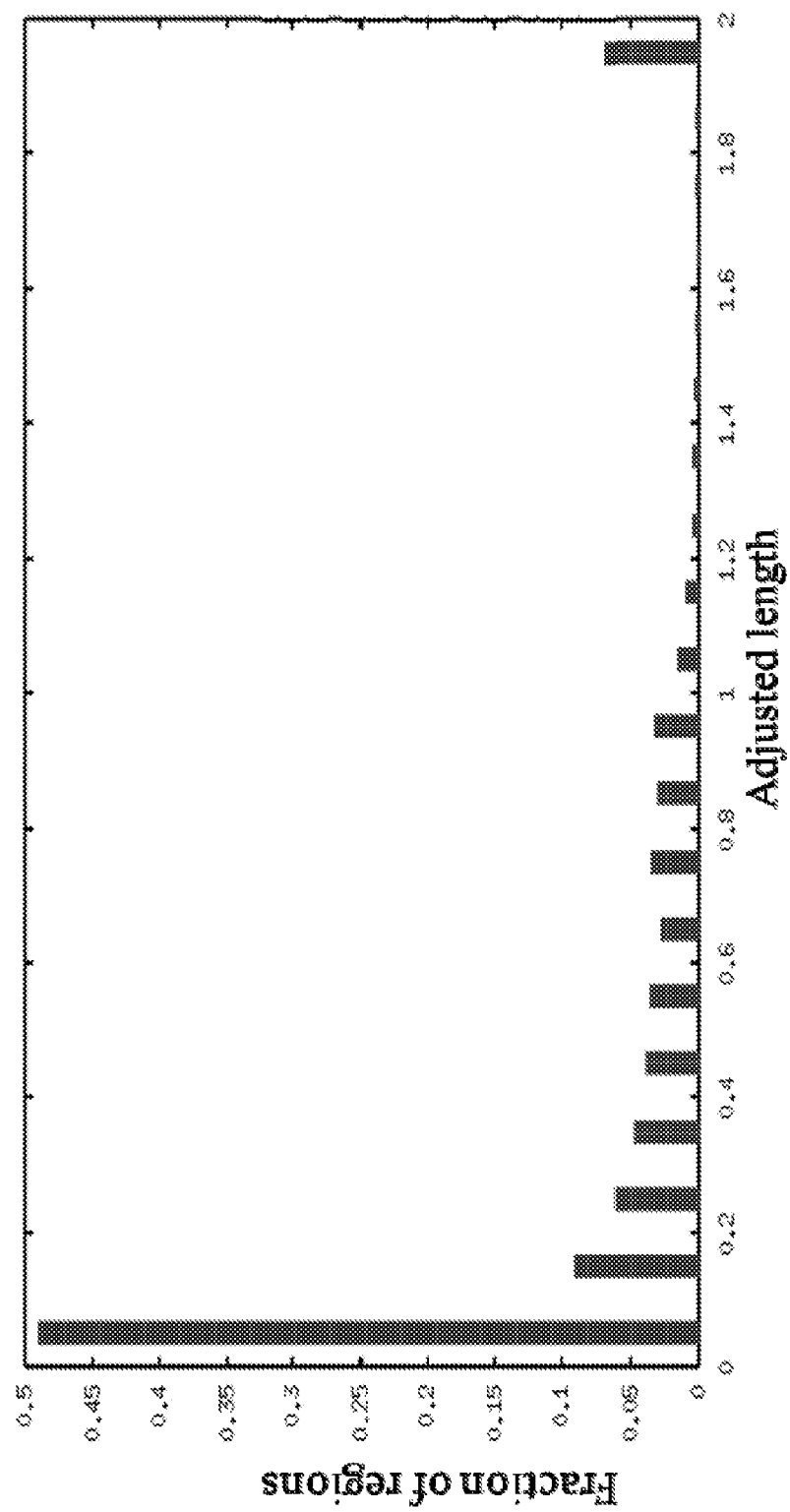
FIG. 5 is a graph plotting the length distribution of LOH regions detected in ovarian cancer cells from 62 human patients. The adjusted length refers to the fraction of chromosomes arms covered by LOH regions.
Figure 6:
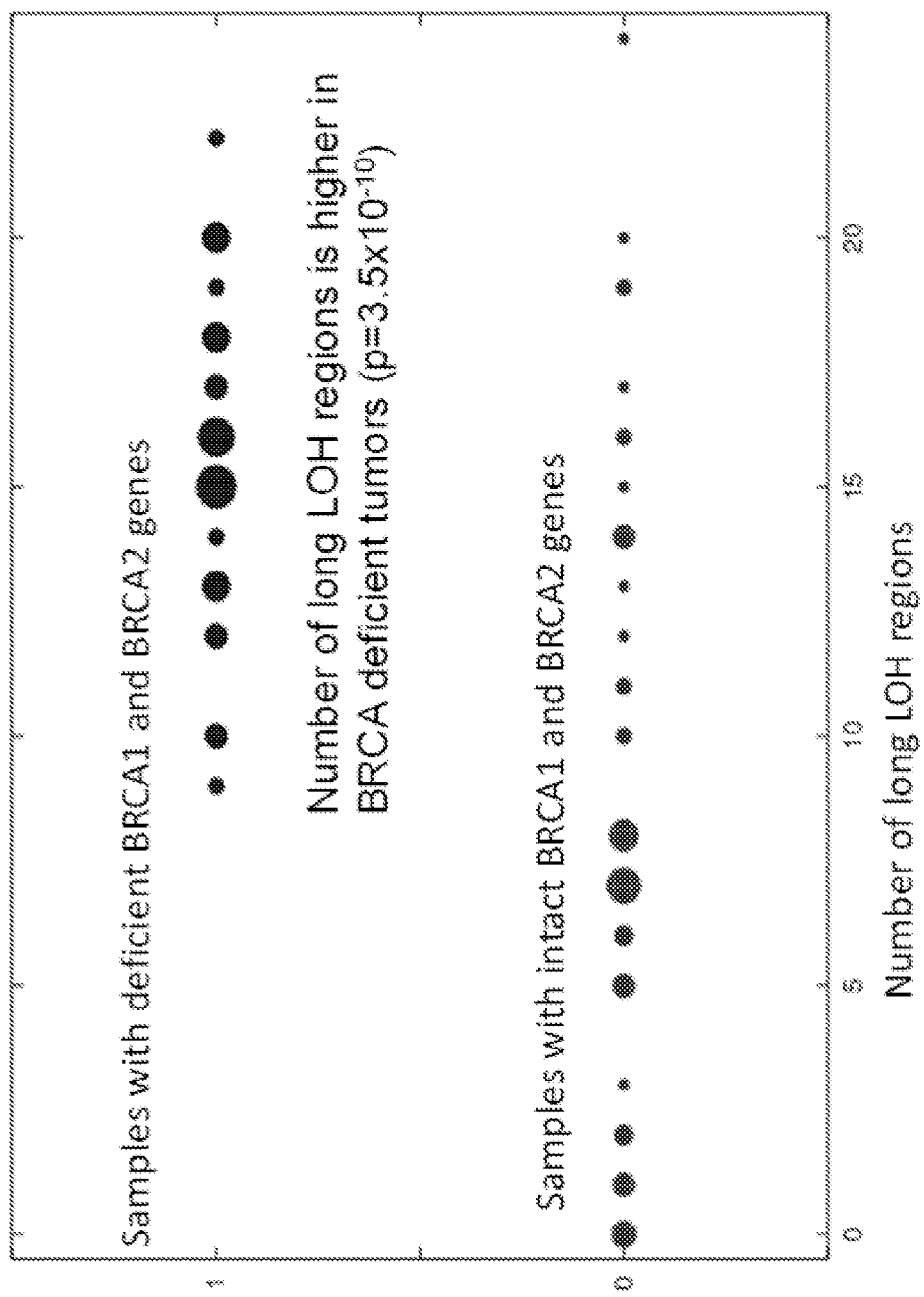
FIG. 6 is a graph plotting the number of LOH regions longer than 15 Mb and shorter than the entire chromosome for a training set of ovarian cancer cell samples with intact or deficient BRCA1 and BRCA2 genes. The size of the circles is proportional to the number of samples with such number of LOH regions.
Figure 7:
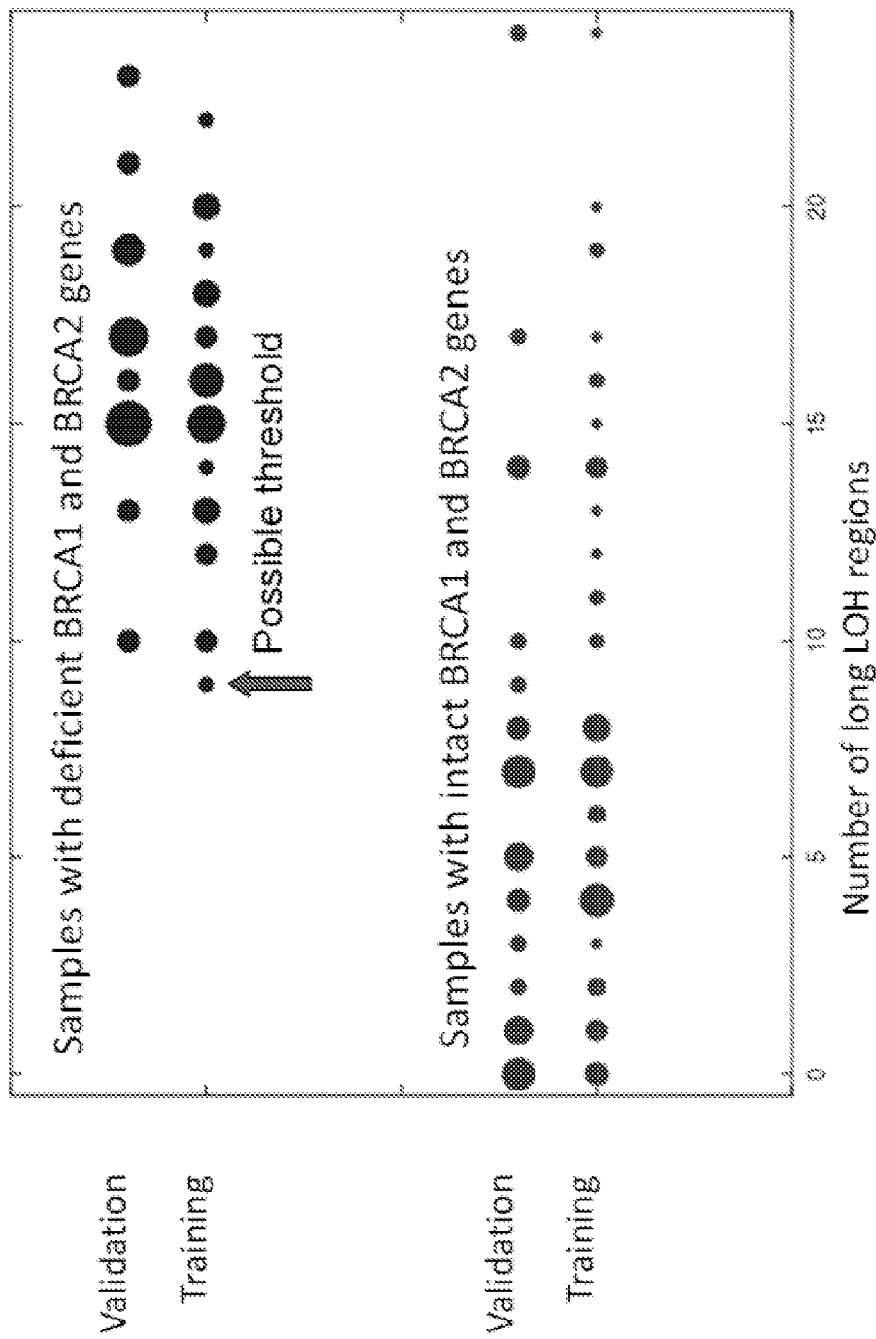
FIG. 7 is a graph plotting the number of LOH regions longer than 15 Mb and shorter than the entire chromosome for a training and validation sets of ovarian cancer cell samples with intact or deficient BRCA1 and BRCA2 genes. The size of the circles is proportional to the number of samples with such number of LOH regions.
Figure 8:
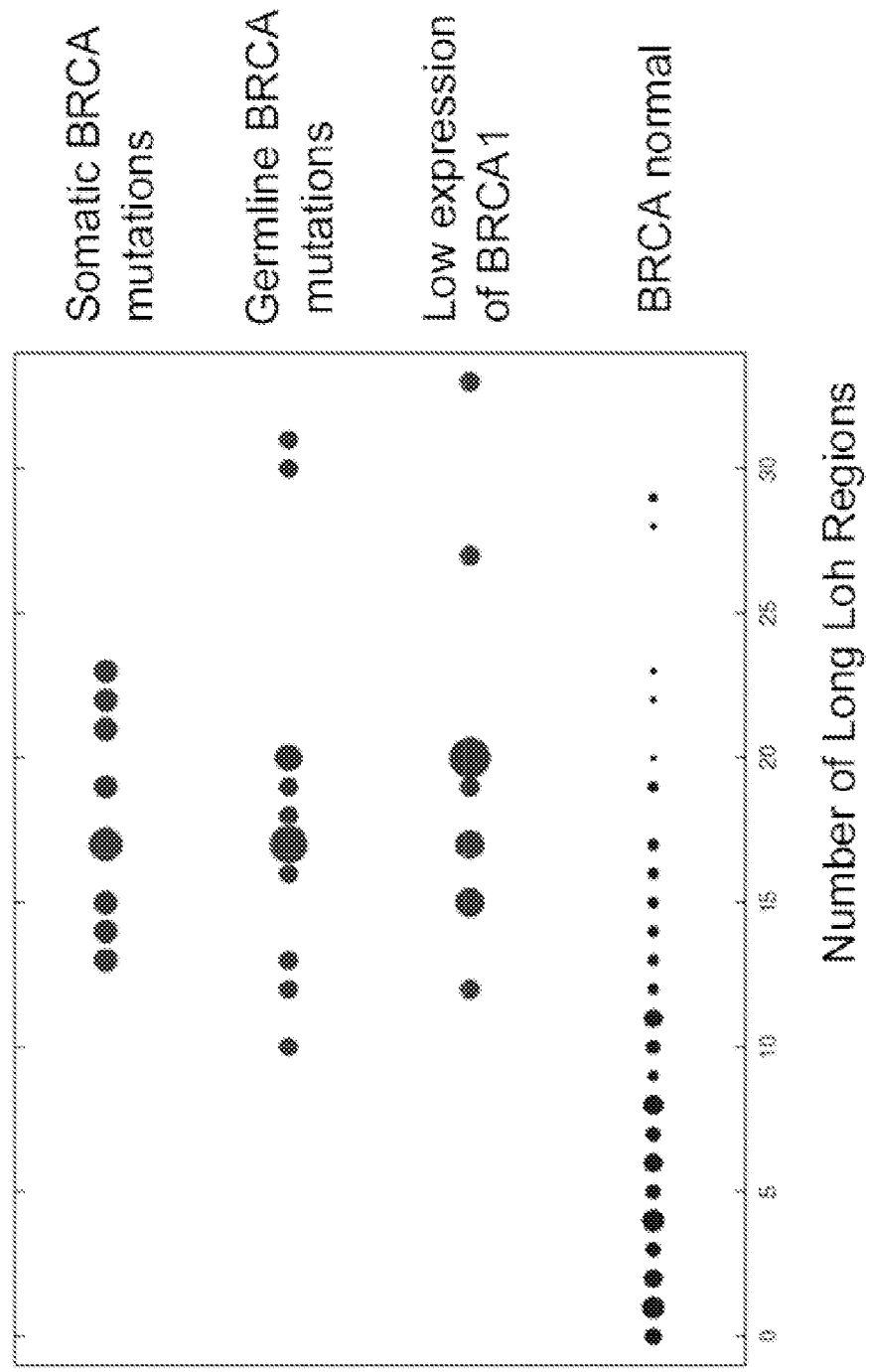
FIG. 8 is a graph plotting the number of LOH regions longer than 15 Mb and shorter than the entire chromosome for ovarian cancer cell samples with somatic BRCA mutations, with germline BRCA mutations, with low BRCA1 expression, or with intact BRCA (BRCA normal). The size of the circles is proportional to the number of samples with such number of LOH regions.

The distribution of the lengths of LOH regions was investigated (FIG. 5). Three categories of LOH regions were used: (1) LOH affecting a whole chromosome; (2) large LOH regions (greater than about 15 Mb), which typically affect a part of a chromosomal arm or the whole chromosomal arm; and (3) multiple short LOH regions (less than about 15 Mb). Second, using the training set only, the number of LOH regions of one of these three categories was assessed for possible correlations with HDR deficiency. It was discovered that (1) the number of short LOH regions did not significantly correlate with HDR deficiency (p>0.05); (2) LOH covering an entire chromosome correlated weakly with HDR deficiency (p=0.0011); and (3) the number of large LOH regions correlated significantly with HDR deficiency (p=1.9e-8). More specifically, it was discovered that all HDR deficient tumors had a high number of large LOH regions (e.g., nine or more), while the majority of tumors likely to be HDR non-deficient had a small number of large LOH regions (FIGS. 6-8). It was probable that tumors likely to be HDR non-deficient were in fact HDR deficient due to other genetic alterations, excluding BRCA1 and BRCA2 mutations and low mRNA expression. In addition to the number of large LOH regions, the total length of these regions also correlated significantly with HDR deficiency.

These results were confirmed with the validation set: (1) the number of short LOH regions did not significantly correlate with HDR deficiency (p>0.05); (2) LOH covering an entire chromosome correlated weakly with HDR deficiency (p=0.05); and (3) the number of large LOH regions correlated significantly with HDR deficiency (p=3.9e-6).

The 134 tumors were divided from combined training and validation data sets into three groups: (1) BRCA deficient if they either had one or more deleterious mutations in BRCA1 and/or BRCA2 genes or if they had low expression of BRCA1 mRNA; (2) HDR deficient/BRCA intact if they have 9 or more large LOH regions (greater than 15 Mb but less than the length of the entire chromosome); (3) HDR intact if they have less than 9 large LOH regions (greater than 15 Mb but less than the length of the entire chromosome). Results of this analysis are presented in FIG. 9. It shows a high frequency of BRCA deficiency as well as HDR deficiency that is not due to BRCA deficiency among ovarian tumors.

Figure 10:
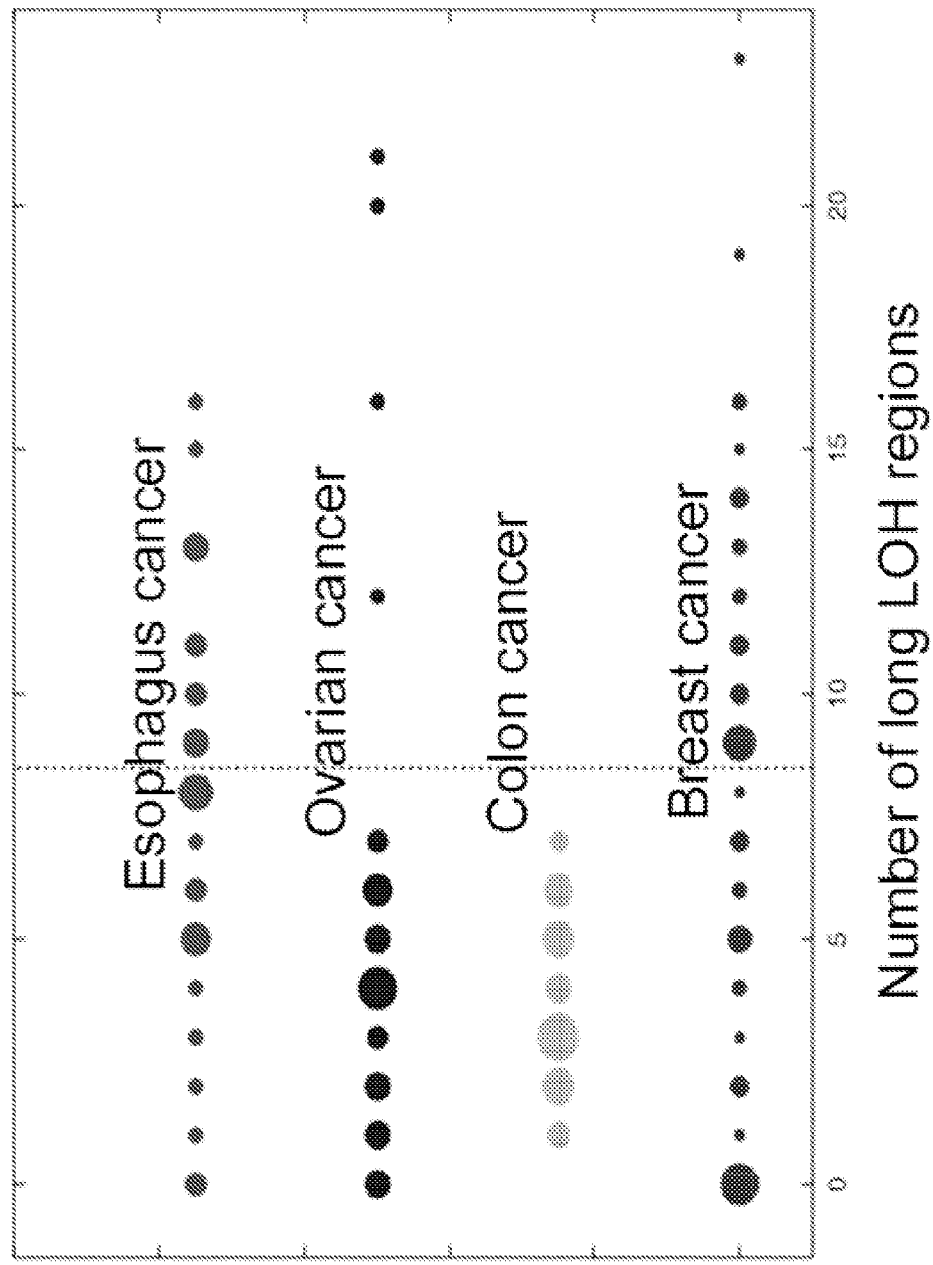
FIG. 10 is a graph plotting the number of LOH regions longer than 15 Mb and shorter than the entire chromosome for cancer cell lines for the indicated cancers. The size of the circles is proportional to the number of samples with such number of LOH regions.

FIG. 10 shows the distribution of large LOH regions (greater than 15 Mb but less than the length of the entire chromosome) for different types of cancer cell lines. The size of the circles is proportional to the number of samples with such number of large LOH regions. Frequency of HDR deficiency (cell lines with at least 9 of such large LOH regions) is the highest among breast and esophagus cancer cell lines. No HDR deficiency was observed among colon cancer cell lines. Validating the previous findings for ovarian tumors, all BRCA deficient cell lines were found to be HDR deficient as well.

Figure 11:
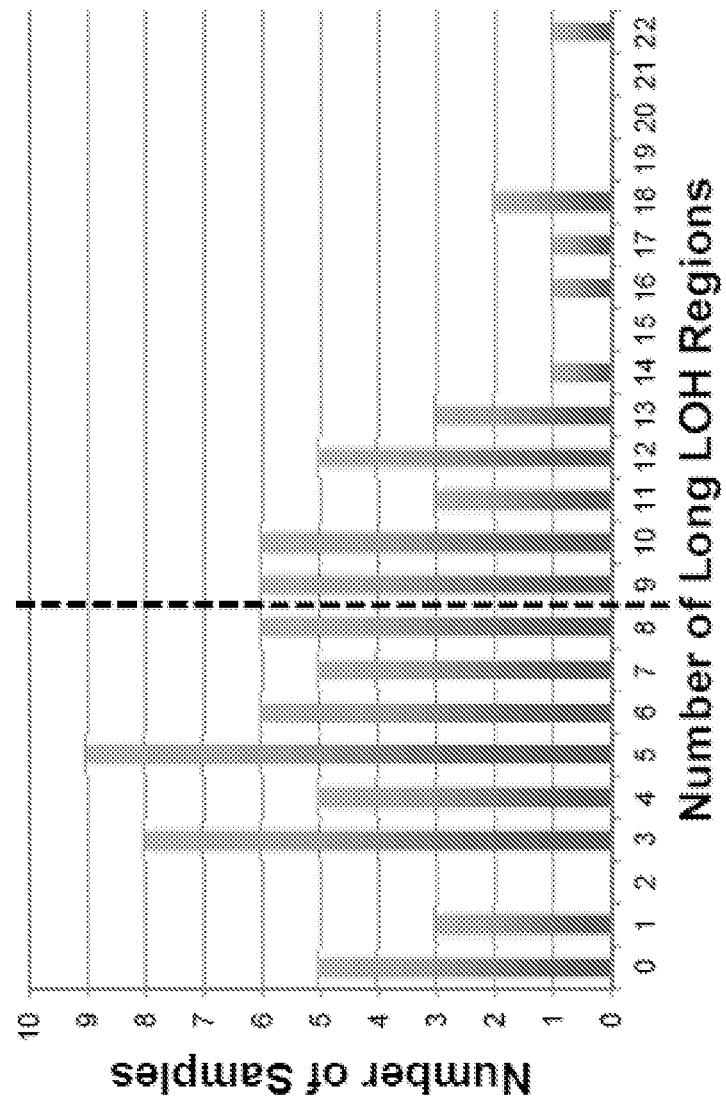
FIG. 11 is a graph plotting the number of LOH regions longer than 15 Mb and shorter than the entire chromosome for lung cancer samples.

FIG. 11 shows the distribution of large LOH regions (greater than 15 Mb but less than the length of the entire chromosome) for publicly available lung tumor data set (GSE19399 from Gene Expression Omnibus). It was observed that frequency of HDR deficiency (defined as having at least 9 large LOH regions) is quite large among lung tumors (39%).

Figure 12:
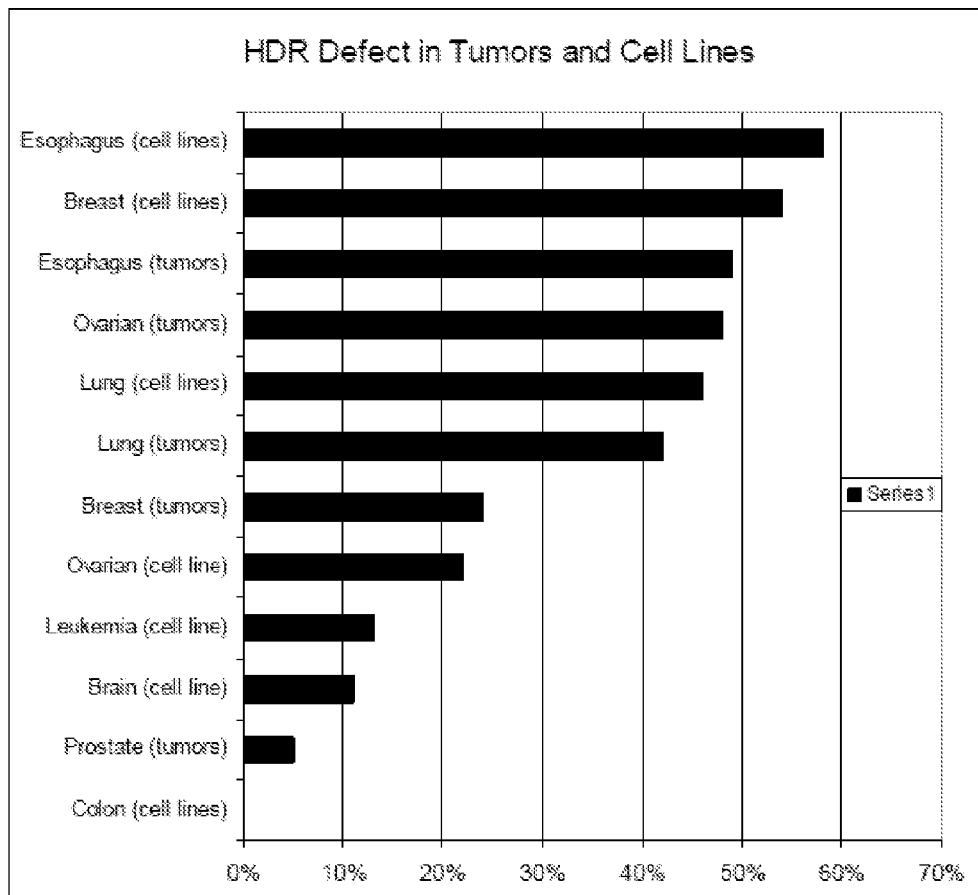
FIG. 12 is a graph plotting the percentage of the indicated cancers or cancer cell lines having an HDR deficiency.

In FIG. 12 the results of analysis of different tumors and cell lines are summarized. Frequency of HDR deficiency defined as fraction of samples with at least 9 large LOH regions (greater than 15 Mb but less than the length of the entire chromosome) is presented for several tumors and cell lines. This frequency is as high as 50% among ovarian tumors and was not observed at all among brain and colon cell lines. Thus it appears that HDR deficiency plays an important role for the majority of cancers.

Example 2

Chemo Toxicity Responses

In preparation of chemo toxicity response experiments, all cell lines were grown at 37° C. plus 5% $CO_2$ in 75 $cm^2$ tissue culture flasks (VWR International, Inc. Cat #353136) and the recommended growth medium. Before performing each experiment, each cell line was trypsinized (Invitrogen Corporation Cat #25200-056), counted, and seeded in Advanced RPMI 1640 (Invitrogen Corporation Cat #12633-020), 3% FBS, 1% penicillin/streptomycin (Invitrogen Corporation Cat #15140-122) at 2500 cells or 5000 cells in 100 μL media per well from columns 2-12 of 96-well polystyrene microplates with clear bottom (Perkin Elmer Cat #6005181), leaving column 1 with 100 μL per well of media only. The cell-seeded plates were then incubated at 37° C. plus 5% $CO_2$ overnight.

Two different final drug concentration working stocks were prepared. In cases where 100% DMSO was required for drug solubility, Advanced RPMI 1640 was used as the diluent for the highest concentration. Advanced RPMI 1640 plus a predetermined amount of DMSO equal to the total DMSO in the high concentration working stock was used for the low concentration, with a maximum of 60% DMSO used for the lowest concentration. This was done to keep the DMSO concentrations equal in every well and prevent non-specific cell death as a result of DMSO. The lower of the two drug concentrations was placed in a 96-well, thin-wall PCR cycle plate (Robbins Scientific Cat #1055-00-0) in rows A-D, column 12, while the higher concentration was placed in rows E-H, column 12, of the same plate. Serial dilutions of 1:2 or 1:3 were performed in a descending manner from column 12 to 3, leaving columns 1 and 2 to be used for no cell/no drug and no drug controls. This allowed for quadruplet data points for each drug concentration. Once dilutions were complete, 5 μL was transferred from the dilution plate to the corresponding well of the seeded cell plate. Plates receiving drugs were then incubated at 37° C. plus 5% $CO_2$ for either 3 days or 6 days.

Following a 3-day or 6-day dose regimen, ATPlite assays (Perkin Elmer cat #6016941) were run on each well of each plate according to the ATPLite Assay protocol. The luminescence was then read on a FUSION machine and saved as a .CSV file. For each cell-line and drug combination, the four replicates of the no-drug control were averaged and divided by 100 to create a "normalization factor" used to calculate a normalized percent survival. The normalized percent survival for the no-drug controls was 100%. The four replicates of the cell-plus-drug wells were averaged and divided by the normalization factor for each drug concentration. The percent survival for each drug concentration, starting with a concentration equal to 0, was used to calculate an $IC_{50}$ using proprietary software.

Figure 13:
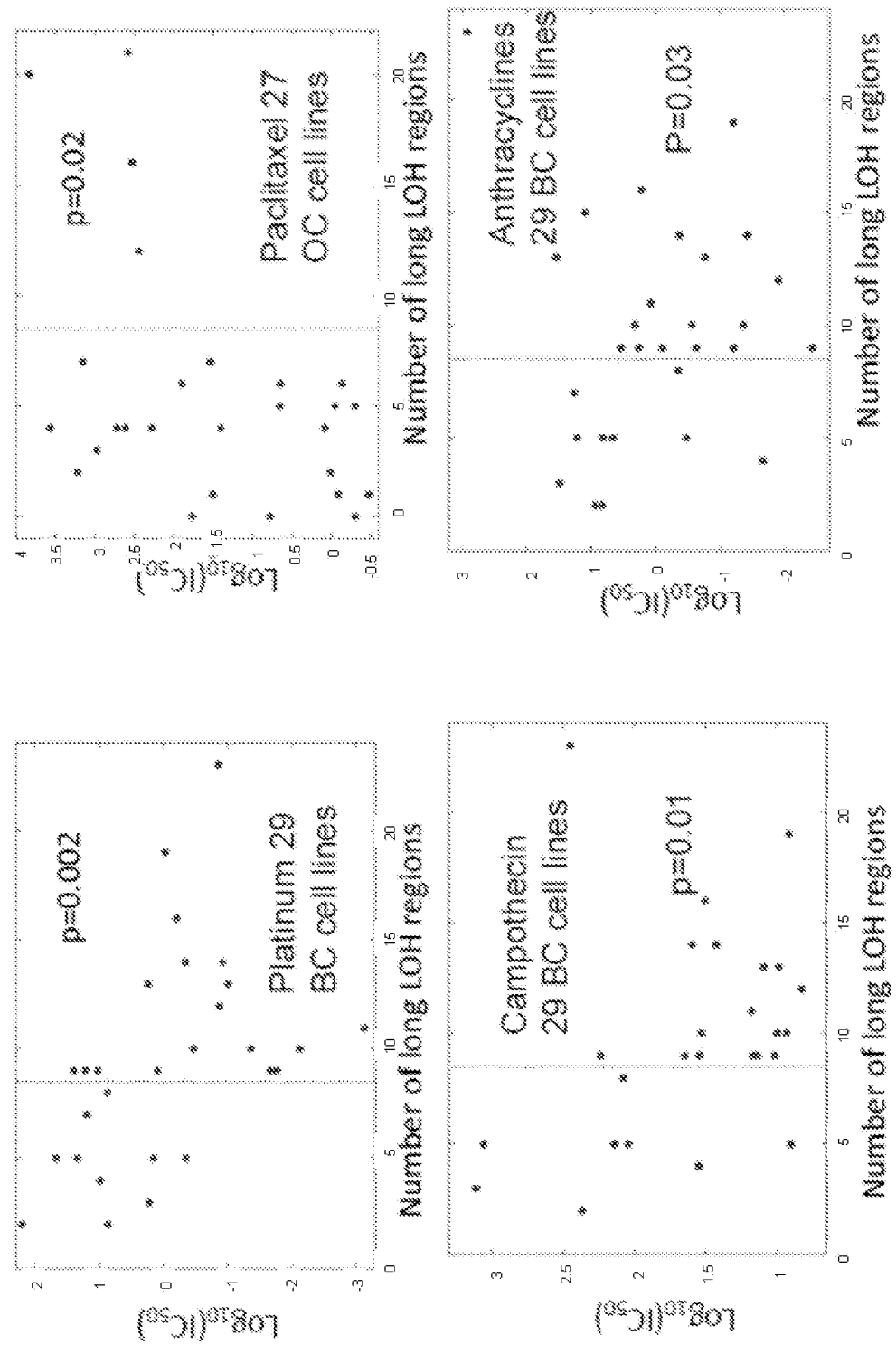
FIG. 13 contains graphs plotting the $IC_{50}$ values ($Log_{10}(IC_{50})$) of camptothecin, as well as averaged $Log_{10}(IC_{50})$ values for platinum compounds (oxaliplatin, cisplatin, and carboplatin), or anthracyclines (doxorubicin and epirubicin) when exposed to 29 breast cancer cell lines having the indicated number of LOH regions longer than 15 Mb and shorter than the entire chromosome or the $IC_{50}$ values ($Log_{10}(IC_{50})$) of paclitaxel when exposed to 27 ovarian cancer cell lines having the indicated number of LOH regions longer than 15 Mb and shorter than the entire chromosome. The dashed lines place a threshold number at nine.

FIG. 13 shows response to chemotherapy for breast and ovarian cancer cell lines. On y-axis are indicated values of $Log_{10}(IC_{50})$ for different chemotherapy drugs (camptothecin, as well as averaged results for platinum compounds (oxaliplatin, cisplatin, and carboplatin) or anthracyclines (doxorubicin and epirubicin)) when exposed to 29 breast cancer cell lines as well as $Log_{10}(IC_{50})$ of paclitaxel when exposed to 27 ovarian cancer cell lines. On the x-axis the number of large LOH regions longer than 15 Mb and shorter than the entire chromosome are indicated for these cell lines. The dashed lines place a threshold number at nine.

Figure 14:
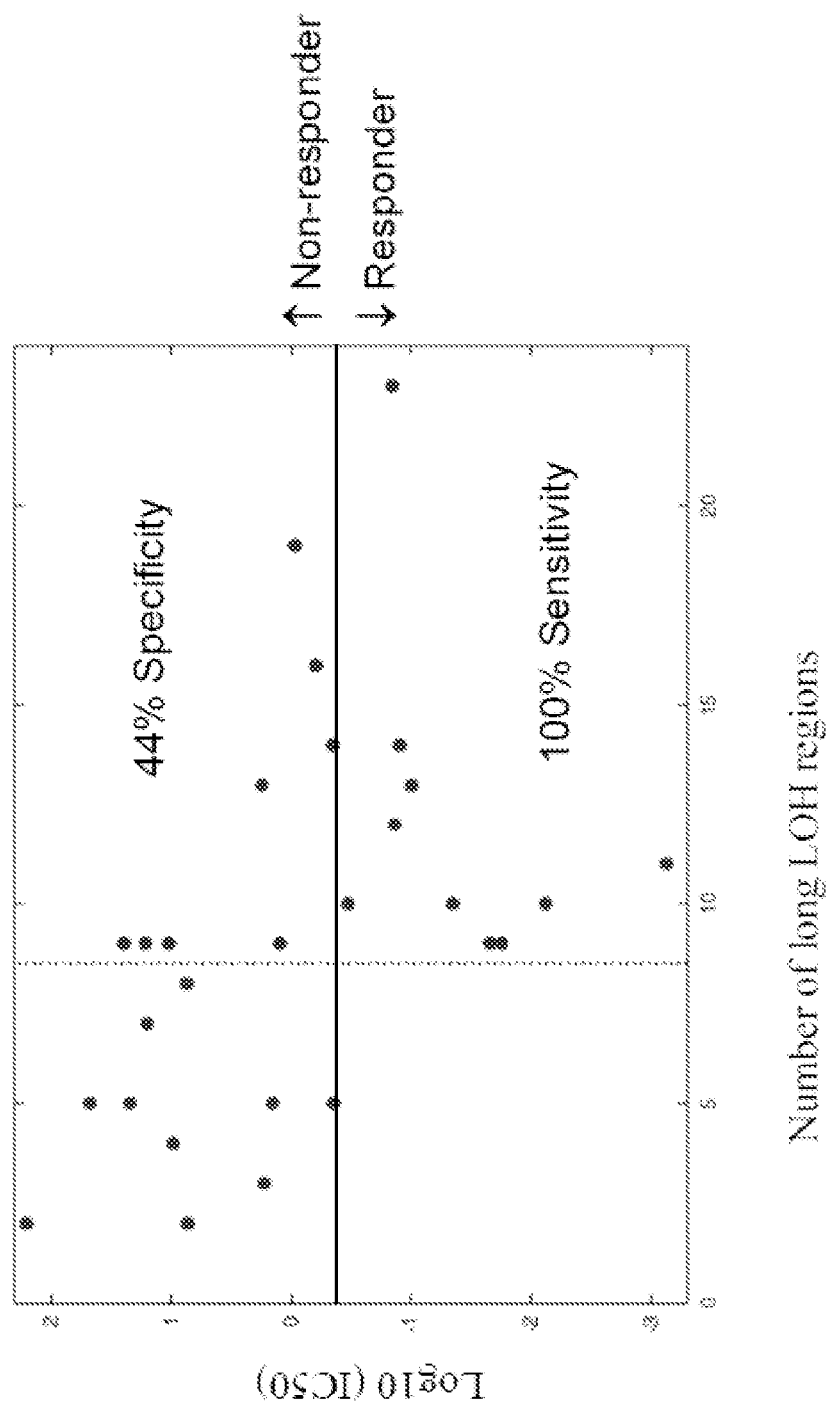
FIG. 14 is a labeled version of a graph from FIG. 13 that plots the averaged $Log_{10}(IC_{50})$ values of platinum compounds (oxaliplatin, cisplatin, and carboplatin) when exposed to 29 breast cancer cell lines having the indicated number of LOH regions longer than 15 Mb and shorter than the entire chromosome.

FIG. 14 is a version of a graph from FIG. 13 that indicates specificity and sensitivity among responders and non-responders to treatment with platinum compounds (oxaliplatin, cisplatin, and carboplatin) when exposed to 29 breast cancer cell lines. The dashed lines place a threshold number of large LOH regions longer than 15 Mb and shorter than the entire chromosome at nine. The solid line divides cell lines into responders and non-responders.

Example 3

Further Validation of HR Deficiency Assay

Materials and Methods
Ovarian Tumor Samples

Three independent human ovarian cancer cohorts were used. 1: 152 unselected ovarian cancer samples. 2: 53 high grade serous ovarian tumors. 3: Publicly available data from 435 serous ovarian cancer samples for which complete information was available were downloaded from The Cancer Genome Atlas (TCGA) Network web site on Oct. 31, 2011. All cohorts were obtained under Institutional Review Board (IRB)-approved protocols. Patient and tumor characteristics are shown in Table 2. Varying numbers of samples were utilized in the assays described (Table 3).

TABLE 2

Patient and cancer characteristics.

| | First cohort | Second cohort | Third cohort |
|---|---|---|---|
| Total Number of Patients | 152 | 53 | 435 |
| Age at diagnosis | | | |
| Range | 37-88 | 38-77 | 30-89 |
| Median | 59 | 56 | 59 |
| Unknown | 4 (2.6%) | 0 | 0 |

TABLE 2-continued

Patient and cancer characteristics.

| | First cohort | Second cohort | Third cohort |
|---|---|---|---|
| Follow-up time | | | |
| Range | 20-5570 | 213-3294 | 8-5480 |
| Median | 1127 | 701 | 874 |
| Unknown | 5 (3.2%) | 0 | 2 (0.46%) |
| Stage | | | |
| 1 | 9 (5.9%) | 0 | 6 (1.38%) |
| 2 | 14 (9.2%) | 0 | 21 (4.83%) |
| 3 | 107 (70.4%) | 46 (86.8%) | 338 (77.70%) |
| 4 | 21 (13.8%) | 7 (13.2%) | 69 (15.86%) |
| Unknown | 1 (0.7%) | 0 | 1 (0.23%) |
| Histology | | | |
| Serous | 133 (87.5%) | 40 (75.5%) | 435 (100.00%) |
| Non-serous | 8 (5.3%) | 4 (7.6%) | 0 |
| Mixed | 10 (6.6%) | 1 (1.9%) | 0 |
| Unknown | 1 (0.7%) | 8 (15.1%) | 0 |
| Grade | | | |
| 1 | 8 (5.3%) | 1 (1.9%) | 2 (0.46%) |
| 2 | 18 (11.8%) | 12 (22.6%) | 50 (11.49%) |
| 3 | 126 (82.9%) | 40 (75.5%) | 373 (85.75%) |
| 4 | 0 | 0 | 1 (0.23%) |
| Unknown | 0 | 0 | 8 (1.84%) |
| Residual disease after surgery | | | |
| 0 | 9 (5.9%) | 0 | 84 (19.31%) |
| <=1 cm | 95 (62.5%) | 44 (83%) | 200 (45.98%) |
| >1 cm | 40 (26.3%) | 9 (17%) | 102 (23.45%) |
| Unknown | 8 (5.3%) | 0 | 49 (11.26%) |
| Surgery | | | |
| Yes | 152 (100%) | 53 (100%) | 386 (88.74%) |
| No | 0 | 0 | 0 |
| Unknown | 0 | 0 | 49 (11.26%) |
| Chemotherapy | | | |
| Yes | 139 (91.5%) | 52 (98.1%) | 399 (91.72%) |
| Platinum (cis or carboplatin)-based (no taxane) | 12 (7.9%) | 1 (1.9%) | NA |
| Platinum plus Taxane (paclitaxel or docetaxel)-based | 128 (83.6%) | 51 (96.2%) | NA |
| No | 7 (4.6%) | 0 | 23 (5.29%) |
| Unknown | 6 (4%) | 1 (1.9%) | 13 (2.99%) |

TABLE 3

Number of samples used in each assay.

| Assay | Cohort 1 Number of samples | Cohort 1 Reason assay was not applied to all samples | Cohort 2 Number of samples | Cohort 2 Reason assay was not applied to all samples |
|---|---|---|---|---|
| Affymetrix 500K SNP arrays | 152 | not applicable | 53 | not applicable |
| BRCA1 and BRCA2 tumor sequencing | 150 | sequencing failed | 52 | sequencing failed |
| BRCA1 and BRCA2 germline sequencing | 19 | normal tissue not available or no mutation detected in tumor | 11 | normal tissue not available or no mutation detected in tumor |
| CCP and BRCA1 qPCR | 137 | insufficient tissue for RNA extraction | 53 | not applicable |
| BRCA1 and BRCA2 methylation analysis | 126 | insufficient DNA for analysis | 34 | insufficient DNA for analysis |
| Other HR gene methylation analysis | 92 | insufficient DNA for analysis | 0 | insufficient DNA for analysis |

Cell Lines 67 cancer cell lines were analyzed (29 ovarian, 34 breast, 3 colon, 1 pancreatic). Three breast cancer cell lines were obtained from DSMZ (Braunschweig, Germany). The colon, pancreatic, and remaining breast cancer cell lines were obtained from ATCC (Manassas, Va.). Cancer cell lines were grown in RPMI+10% FBS+1% penicillin/streptomycin media at 37° C. in T75 flasks until ~5×10$^6$ cell density. Exceptions were cell lines that required non-standard media, L-glutamine, or insulin. Cells grown in suspension were centrifuged for 5 minutes at 1700 rpm in a 1.5 mL centrifuge tube and the supernatant discarded. Cells grown in a monolayer had medium removed by aspiration, were washed with PBS, and trypsin solution added. After the cells detached they were collected in medium, transferred to a 1.5 mL microcentrifuge tube and centrifuged at 1700 rpm for 5 minutes. The supernatant was discarded. Isolated cells were resuspended in 200 µL PBS Extraction of Genomic DNA and Total RNA from Frozen Tumors and Cell Lines 10 µm frozen sections were cut and macrodissected. The tissue was homogenized (TissueRuptor (Qiagen)) after addition of QIAzol lysis reagent, following by RNA isolation using a Qiagen miRNAeasy Mini Kit per the manufacturers protocol. A QIAamp DNA Mini Kit (Qiagen) was used to isolate DNA as per the manufacturer's protocol with an overnight lysis incubation at 56° C. and RNase A treatment.

BRCA1 and BRCA2 Sequencing

BRCA1 and BRCA2 sequencing was performed as described in Hennessy et al., 2010. Mutations identified were only included in the analyses if classified as deleterious or suspected deleterious based on previously described criteria (Beaudet and Tsui, 1993).

Promoter Methylation qPCR Assays

The Methyl-Profiler DNA Methylation PCR Array System (SABiosciences) was used to quantify methylation levels following the manufacturers recommended protocol. DNA methylation-sensitive and methylation-dependent restriction enzymes were used to selectively digest unmethylated or methylated genomic DNA, respectively. Post-digest DNA was quantified by real-time PCR using primers flanking the regions of interest. The relative concentrations of differentially methylated DNA are determined by comparing the amount of each digest with that of a mock digest.

BRCA1 Promoter Methylation Sequencing Assay 50-300 ng of DNA was incubated for ~5 hours at 60° C. with brief elevations to 95° C. under acidic conditions in the presence of bisulfite. After incubation, the reaction was bound to a spin column and washed under basic conditions to remove bisulfite, converted DNA was then eluted in 15 µL. Lower case region of primers is specific to the genomic region being amplified. Upper case region of primers corresponds to the 454 Titanium chemistry tails and a 4 bp barcode (last 4 bases before the region specific bases). By combining the forward and reverse primers in multiple combinations, it is possible to multiplex up to 100 samples in a single sequence reaction.

BRCA1 and Cell Cycle Progression Signature Expression Assays

RNA was treated with Amplification Grade Deoxyribonuclease I (Sigma-Aldrich Inc.) per manufacturer's protocol with an extended incubation time of 30 minutes. Reverse transcription was performed using a High-Capacity cDNA Reverse Transcription Kit (Applied Biosystems, Foster City, Calif.) per manufacturer's instructions.

Replicate preamplifications were run independently using the Taqman PreAmp Master Mix Kit (Applied Biosystems) protocol in a 5 µl reaction volume. To preamplification replicates were run at 8 and 18 cycles respectively for cell cycle gene assays. Three preamplification replicates were run at 18 cycles only for BRCA1 assays. The post-amplification products were diluted 1:5 in low-EDTA Tris-EDTA (TE). Quantitative Polymerase Chain Reaction (qPCR) was then performed and assessed on Gene Expression M48 Dynamic Arrays (Fluidigm, South San Francisco, Calif.) per manufacturer's protocol. The comparative cycle threshold ($C_T$) method was used to calculate relative gene expression. $C_T$s from preamplification of different numbers of cycles were centered by the average of the genes on the replicate that were in common between all replicates. The resulting values were normalized first by the average $C_T$s of the housekeeper genes then by the average of the normalized $C_T$s of each assay on all samples from the first cohort to yield $\Delta\Delta C_T$. CCP score and relative BRCA1 expression were calculated as the average of the negative of the $\Delta\Delta C_T$s of the cell-cycle genes and BRCA1 assays, respectively.

Identification of Samples with Loss of BRCA1 Expression:

Samples in which CCP expression and BRCA1 expression are anti-correlated were defined as BRCA1 deficient. The threshold for identifying patients with abnormal BRCA1 expression was defined using robust linear regression in a large set of ovarian cancer samples (n=300). BRCA1 expression was regressed on CCP score using iteratively re-weighted least squares (IWLS). Points outside of the 99% prediction interval on the low end were considered abnormal. This method is described in greater detail in International Application No. PCT/US2011/054369 to Timms et al.

Affymetrix 500K GeneChip Arrays

The Affymetrix GeneChip Mapping NspI or StyI Assay Kit was used in the generation of biotinylated DNA for Affymetrix Mapping 500K NspI or StyI microarray hybridizations (each assay was prepared separately). Genomic DNA (250 ng) was digested with NspI or StyI restriction enzyme and adaptors were added to restriction fragment ends with T4 DNA ligase. Adaptor-modified samples were PCR amplified using Clontech Titanium Taq, which generated an amplified product of average size between 200 and 1,100 bp. Amplification products were purified using a Clontech DNA amplification cleanup kit. 90 µg of purified DNA was fragmented using Affymetrix Fragmentation Reagent. Biotin-labeling of the fragmented sample was accomplished using the GeneChip DNA Labeling Reagent. Biotin-labeled DNA was hybridized on NspI or StyI Affymetrix microarrays at 49° C. for 16 to 18 hours in the Affymetrix rotation oven. After hybridization, probe array wash and stain procedures were carried out on the automatic Affymetrix Fluidics Stations as per manufacturer's manual and microarrays were scanned and raw data was collected by Affymetrix GeneChip Scanner 3000.

CN and LOH Analysis of SNP Microarray Data

The algorithm is designed to determine the most likely allele specific copy number at each SNP location. The corresponding likelihood explicitly takes into account contamination of a cancer DNA sample with non-cancer stromal cell DNA. A similar algorithm for CN analysis is described in detail in International Application No. PCT/US2011/026098 to Abkevich et al. (publication no. WO/2011/106541). The algorithm used in this paper was implemented in two versions, one for analysis of Affymetrix 500K GeneChip array data generated internally, and the other for analysis of GenomeWideSNP6 Affymetrix array data downloaded from the TCGA web site (http://tcga-data.nci.nih.gov/tcga/dataAccessMatrix.htm?diseaseType=OV). The latter array, in addition to SNP probes, contains a number of probes for non-polymorphic locations across the human genome. These probes are informative for CN analysis but are not directly informative for LOH analysis.

Statistical Analysis p-values in this paper were calculated using Kolmogorov-Smirnov test unless otherwise specified.

Results

HR Deficient Tumors

A tumor sample was considered HR deficient if it had a germline or somatic mutation in BRCA1 or BRCA2, or methylation or low mRNA expression of BRCA1. 31 of 152 samples from the first cohort were carriers of mutations in BRCA1 and/or BRCA2, along with 14/53 from the second cohort and 83/435 from the third cohort (two of which were excluded from the further analysis, see below). Mutations are summarized in Table 4.

TABLE 4

BRCA1, BRCA2, and RAD51C defects detected in the study cohorts.

| Cohort | N | BRCA1 + BRCA2 mutation | BRCA1 mutation | BRCA2 mutation | Total | N | RAD51C methylation | RAD51C methylation + BRCA1 mutation |
|---|---|---|---|---|---|---|---|---|
| 1 | 152 | 1 | 23 | 8 | 32 | 89 | 2 | 1 |
| 2 | 53 | 0 | 11 | 3 | 14 | ND | ND | ND |
| 3 | 435 | 0 | 51 | 34[1] | 85[1] | 435 | 11 | 0 |

[1]Two of these mutations were excluded from the analysis because one copy of BRCA2 remained intact.

The degree of methylation was measured for promoter CpG islands of both BRCA1 and BRCA2. Methylation in multiple samples was observed for BRCA1, but not BRCA2. 11 of 126 samples from the first cohort, 3 of 34 from the second cohort and 64 of 435 from the third cohort were defined as HR deficient due to high levels of BRCA1 promoter methylation. Deleterious BRCA1 or BRCA2 mutations were not observed in any of these samples, except for one sample from the third cohort.

Low mRNA expression of BRCA1 or BRCA2 might also lead to HR deficiency, and be the result of mechanisms other than promoter methylation. BRCA1 and BRCA2 expression levels were measured for 137 samples from the first cohort and 53 samples from the second cohort. Expression of BRCA1 in 20 samples was abnormally low. Only five samples with abnormally low expression of BRCA1 were not flagged as HR deficient due to BRCA1 promoter methylation. No abnormally low expression was observed for BRCA2.

A single intact copy of BRCA1 or BRCA2 is required for functionality. For all BRCA1 deficient samples, the BRCA1 gene is contained within a region of LOH. In addition, for all but two BRCA2 deficient samples, the BRCA2 gene is observed within an LOH region. These two BRCA2 deficient samples were not considered HR deficient in our analysis.

Distribution of Lengths of LOH Regions

Figure 16:
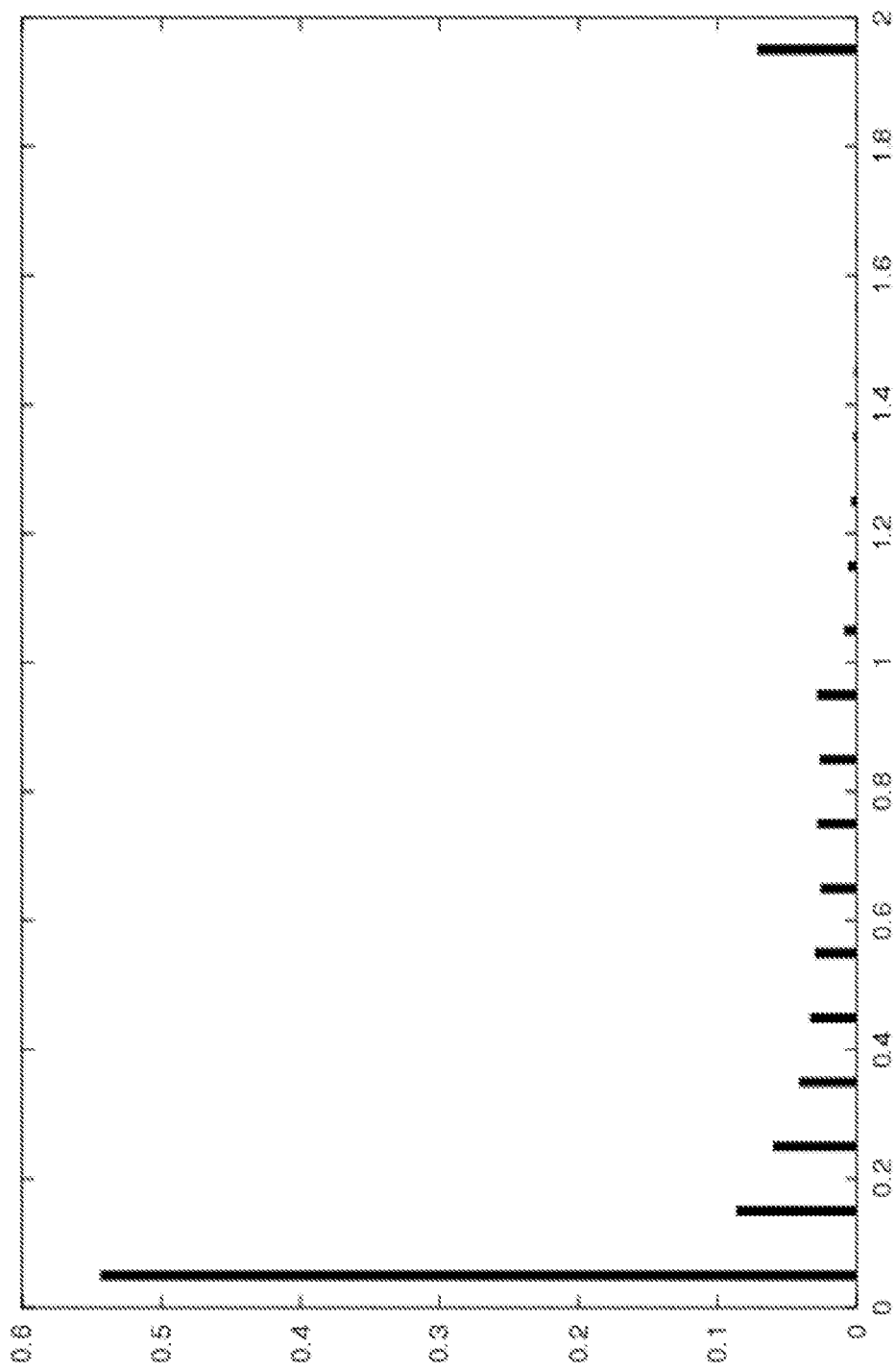
FIG. 16 shows fraction of lengths of LOH regions vs. length of these regions adjusted on the length of chromosome arm. The largest adjusted value on this figure is equal to two corresponding to LOH over the entire chromosome.

The initial hypothesis was that regions with LOH of different length might appear in the cancer genome through different pathways, thus association between LOH and HR deficiency might depend on the length of LOH regions. The distribution of lengths of LOH regions adjusted on the length of chromosome arm on which these LOH regions have been observed is shown in FIG. 16. Chromosomes 13, 14, 15, and 22 were excluded because SNPs are not available for the p arms of these chromosomes. Three distinct features were observed in this distribution. First, there are many short LOH regions. Second, there is a long flat tail of LOH regions up to the length of a single chromosome arm. Few LOH regions cover more than one chromosome arm but less than the whole chromosome. Finally, there is a high peak corresponding to LOH over the whole chromosome. The observed distribution is quite different from the similar distribution obtained for CN variations (Beroukhim et al. 2010), this suggests that CN variations and LOH regions might arise via different mechanisms.

Correlation Between Samples with HR Deficiency and LOH

Figure 17A:
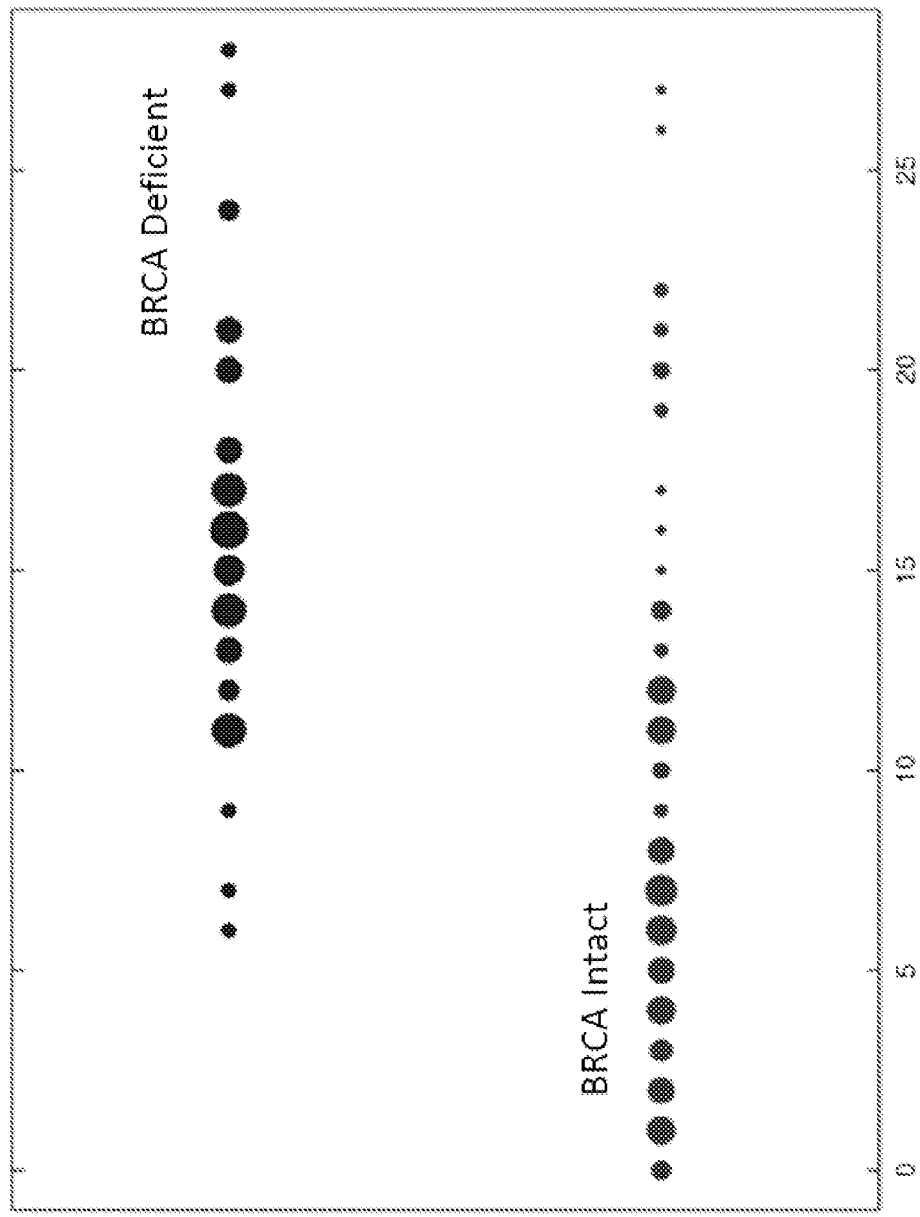
FIG. 17a shows the HRD score in tumor samples for the first cohort (46 of 152 samples were BRCA1 or BRCA2 deficient). Top circles: BRCA1 or BRCA2 deficient samples. Bottom circles: BRCA1 and BRCA2 intact samples. The area of each individual circle is proportional to the number of samples with the corresponding number of LOH regions.
Figure 19:
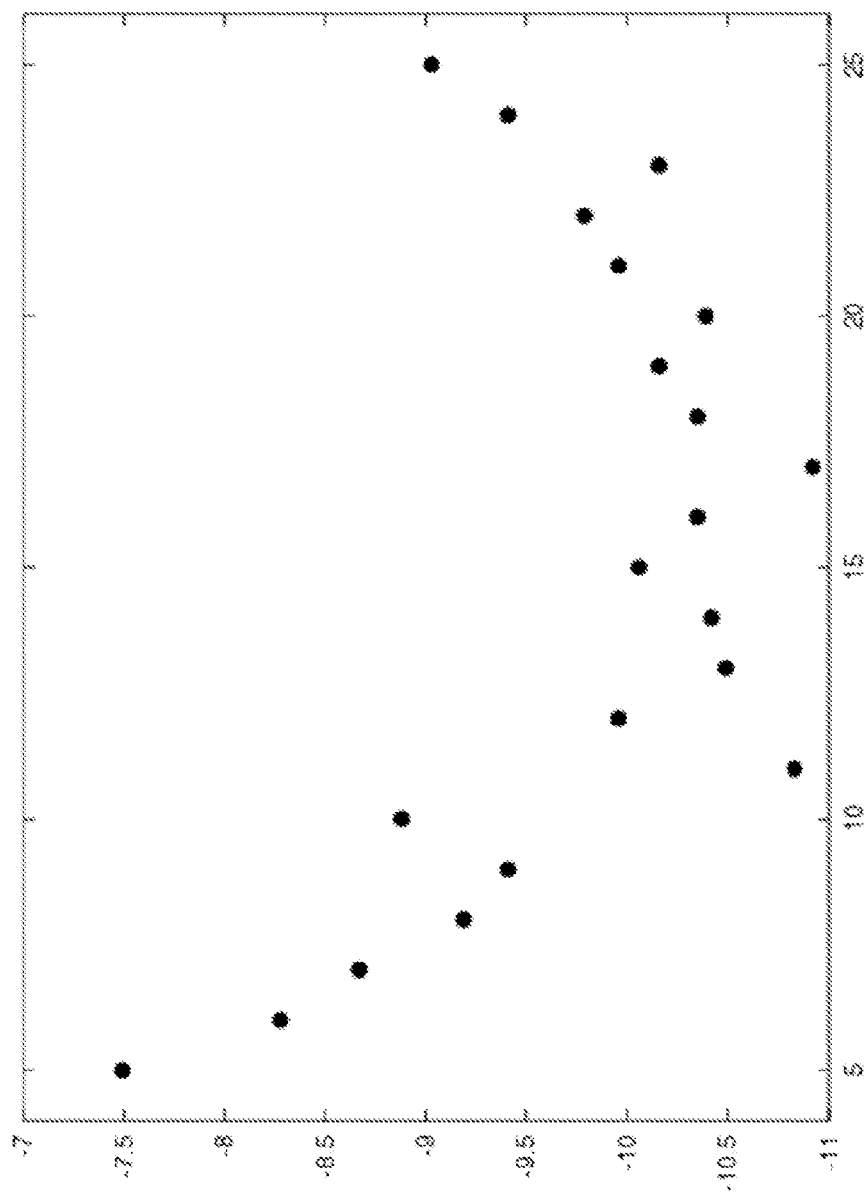
FIG. 19 shows the correlation between LOH scores and HR deficiency calculated for different LOH region length cut-offs for the first cohort. Corresponding log 10(p-value) are on the y-axis. The relationship between the cut-off of the size of LOH regions and the significance of correlation of the LOH score with HR deficiency was investigated. This figure shows that LOH length cut-offs may readily range from 11 to 21 Mb. The cut-off of 15 Mb, approximately in the middle of the interval, may be used in some preferred embodiments since it was found to be more sensitive to statistical noise present in the data.

The first cohort of samples was used as the "discovery" cohort. LOH regions on chromosome 17 were excluded from the analysis because in almost all samples LOH was observed over this chromosome, probably because genes important for progression of ovarian cancer are on this chromosome. We checked for correlation between HR deficiency and the number of short LOH regions (<15 Mb), the number of long LOH regions (>15 Mb but less than the whole chromosome), and the number of LOH regions covering whole chromosomes. Various different LOH region length cut-offs can be used and the influence of this cut-off on detecting HR deficiency is explored in FIG. 19 and its accompanying discussion, though 15 Mb was found to be generally preferred. There was no significant correlation between the number of short LOH regions and HR deficiency. The number of LOH regions covering the whole chromosome was significantly larger in tumors with intact BRCA1 or BRCA2 ($p=4 \times 10^{-5}$). The number of long LOH regions (termed hereafter in this Example 3 and throughout this document as "HRD score") was significantly higher in tumors with deficient BRCA1 or BRCA2 ($p=9 \times 10^{-11}$) (FIG. 17a).

Figure 17B:
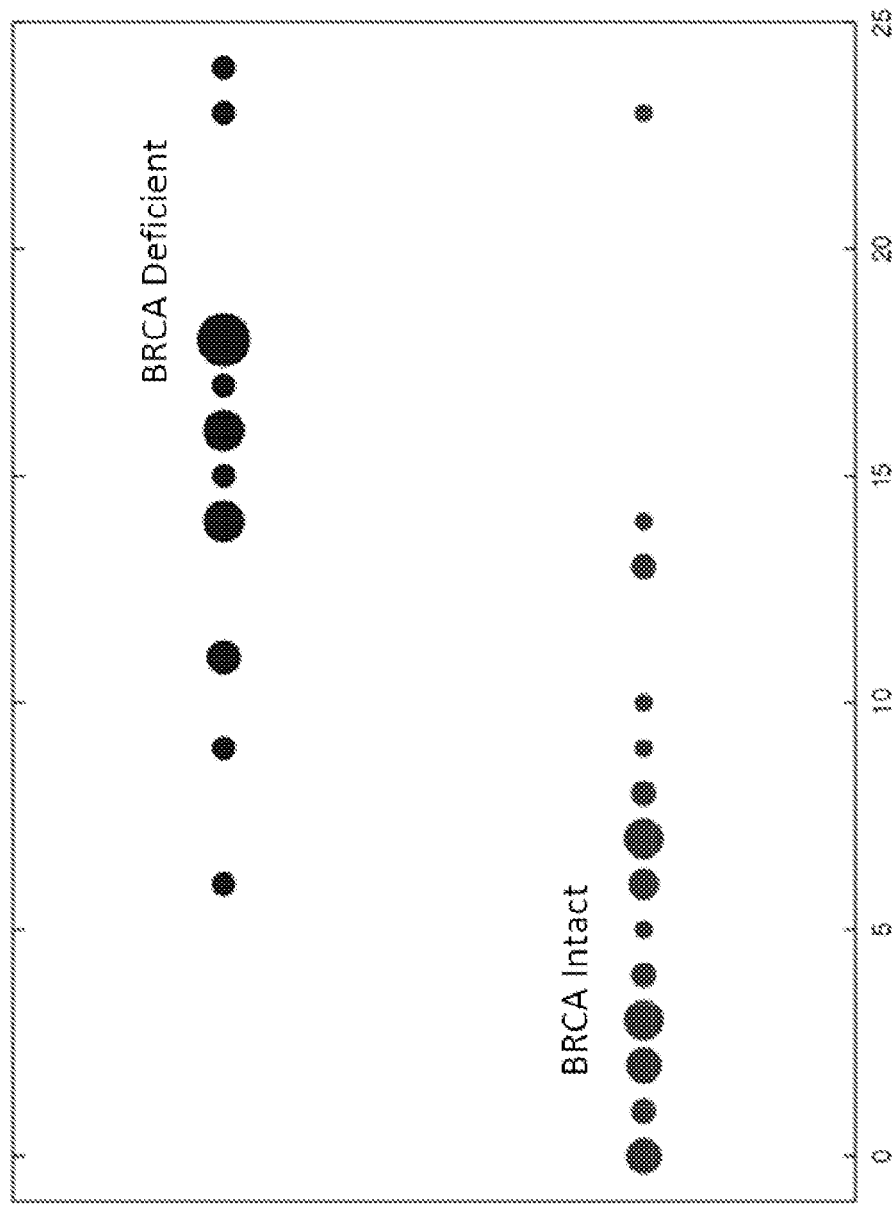
FIG. 17b shows the HRD score in tumor samples for the second cohort (19 of 53 samples were BRCA1 or BRCA2 deficient). Top circles: BRCA1 or BRCA2 deficient samples. Bottom circles: BRCA1 and BRCA2 intact samples. The area of each individual circle is proportional to the number of samples with the corresponding number of LOH regions.
Figure 17C:
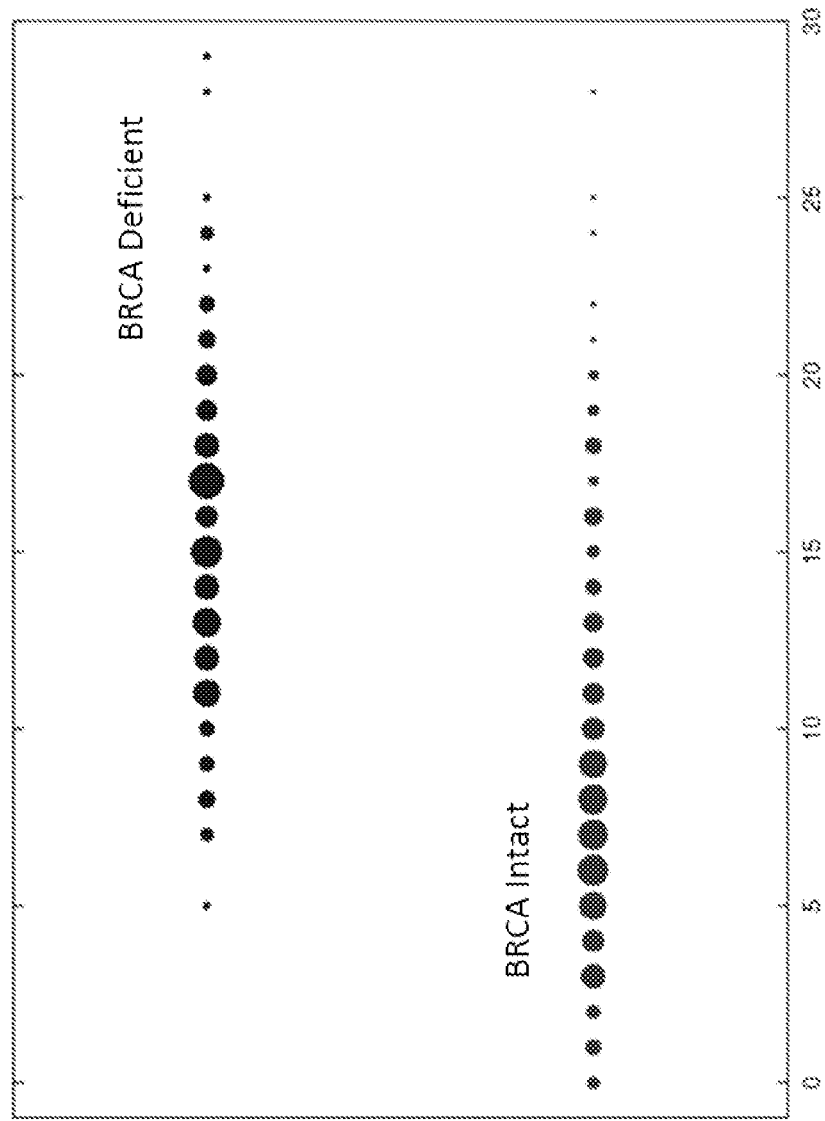
FIG. 17c shows the HRD score in tumor samples for the third cohort (146 of 435 samples were BRCA1 or BRCA2 deficient). Top circles: BRCA1 or BRCA2 deficient samples. Bottom circles: BRCA1 and BRCA2 intact samples. The area of each individual circle is proportional to the number of samples with the corresponding number of LOH regions.

The second and third cohorts were used to validate the results obtained for the first cohort. The correlation between HR deficiency and number of LOH regions covering whole chromosomes did not validate in the second cohort, possibly due to low sample number, but was significantly larger ($p=3 \times 10^{-11}$) among tumors with intact BRCA1 and BRCA2 in the third cohort. A highly significant correlation was observed between HRD score and HR deficiency for both cohorts ($p=2 \times 10^{-7}$ and $p=9 \times 10^{-30}$ respectively) with HRD score being distinctly reduced among ovarian tumors with intact BRCA1 and BRCA2 (FIGS. 17b and 17c).

Alterations in RAD51C and Other HR Pathway Genes

Available data suggest that BRCA1 and BRCA2 are the primary genes responsible for HR deficiency in ovarian cancer. However, many other genes may also be important with, for example, both RAD51C (Meindl et al., 2010) and RAD51D (Loveday et al., 2011) recently being implicated as predisposition genes for ovarian cancer. The degree of methylation was measured for promoter CpG islands of eight additional genes involved in the HR pathway (Table 5) in the first cohort. Only RAD51C had high levels of promoter methylation (3 of 89 samples). In the third cohort 11 of 435 samples had methylation of the RAD51C promoter. All samples positive for RAD51C methylation from both cohorts were homozygous at the RAD51C locus due to LOH. To test whether the HRD score is elevated in samples with RAD51C promoter methylation these samples from both cohorts were compared with BRCA intact samples without RAD51C methylation. Consistent with our observations for BRCA1 and BRCA2 genes, HRD score was significantly higher ($p=0.0003$) among samples with RAD51C methylation.

TABLE 5

Promoter methylation assays used (SABiosciences).

| Gene Symbol | Description | Assay catalog ID |
|---|---|---|
| MDC1 | Mediator or DNA damage checkpoint 1 | MePH08721-2A |
| PARP1 | Poly(ADP-ribose) polymerase 1 | MePH02379-2A |
| BRCA1 | Breast Cancer 1, early onset | MePH28472-1A |
| BRCA2 | Breast Cancer 2, early onset | MePH28473-1A |
| RAD50 | RAD50 homolog | MePH28350-1A |
| RAD51C | RAD51 homolog C | MePH22389-1A |
| PALB2 | Partner and localizer of BRCA2 | MePH28516-1A |
| CHEK2 | CHK2 checkpoint homolog | MePH28264-1A |
| ATM | Ataxia telangiectasia mutated | MePH28470-1A |
| RAD51 | RAD51 homolog | MePH19071-2A |

In the third cohort deleterious mutations and methylation of HR pathway genes have been reported (TCGA, 2011). The mutations were examined and analysis limited to defects with a high likelihood of being deleterious (e.g., nonsense and frameshift mutations), resulting in a total of 8 deleterious mutations in 6 genes (ATM, ATR, FANCA, FANCD2, FANCM, and PALB2). An additional 5 samples had methylation of HR pathway genes. Loss of the second allele was detected in only 1 of the 13 samples (a FANCM nonsense mutation). Since deactivation of both alleles is needed to loose function of a tumor suppressor, most of these 13 samples are expected to have intact HR. Not surprisingly, HRD score was not elevated in the majority of these samples.

Analysis of Combined Data

Figure 17D:
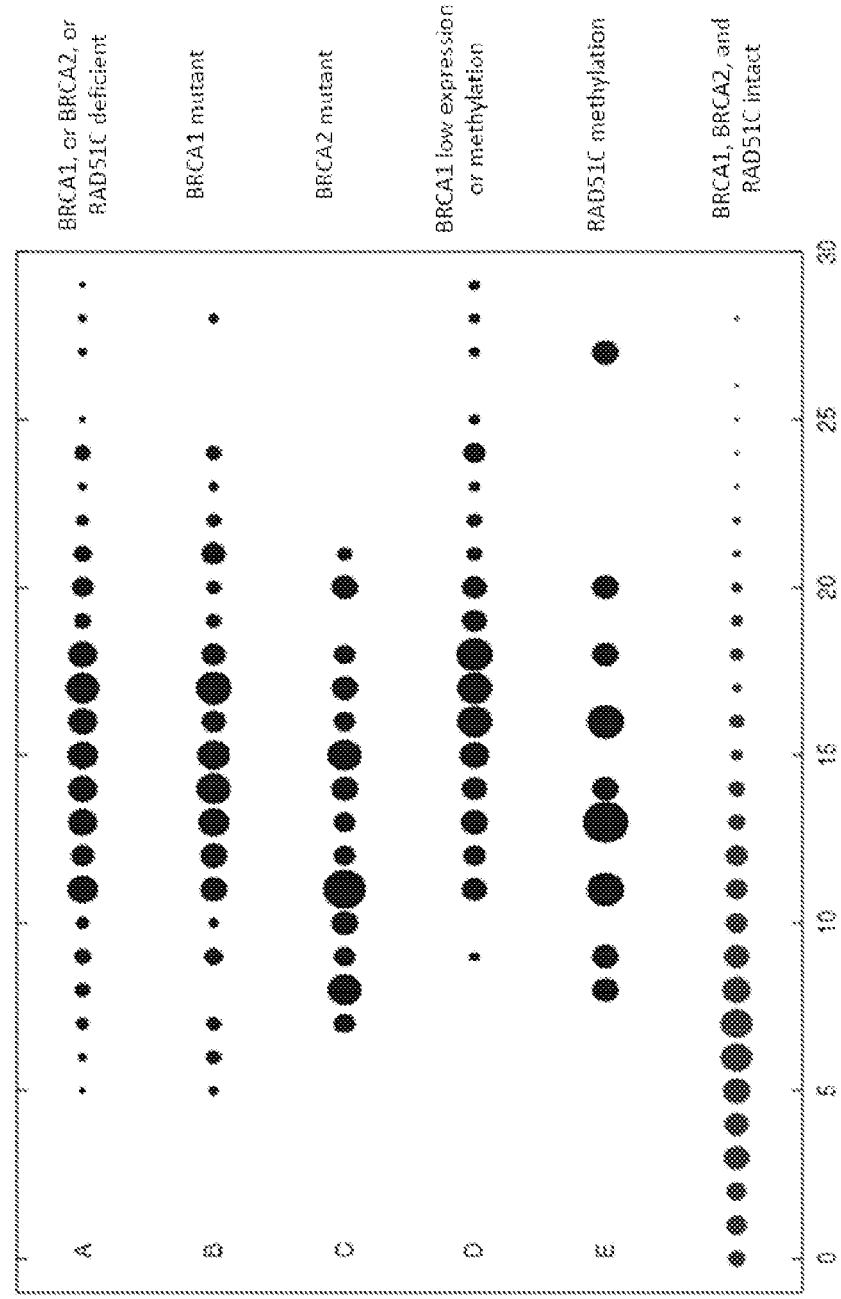
FIG. 17d shows the HRD score in tumor samples for the combined data from all three cohorts. Row A: 224 samples with either BRCA1, or BRCA2, or RAD51C deficient genes; Row B: 84 BRCA1 mutants; Row C: 43 BRCA2 mutants; Row D: 82 samples with low expression or methylation of BRCA1; Row E: 13 samples with methylation of RAD51C. Bottom circles: 416 samples with BRCA1, BRCA2, and RAD51C intact genes.

Correlation between HRD score and HR deficiency (defined as deficiency of BRCA1, BRCA2, or RAD51C) for all three cohorts is presented in the FIG. 17d. A highly significant association is seen ($p=2 \times 10^{-54}$).

Figure 21:
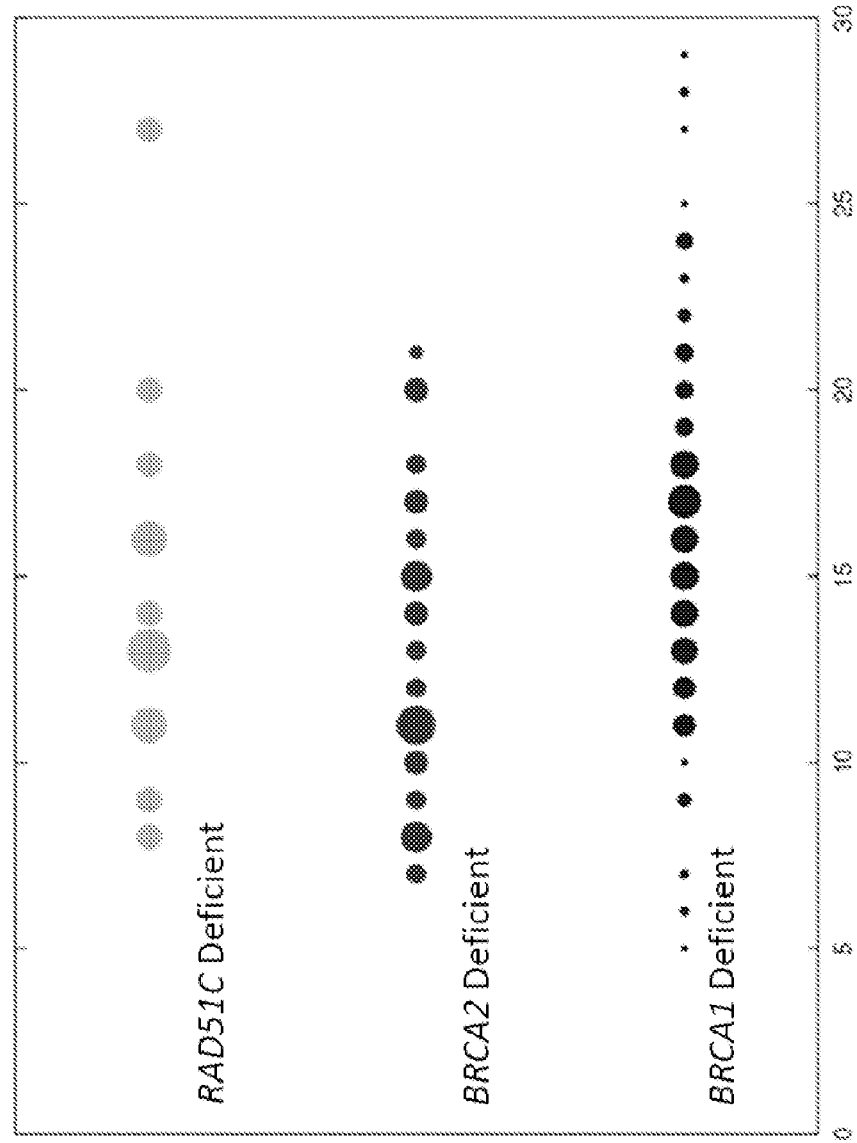
FIG. 21 shows a comparison of LOH scores of BRCA1, BRCA2, and RAD51C deficient samples. Blue circles correspond to BRCA1 deficient samples, red circles correspond to BRCA2 deficient samples, and green circles correspond to RAD51C deficient samples. The combined area under red, blue, and green circles is the same. The area under each individual circle is proportional to the number of samples with the corresponding number of LOH regions.
Figure 22:
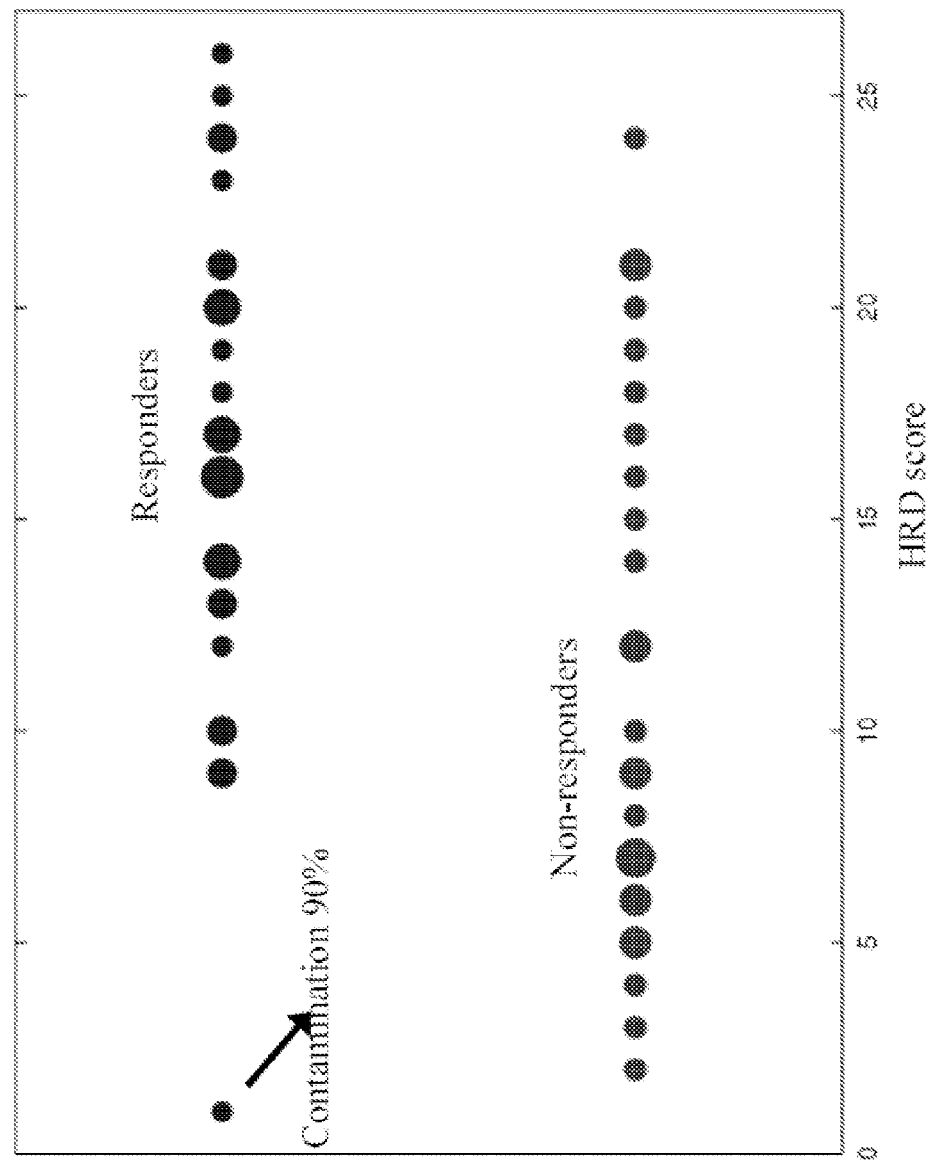
FIG. 22 shows a comparison of LOH ("HRD") scores in patients who responded versus patients who did not respond to treatment comprising platinum therapy. The area under each individual circle is proportional to the number of samples with the corresponding number of LOH regions.
Figure 23:
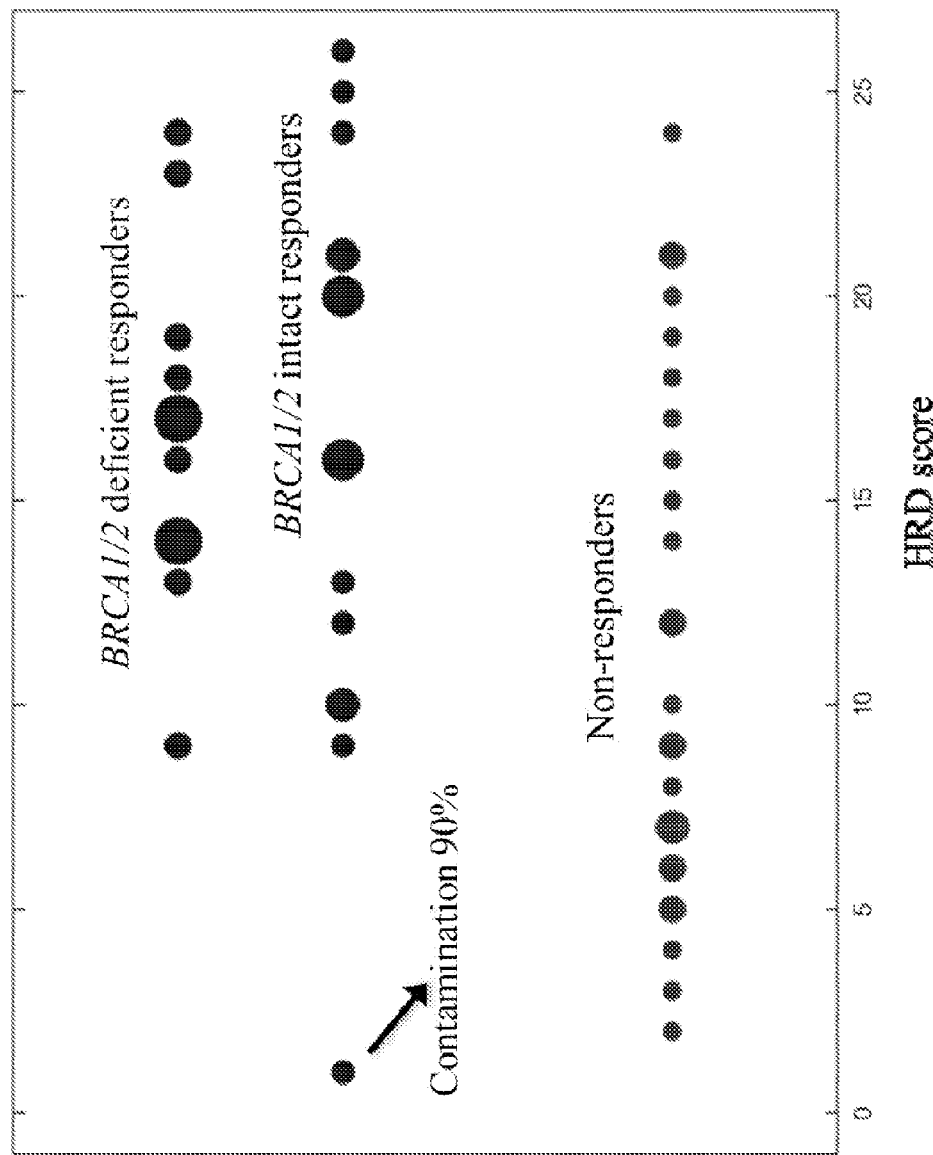
FIG. 23 shows a comparison of LOH ("HRD") scores in BRCA1 or BRCA2 deficient samples. The area under each individual circle is proportional to the number of samples with the corresponding number of LOH regions. One outlier sample with significant contamination is highlighted.
Figure 24:
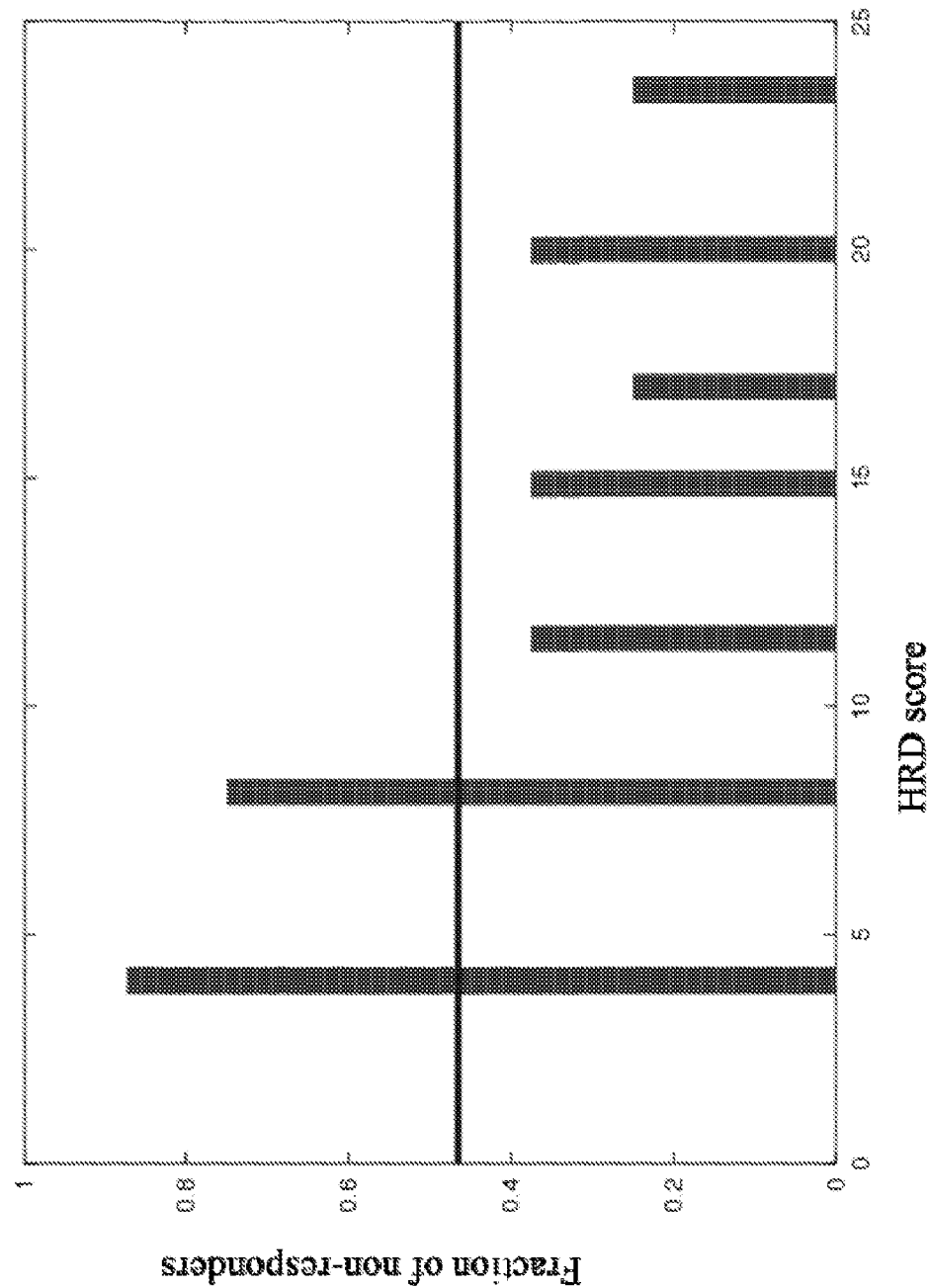
FIG. 24 shows the fraction of non-responders in each group of patients with a given LOH ("HRD") score.

An important question is whether the distribution of HRD scores is the same for HR deficiency due to different genomic loci. To answer this, the distributions of HRD scores for BRCA1, BRCA2, and RAD51C deficient tumors were analyzed separately (FIG. 21). A significant difference was observed ($p=7\times10^{-5}$) with BRCA1 deficient samples having higher average HRD score (16.1; SD=4.3) than BRCA2 deficient samples (13.0; SD=3.9). The differences in HRD scores between either BRCA1 or BRCA2 and RAD51C (14.5; SD=5.1) were not significant.

Figure 20:
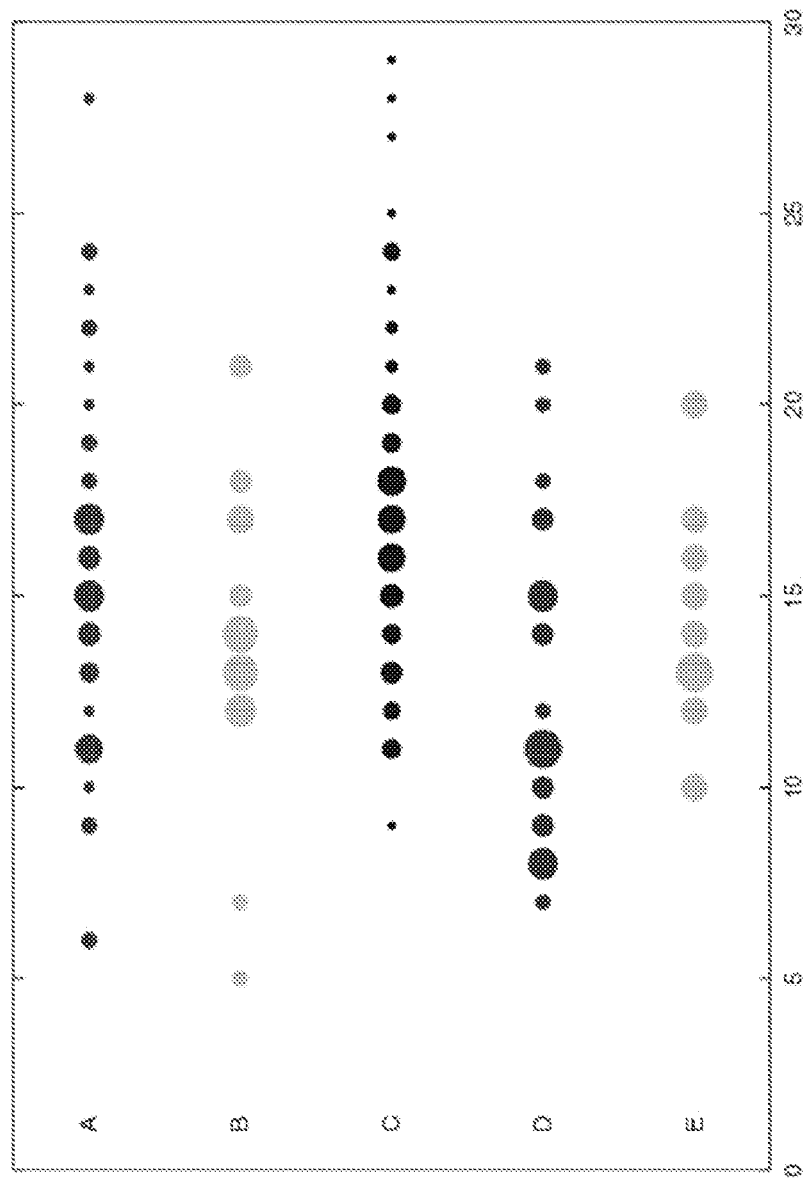
FIG. 20 shows comparison of LOH scores in three groups of BRCA1 and BRCA2 deficient samples for the combined data from all three cohorts. Row A: 49 carriers of germline mutations in BRCA1; B: 25 carriers of somatic mutations in BRCA1; C: 82 samples with either methylation or low expression of BRCA1; D: 27 carriers of germline mutations in BRCA2; E: 9 carriers of somatic mutations in BRCA2.

Normal tissue was available from some samples from the first two cohorts and all samples from the third cohort, this was used to determine whether mutations in BRCA1 and BRCA2 were germline or somatic. There is no significant difference for somatic vs. germline in the distributions of HRD scores for either BRCA1 or BRCA2 deficiency (FIG. 20).

dataset ($p=0.01$), suggesting that association of HRD score with HR deficiency is not restricted to ovarian cancer.

Correlation Between HR Deficiency and Overall Survival (OS) and Progression Free Survival (PFS)

Figure 18A:
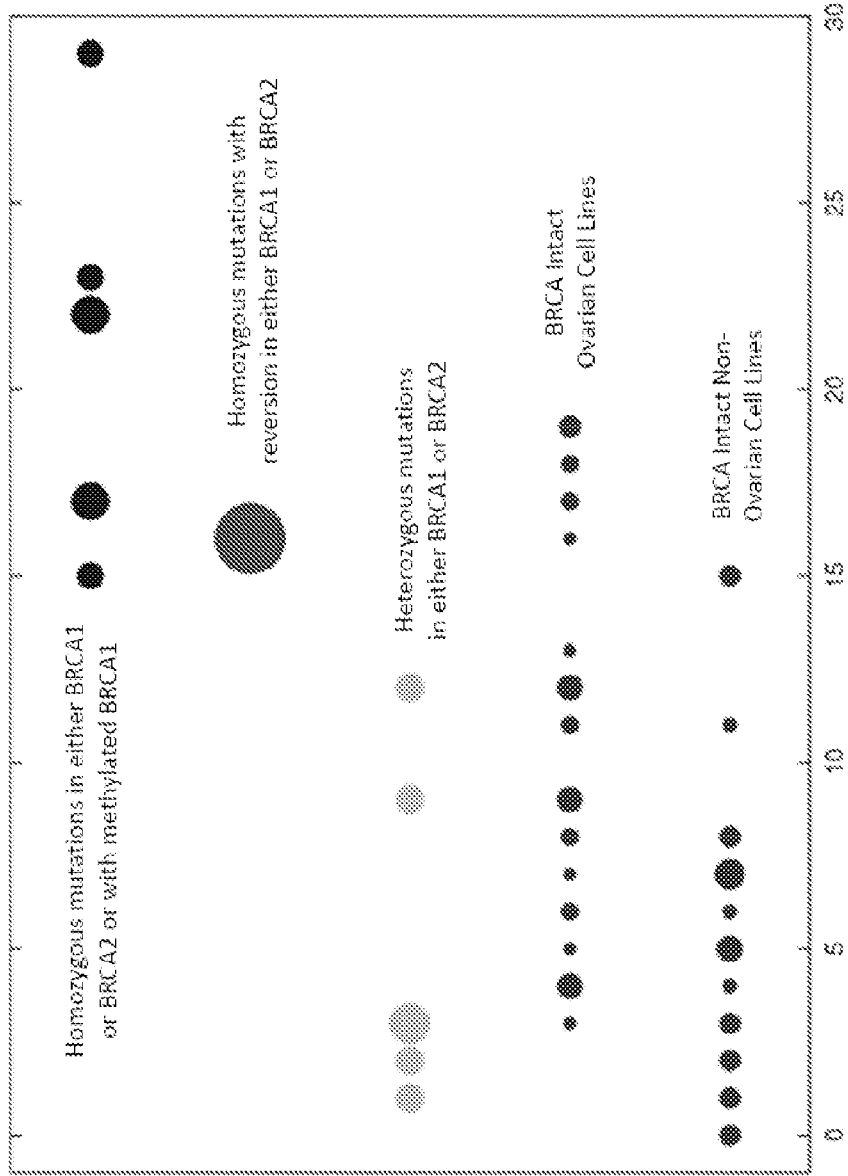
FIG. 18a. Comparison of HRD scores in cancer cell lines. Red circles: cell lines with intact BRCA1 or BRCA2. A: 30 intact non-ovarian cell lines; B: 22 intact ovarian cell lines. Green circles: 6 carriers of heterozygous mutations in either BRCA1 or BRCA2. Violet circles: 2 carriers of homozygous mutations with reversion in either BRCA1 or BRCA2. Blue circles: 7 carriers of homozygous mutations in either BRCA1 or BRCA2 or with methylated BRCA1. The combined area under the green, red, blue, and violet circles is the same. The area under each individual circle is proportional to the number of samples with the corresponding number of LOH regions.
Figure 18B:
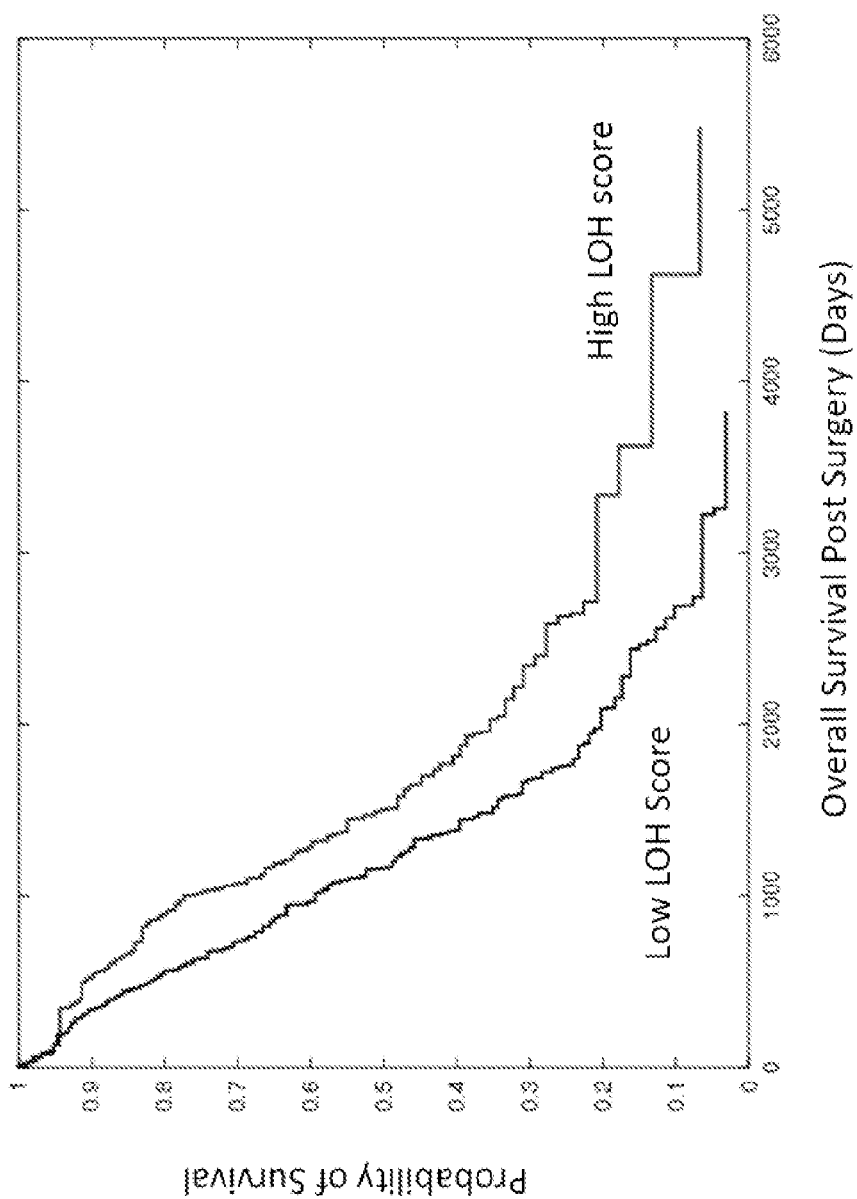
FIG. 18b. Kaplan-Meier plot of OS post-surgery for HRD score split at its median. These data were generated using 507 samples from the TCGA dataset for which copy number data and survival information were available. Median OS for samples with high and low HRD score were 1499 (95% CI=(1355-1769)) and 1163 (95% CI=(1081-1354)) days, respectively.

A significant correlation was observed between PFS ($p=0.03$) and OS ($p=6\times10^{-5}$) for the third cohort with improved survival for patients with higher HRD scores (FIG. 18b). P-values were calculated using Cox model. The results are in agreement with, and extend previously reported data showing that germline mutations in BRCA1 and BRCA2 are associated with improved outcomes for ovarian cancer (Rubin et al., 1996, Boyd et al., 2000; Cass et al., 2003; Tan et al., 2008, Hennessy et al., 2010,).

Discussion

The HRD score was validated in two independent ovarian cancer datasets, and also reflected mutations resulting in HR deficiency in breast and pancreatic cell lines.

TABLE 6

Average of HRD score for BRCA1 and BRCA2 deficient and intact tumors and corresponding p values.

| | HR deficient (BRCA1 and BRCA2) | HR intact (BRCA1 and BRCA2) | HR deficient (BRCA1, BRCA2, and RAD51C) | HR intact (BRCA1, BRCA2, and RAD51C) |
|---|---|---|---|---|
| First cohort | 15.9 (SD = 4.6) $p = 9 \times 10^{-11}$ | 8.3 (SD = 6.1) | 16.2 (SD = 4.9) $p = 7 \times 10^{-12}$ | 8.0 (SD = 5.8) |
| Second cohort | 15.6 (SD = 4.4) $p = 2 \times 10^{-7}$ | 5.6 (SD = 4.9) | 15.6 (SD = 4.4) $p = 2 \times 10^{-7}$ | 5.6 (SD = 4.9) |
| Third cohort | 15.3 (SD = 4.3) $p = 9 \times 10^{-30}$ | 8.8 (SD = 5.0) | 15.1 (SD = 4.3) $p = 2 \times 10^{-32}$ | 8.6 (SD = 5.0) |
| Combined data for three cohorts | 15.5 (SD = 4.4) $p = 10^{-45}$ | 8.4 (SD = 5.3) | 15.4 (SD = 4.4) $p = 2 \times 10^{-54}$ | 8.2 (SD = 5.2) |
| Cancer cell lines | 19.7 (SD = 4.6) $p = 10^{-5}$ | 8.2 (SD = 5.4) | 19.7 (SD = 4.6) $p = 10^{-5}$ | 8.2 (SD = 5.4) |

HRD Score in BRCA1 and BRCA2 Deficient Cell Lines

Unselected breast (n=34) and ovarian (n=29) cell lines were obtained from multiple sources; in addition 3 colon and one pancreatic cell line from NCI60 with published BRCA1 and BRCA2 status were analyzed. Of these 67 cell lines, seven either carried homozygous deleterious mutations or had methylation of the BRCA1 promoter, two had homozygous mutations with apparent functional reversion, and six carried heterozygous mutations. FIG. 18a shows the distributions of HRD scores for these three groups of mutants, as well as for wild type samples. The distributions of HRD scores among wild type ovarian tumors and wild type cancer cell lines are not significantly different. The distribution of HRD scores among cancer cell lines with heterozygous mutations is similar to wild type cancer cell lines, presumably because cells become HR deficient only when both copies of BRCA1 or BRCA2 are non-functional. For cancer cell lines with functional loss of both copies of either BRCA1 or BRCA2, higher HRD scores are observed, similar to HRD scores observed for ovarian tumors with BRCA1, BRCA2, or RAD51C deficient genes. HRD scores are also high for cancer cell lines with reversion of BRCA1 and BRCA2 mutations. This supports the original hypothesis that HR deficiency results in irreversible changes in LOH. The difference of the distribution of HRD scores in either wild type or heterozygous mutant cell lines, and the distribution of HRD scores in cell lines with either homozygous mutations (with or without reversion) or methylation of the BRCA1 promoter is highly significant ($p=10^{-5}$). Importantly, there is significant correlation between HRD score and BRCA1 and BRCA2 deficiency after excluding ovarian cancer cell lines from the An intermediate class of LOH sizes greater than 15 Mb but less than a whole chromosome is highly positively correlated with defective HR genes suggesting that most if not all, of this type of LOH class exists because it incorporates double strand DNA breaks as part of its genesis and requires repair by HR. In contrast, LOH at the whole chromosome level is significantly less frequent in HR deficient tumors. One possible explanation is that LOH at the whole chromosome level originates through an alternative competing mechanism that does not involve double strand DNA breaks.

In addition to BRCA1 and BRCA2 defects, RAD51C promoter methylation is observed in ovarian tumors. High HRD score was significantly associated with RAD51C deficiency in two datasets. Only one additional HR deficient tumor was confirmed in the 3 datasets, a nonsense mutation in FANCM with LOH resulting in loss of the second allele. The HRD score associated with the FANCM mutation (8) is within the range of the normal distribution for samples with elevated HRD score.

Among tumors with apparently intact BRCA1, BRCA2, and RAD51C, a substantial fraction of the samples have an elevated HRD score. One possible explanation is that there is a substantial rate of defects in other genes in the HR pathway in many of these samples. An alternative explanation is that contamination of the tumor with normal tissue complicates detection of defects. Data suggest that the HRD score is less sensitive to contamination than other assays, and that undetected defects may explain a significant fraction of those samples with elevated HRD score (see Supplementary Results).

Published studies have demonstrated that secondary reversion mutations which restore BRCA2 function can arise in BRCA2 mutant cell lines after exposure to platinum agents (Sakai et al., 2009; Sakai et al., 2008; Edwards et al., 2008). Norquist et al., (2011) observed that approximately 28% of recurrent tumors had a secondary mutation that restored BRCA function. Reversion mutations were seen primarily in individuals with prior exposure to platinum agents and were predictive of resistance to platinum. The HRD score results from cumulative defects occurring in the genome of the tumor. DNA based markers of HR deficiency are likely to be strongly associated with HR deficiency because they are functionally linked to it. Consequently, the HRD score is a very robust measure of HR deficiency. However, its permanence means the score would likely not be sensitive to reversion mutations. Post-treatment samples were not available from the tumors used in this study, however data obtained from cell lines is consistent with this hypothesis. Failure to detect reversion mutations will result in false positives. This is likely to affect very few tumors in the neoadjuvant or adjuvant setting (Norquist et al., 2011) and is less of a concern than false negatives which would incorrectly identify individuals as likely non-responders.

High HRD score is highly correlated with HR deficiency, and this score can be utilized to identify patients with high likelihood of responding to DNA damaging agents and PARP inhibitors (among other agents). Such a test has clear clinical utility in breast and ovarian cancer, and can be used to expand the use of PARPi and platinum salts to other cancers where HR deficiency is less well characterized.

Example 4

Further Validation of HR Deficiency Assay

Materials and Methods

The patient cohort analyzed in this example included 56 breast cancer patients, all of whom are either BRCA mutation positive or have triple negative breast cancer (most are TNBC). Stages I-III were included (most are II or III). The patients received 6 cycles of neoadjuvant gemcitabine+iniparib+carboplatin. Response was measured as relatively lower residual cancer burden following treatment.

56 fresh frozen breast tumors were analyzed. Median degree of contamination is 60%. Nine samples had contamination of at least 90%. 11 of these tumors were carriers of BRCA1 deleterious mutations and three were carriers of BRCA2 deleterious mutations. In all of these tumors there was LOH at the deficient genes. One of the carriers of BRCA1 deleterious mutations also carried a deleterious mutation in BRCA2. However in that sample there was no LOH at BRCA2 gene.

30 samples were obtained from patients who responded to treatment (residual cancer burden either 0 or 1). 13 of them are BRCA1/2 deficient. 26 samples were obtained from non-responders (residual cancer burden either 2 or 3). One of them is BRCA1 deficient. Genotyping analysis was performed by Affymetrix using Affymetrix MIP arrays (as described in U.S. Pat. No. 6,858,412; U.S. Patent Application Publication No. US20060234264; Hardenbol et al., Nature Biotechnology (2003) 21: 673-678; Wang et al., BMC Med Genomics (2009) 2:8; each of which is hereby incorporated by reference in its entirety). HRD scores were calculated as described above.

Results

The average HRD score for responders was 16.5. The average HRD score for BRCA1/2 intact and for BRCA1/2 deficient responders was the same. The average HRD score for non-responders was 11.4. The average HRD score for BRCA1/2 intact non-responders is 11.6 and for BRCA1 deficient non-responder was 8. According to the Mann-Whitney U test p-value for association between response to treatment and HRD score was 0.004. If BRCA1/2 deficient samples are excluded association between response to treatment and HRD score remains significant (p-value=0.02).

The differences in HRD score amongst samples with residual cancer burden 0 and 1 were not significant. Similarly, the differences in HRD score amongst samples with residual cancer burden 2 and 3 were not significant. Correlations between response to treatment and clinical parameters (stage, grade) were not significant.

OTHER EMBODIMENTS

It is to be understood that while the invention has been described in conjunction with the detailed description thereof, the foregoing description is intended to illustrate and not limit the scope of the invention, which is defined by the scope of the appended claims. Other aspects, advantages, and modifications are within the scope of the following claims.

What is claimed is:

1. A method of treating cancer, comprising:
    (1) assaying a cancer cell sample obtained from a test breast or ovarian cancer patient to detect a test number of Indicator LOH Regions in at least ten pairs of human chromosomes, wherein an Indicator LOH Region is equal to or longer than a first length but shorter than the length of the whole chromosome containing the Indicator LOH Region, and wherein the first length is at least 5 megabases;
    (2) providing a test value equal to or derived from the test number of Indicator LOH Regions detected in (1);
    (3) determining that said test value exceeds a reference value equal to or derived from a reference number of Indicator LOH Regions in said at least ten pairs of human chromosomes in cancer cell samples of a population of reference breast or ovarian cancer patients, wherein said reference number of Indicator LOH Regions is at least five; and
    (4) administering to the test breast or ovarian patient a treatment regimen comprising one or both of a platinum chemotherapy agent or a PARP inhibitor drug.

2. The method of claim 1 comprising assaying said cancer cell sample to detect a test number of Indicator LOH Regions in at least 15 pairs of human chromosomes.

3. The method of claim 1 comprising assaying said cancer cell sample to detect a test number of Indicator LOH Regions in at least 21 pairs of human chromosomes.

4. The method of claim 1, wherein the first length is at least 10 megabases.

5. The method of claim 1, wherein the first length is at least 12 megabases.

6. The method of claim 1, wherein the first length is at least 15 megabases.

7. The method of claim 1, wherein the reference number of Indicator LOH Regions is at least ten.

8. The method of claim 1, wherein the reference number of Indicator LOH Regions is at least 12.

9. The method of claim 1, wherein the reference number of Indicator LOH Regions is at least 15.

10. The method of claim 1, wherein the platinum chemotherapy agent is carboplatin.

11. The method of claim 1, wherein the PARP inhibitor drug is olaparib.

12. A method of treating cancer, comprising:
   (1) assaying a cancer cell sample obtained from a test breast or ovarian cancer patient to detect a test number of Indicator LOH Regions in at least ten pairs of human chromosomes, wherein
      (a) the assaying in (1) comprises genotyping a plurality of single nucleotide polymorphism loci by
         (i) enriching the sample for DNA molecules each comprising at least one locus from the plurality of single nucleotide polymorphism loci, wherein the plurality of single nucleotide polymorphism loci comprises at least 1,000 single nucleotide polymorphism loci and wherein there is at least one single nucleotide polymorphism locus located on average every 500 kb within each chromosome of the ten pairs of human chromosomes; and
         (ii) assaying the test DNA molecules to determine whether each locus in the plurality of single nucleotide polymorphism loci is homozygous or heterozygous;
      (b) an Indicator LOH Region is defined as a genomic region wherein all single nucleotide polymorphism loci genotyped in (a) are homozygous, wherein such genomic region is equal to or longer than a first length but shorter than the length of the whole chromosome containing the genomic region, and wherein the first length is at least 5 megabases;
   (2) providing a test value equal to or derived from the test number of Indicator LOH Regions detected in (1);
   (3) determining that said test value exceeds a reference value equal to or derived from a reference number of Indicator LOH Regions in said at least ten pairs of human chromosomes in patient cancer cell samples of a population of reference breast or ovarian cancer patients, wherein said reference number of Indicator LOH Regions is at least five; and
   (4) administering to the test breast or ovarian cancer patient a treatment regimen comprising one or both of a platinum chemotherapy agent or a PARP inhibitor drug.

13. The method of claim 12 comprising assaying said cancer cell sample to detect a test number of Indicator LOH Regions in at least 15 pairs of human chromosomes.

14. The method of claim 12 comprising assaying said cancer cell sample to detect a test number of Indicator LOH Regions in at least 21 pairs of human chromosomes.

15. The method of claim 12, wherein the plurality of single nucleotide polymorphism loci comprises at least 10,000 single nucleotide polymorphism loci.

16. The method of claim 12, wherein the plurality of single nucleotide polymorphism loci comprises at least 25,000 single nucleotide polymorphism loci.

17. The method of claim 12, wherein the plurality of single nucleotide polymorphism loci comprises at least 50,000 single nucleotide polymorphism loci.

18. The method of claim 12, wherein the first length is at least 10 megabases.

19. The method of claim 12, wherein the first length is at least 12 megabases.

20. The method of claim 12, wherein the first length is at least 15 megabases.

21. The method of claim 12, wherein the reference number of Indicator LOH Regions is at least ten.

22. The method of claim 12, wherein the reference number of Indicator LOH Regions is at least 12.

23. The method of claim 12, wherein the reference number of Indicator LOH Regions is at least 15.

24. The method of claim 12, wherein the platinum chemotherapy agent is carboplatin.

25. The method of claim 12, wherein the PARP inhibitor drug is olaparib.

26. A method of treating cancer, comprising:
   (1) assaying a cancer cell sample obtained from a test breast or ovarian cancer patient to detect a test number of Indicator LOH Regions in at least ten pairs of human chromosomes, wherein an Indicator LOH Region is equal to or longer than a first length but shorter than the length of the whole chromosome containing the Indicator LOH Region, and wherein the first length is at least 5 megabases;
   (2) providing a test value equal to or derived from the test number of Indicator LOH Regions detected in (1);
   (3) determining whether said test value exceeds a reference value equal to or derived from a reference number of Indicator LOH Regions in at least ten pairs of human chromosomes in cancer cell samples of a population of reference breast or ovarian cancer patients, wherein said reference number of Indicator LOH Regions is at least five; and either
   (4)(a) administering to the test breast or ovarian patient a treatment regimen comprising one or both of a platinum chemotherapy agent or a PARP inhibitor drug if said test value exceeds said reference value; or
   (4)(b) administering to the test breast or ovarian patient a treatment regimen not comprising one or both of a platinum chemotherapy agent or a PARP inhibitor drug if said test value does not exceed said reference value.

27. The method of claim 26 comprising assaying said cancer cell sample to detect a test number of Indicator LOH Regions in at least 15 pairs of human chromosomes.

28. The method of claim 26 comprising assaying said cancer cell sample to detect a test number of Indicator LOH Regions in at least 21 pairs of human chromosomes.

29. The method of claim 26, wherein the first length is at least 10 megabases.

30. The method of claim 26, wherein the first length is at least 12 megabases.

31. The method of claim 26, wherein the first length is at least 15 megabases.

32. The method of claim 26, wherein the reference number of Indicator LOH Regions is at least ten.

33. The method of claim 26, wherein the reference number of Indicator LOH Regions is at least 12.

34. The method of claim 26, wherein the reference number of Indicator LOH Regions is at least 15.

35. The method of claim 26, wherein the platinum chemotherapy agent is carboplatin.

36. The method of claim 26, wherein the PARP inhibitor drug is olaparib.

* * * * *